United States Patent [19]
Takahashi et al.

[11] Patent Number: 5,874,241
[45] Date of Patent: Feb. 23, 1999

[54] CLOCK GENE AND GENE PRODUCT

[75] Inventors: Joseph S. Takahashi, Wilmette; Fred W. Turek, Chicago; Lawrence H. Pinto, Evanston, all of Ill.

[73] Assignee: Northwestern University, Evanston, Ill.

[21] Appl. No.: 816,693

[22] Filed: Mar. 13, 1997

[51] Int. Cl.⁶ .......................... C12P 21/06; C12N 15/00; C07H 17/00; C07K 14/00
[52] U.S. Cl. ...................... 435/69.1; 435/325; 435/252.3; 435/320.1; 536/23.1; 536/24.3; 514/44
[58] Field of Search ................................... 435/69.1, 525, 435/252.3, 320.1; 536/23.1, 24.3; 514/44; 530/350

[56] References Cited

PUBLICATIONS

Vitaterna et al. 1994 Science 264:719–725.

*Primary Examiner*—Karen Cochrane Carlson
*Attorney, Agent, or Firm*—Rockey, Milnamow & Katz, Ltd.

[57] ABSTRACT

The present invention provides isolated and purified polypeptide components of the mammalian circadian clock, polynucleotides that encode those polypeptides, expression vectors containing those polynucleotides, host cells transformed with those expression vectors, a process of making the polypeptide components using those polynucleotides and vectors, and processes using those polypeptides and polynucleotides.

35 Claims, 24 Drawing Sheets

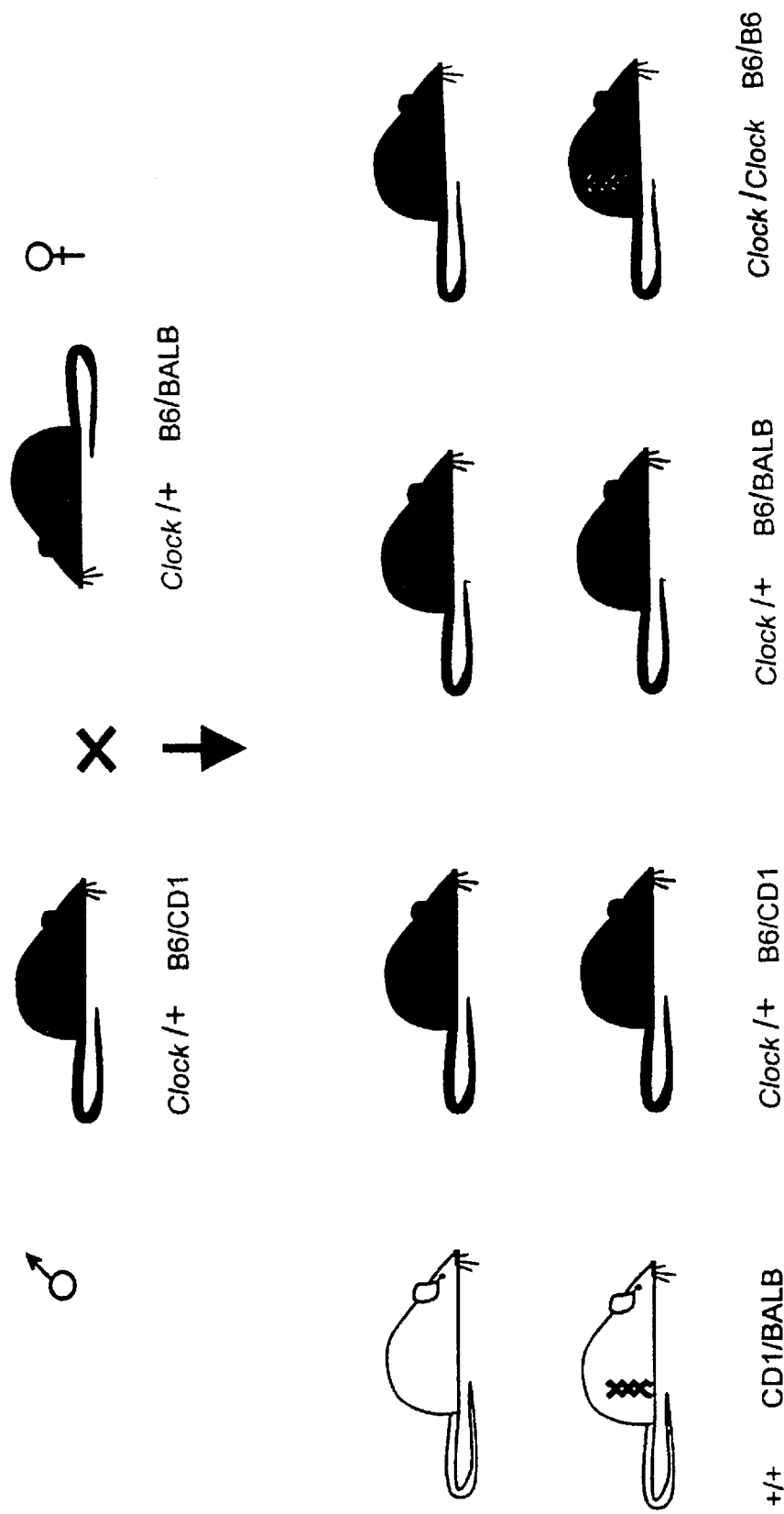

Figure 8A

```
GGGGAGGAGC GCGGCGGTAG CGGTGAATTT TGAGGGGTGG GTCGGGGGCG CGCACTCGCC   60
GCCCCTGGTG CTGCCGGCTC CCGGAGCCGT GGCGTGTCCC TGCTGTCGCC GCTCGGCTGT  120
CGCGAGCCGC CGCGGGCAGA GTCCCGGGCG GGGGAGGGAG GAAGCCGGAG CCTCAGGCAC  180
GTGAAAGAAA AGCACAAGAA GAAACTTTTA CAGGCGTTGT TGATTGGACT AGGGCAACGA  240
TTCCCAAAAT CACCAGCAAG AGTTCTGATG GTCAGTCACA CAGAAGACGG CCTTGCGTCT  300
GTGGGTGTTG GAGACTCCAT TCTAAAGATA TAAAAAGTGA AAGAGGAGAA GTACAAATGT  360
```

```
CTACCACAAG ACGAAAACAT AATGTGTT ATG GTG TTT ACC GTA AGC TGT AGT   412
                                Met Val Phe Thr Val Ser Cys Ser
                                 1                   5

AAA ATG AGC TCA ATT GTT GAC AGA GAT GAC AGT AGT ATT TTT GAT GGA   460
Lys Met Ser Ser Ile Val Asp Arg Asp Asp Ser Ser Ile Phe Asp Gly
         10              15                  20

TTG GTG GAA GAA GAT GAC AAG GAC AAA GCA AAA AGA GTA TCT AGA AAC   508
Leu Val Glu Glu Asp Asp Lys Asp Lys Ala Lys Arg Val Ser Arg Asn
 25              30              35                      40

AAA TCA GAA AAG AAA CGT AGA GAT CAG TTC AAT GTC CTC ATT AAG GAG   556
Lys Ser Glu Lys Lys Arg Arg Asp Gln Phe Asn Val Leu Ile Lys Glu
                 45              50                      55

CTG GGG TCT ATG CTT CCT GGT AAC GCG AGA AAG ATG GAC AAG TCT ACT   604
Leu Gly Ser Met Leu Pro Gly Asn Ala Arg Lys Met Asp Lys Ser Thr
             60              65                  70

GTT CTA CAG AAG AGC ATT GAT TTT TTG CGC AAA CAT AAA GAG ACC ACT   652
Val Leu Gln Lys Ser Ile Asp Phe Leu Arg Lys His Lys Glu Thr Thr
         75              80                  85

GCA CAG TCA GAT GCT AGT GAG ATT CGA CAG GAC TGG AAA CCC ACA TTC   700
Ala Gln Ser Asp Ala Ser Glu Ile Arg Gln Asp Trp Lys Pro Thr Phe
     90              95                 100

CTT AGT AAT GAA GAG TTT ACA CAG TTA ATG TTA GAG GCT CTT GAT GGT   748
Leu Ser Asn Glu Glu Phe Thr Gln Leu Met Leu Glu Ala Leu Asp Gly
105             110                 115                 120

TTT TTT TTA GCG ATC ATG ACA GAT GGA AGT ATA ATA TAT GTA TCT GAG   796
Phe Phe Leu Ala Ile Met Thr Asp Gly Ser Ile Ile Tyr Val Ser Glu
             125                 130                 135
```

Figure 8B

| | | |
|---|---|---|
| AGT GTA ACT TCG TTA CTT GAA CAT TTA CCA TCT GAT CTT GTG GAT CAA<br>Ser Val Thr Ser Leu Leu Glu His Leu Pro Ser Asp Leu Val Asp Gln<br>            140                     145                     150 | 844 |
| AGT ATA TTT AAT TTT ATC CCA GAG GGA GAA CAT TCA GAG GTT TAT AAG<br>Ser Ile Phe Asn Phe Ile Pro Glu Gly Glu His Ser Glu Val Tyr Lys<br>            155                     160                     165 | 892 |
| ATA CTC TCT ACT CAT CTG CTG GAA AGT GAC TCA TTA ACC CCT GAG TAC<br>Ile Leu Ser Thr His Leu Leu Glu Ser Asp Ser Leu Thr Pro Glu Tyr<br>            170                     175                     180 | 940 |
| TTA AAA TCA AAA AAT CAG TTA GAA TTC TGT TGT CAC ATG CTT CGA GGA<br>Leu Lys Ser Lys Asn Gln Leu Glu Phe Cys Cys His Met Leu Arg Gly<br>185                     190                     195                     200 | 988 |
| ACA ATA GAC CCA AAG GAG CCA TCC ACC TAT GAA TAT GTG AGA TTT ATA<br>Thr Ile Asp Pro Lys Glu Pro Ser Thr Tyr Glu Tyr Val Arg Phe Ile<br>            205                     210                     215 | 1036 |
| GGA AAT TTT AAA TCT TTA ACC AGT GTA TCA ACT TCA ACA CAC AAT GGT<br>Gly Asn Phe Lys Ser Leu Thr Ser Val Ser Thr Ser Thr His Asn Gly<br>            220                     225                     230 | 1084 |
| TTT GAA GGA ACT ATA CAA CGC ACA CAT AGG CCT TCT TAT GAA GAT AGA<br>Phe Glu Gly Thr Ile Gln Arg Thr His Arg Pro Ser Tyr Glu Asp Arg<br>            235                     240                     245 | 1132 |
| GTT TGT TTT GTA GCT ACT GTC AGA TTA GCT ACA CCT CAG TTC ATC AAG<br>Val Cys Phe Val Ala Thr Val Arg Leu Ala Thr Pro Gln Phe Ile Lys<br>            250                     255                     260 | 1180 |
| GAA ATG TGT ACT GTT GAA GAA CCA AAT GAA GAG TTT ACA TCT AGA CAC<br>Glu Met Cys Thr Val Glu Glu Pro Asn Glu Glu Phe Thr Ser Arg His<br>265                     270                     275                     280 | 1228 |
| AGT TTA GAA TGG AAG TTT CTA TTT TTA GAT CAC AGG GCA CCA CCA ATA<br>Ser Leu Glu Trp Lys Phe Leu Phe Leu Asp His Arg Ala Pro Pro Ile<br>            285                     290                     295 | 1276 |
| ATA GGC TAT TTG CCA TTT GAA GTC TTG GGA ACA TCA GGC TAT GAT TAC<br>Ile Gly Tyr Leu Pro Phe Glu Val Leu Gly Thr Ser Gly Tyr Asp Tyr<br>            300                     305                     310 | 1324 |

Figure 8C

```
TAT CAT GTG GAT GAC CTA GAA AAT CTG GCA AAA TGT CAC GAG CAC TTA    1372
Tyr His Val Asp Asp Leu Glu Asn Leu Ala Lys Cys His Glu His Leu
        315                 320                 325

ATG CAA TAT GGA AAA GGC AAA TCG TGT TAC TAT AGA TTC CTG ACC AAA    1420
Met Gln Tyr Gly Lys Gly Lys Ser Cys Tyr Tyr Arg Phe Leu Thr Lys
        330                 335                 340

GGC CAG CAG TGG ATA TGG CTT CAG ACT CAT TAT TAT ATT ACT TAC CAT    1468
Gly Gln Gln Trp Ile Trp Leu Gln Thr His Tyr Tyr Ile Thr Tyr His
345                 350                 355                 360

CAG TGG AAT TCA AGG CCA GAG TTC ATT GTT TGT ACT CAC ACT GTA GTA    1516
Gln Trp Asn Ser Arg Pro Glu Phe Ile Val Cys Thr His Thr Val Val
                365                 370                 375

AGT TAT GCA GAA GTT AGG GCT GAA AGA CGG CGA GAA CTT GGC ATT GAA    1564
Ser Tyr Ala Glu Val Arg Ala Glu Arg Arg Arg Glu Leu Gly Ile Glu
            380                 385                 390

GAG TCT CTT CCT GAG ACA GCT GCT GAC AAA AGC CAA GAT TCT GGG TCT    1612
Glu Ser Leu Pro Glu Thr Ala Ala Asp Lys Ser Gln Asp Ser Gly Ser
            395                 400                 405

GAC AAT CGT ATC AAC ACA GTG AGT CTC AAG GAA GCA CTG GAA AGG TTT    1660
Asp Asn Arg Ile Asn Thr Val Ser Leu Lys Glu Ala Leu Glu Arg Phe
        410                 415                 420

GAT CAC AGC CCA ACT CCT TCT GCC TCC TCT AGA AGC TCA CGA AAG TCA    1708
Asp His Ser Pro Thr Pro Ser Ala Ser Ser Arg Ser Ser Arg Lys Ser
425                 430                 435                 440

TCT CAC ACC GCA GTC TCA GAC CCT TCC TCC ACA CCG ACA AAG ATC CCT    1756
Ser His Thr Ala Val Ser Asp Pro Ser Ser Thr Pro Thr Lys Ile Pro
                445                 450                 455

ACT GAT ACT AGC ACT CCT CCC AGA CAG CAT TTG CCA GCT CAT GAA AAG    1804
Thr Asp Thr Ser Thr Pro Pro Arg Gln His Leu Pro Ala His Glu Lys
            460                 465                 470

ATG ACA CAG CGG AGG TCG TCC TTC AGC AGT CAG TCC ATA AAC TCC CAG    1852
Met Thr Gln Arg Arg Ser Ser Phe Ser Ser Gln Ser Ile Asn Ser Gln
        475                 480                 485
```

Figure 8D

| | | | | | | | | | | | | | | | |
|---|---|---|---|---|---|---|---|---|---|---|---|---|---|---|---|
| TCA | GTT | GGT | CCA | TCA | TTA | ACA | CAG | CCA | GCG | ATG | TCT | CAA | GCT | GCA | AAT | 1900 |
| Ser | Val | Gly | Pro | Ser | Leu | Thr | Gln | Pro | Ala | Met | Ser | Gln | Ala | Ala | Asn | |
| | 490 | | | | 495 | | | | | 500 | | | | | | |

```
TCA GTT GGT CCA TCA TTA ACA CAG CCA GCG ATG TCT CAA GCT GCA AAT    1900
Ser Val Gly Pro Ser Leu Thr Gln Pro Ala Met Ser Gln Ala Ala Asn
    490             495             500

TTA CCA ATT CCA CAA GGC ATG TCA CAG TTT CAG TTT TCA GCT CAG TTA    1948
Leu Pro Ile Pro Gln Gly Met Ser Gln Phe Gln Phe Ser Ala Gln Leu
505             510             515                 520

GGA GCC ATG CAG CAT CTA AAA GAC CAG CTA GAG CAG CGG ACA CGG ATG    1996
Gly Ala Met Gln His Leu Lys Asp Gln Leu Glu Gln Arg Thr Arg Met
                525             530             535

ATA GAG GCA AAT ATT CAT CGG CAG CAA GAA GAA CTA AGG AAA ATT CAA    2044
Ile Glu Ala Asn Ile His Arg Gln Gln Glu Glu Leu Arg Lys Ile Gln
            540             545             550

GAG CAA CTT CAG ATG GTC CAT GGT CAA GGG CTA CAG ATG TTT TTG CAG    2092
Glu Gln Leu Gln Met Val His Gly Gln Gly Leu Gln Met Phe Leu Gln
            555             560             565

CAA TCA AAC CCT GGA TTG AAT TTT GGT TCT GTT CAA CTT TCC TCT GGA    2140
Gln Ser Asn Pro Gly Leu Asn Phe Gly Ser Val Gln Leu Ser Ser Gly
    570             575             580

AAT TCT AAT ATC CAG CAG CTC ACA CCT GTA AAT ATG CAA GGC CAG GTT    2188
Asn Ser Asn Ile Gln Gln Leu Thr Pro Val Asn Met Gln Gly Gln Val
585             590             595                 600

GTC CCT GCT AAC CAG GTT CAG AGT GGA CAT ATC AGC ACA GGC CAG CAC    2236
Val Pro Ala Asn Gln Val Gln Ser Gly His Ile Ser Thr Gly Gln His
                605             610             615

ATG ATA CAG CAA CAG ACT TTA CAA AGT ACA TCA ACT CAG CAG AGT CAA    2284
Met Ile Gln Gln Gln Thr Leu Gln Ser Thr Ser Thr Gln Gln Ser Gln
            620             625             630

CAG AGT GTA ATG AGT GGA CAC AGT CAG CAG ACG TCT CTT CCA AGT CAG    2332
Gln Ser Val Met Ser Gly His Ser Gln Gln Thr Ser Leu Pro Ser Gln
            635             640             645

ACA CCG AGC ACT CTC ACA GCC CCA CTG TAC AAT ACG ATG GTG ATT TCC    2380
Thr Pro Ser Thr Leu Thr Ala Pro Leu Tyr Asn Thr Met Val Ile Ser
650             655             660
```

Figure 8E

```
CAG CCT GCA GCT GGG AGC ATG GTC CAG ATT CCA TCC AGT ATG CCA CAG   2428
Gln Pro Ala Ala Gly Ser Met Val Gln Ile Pro Ser Ser Met Pro Gln
665             670             675             680

AAC AGT ACC CAG AGT GCT ACA GTC ACT ACG TTC ACT CAG GAC AGA CAG   2476
Asn Ser Thr Gln Ser Ala Thr Val Thr Thr Phe Thr Gln Asp Arg Gln
                685             690             695

ATA AGA TTT TCT CAA GGT CAG CAA CTT GTG ACC AAA TTA GTG ACT GCT   2524
Ile Arg Phe Ser Gln Gly Gln Gln Leu Val Thr Lys Leu Val Thr Ala
            700             705             710

CCT GTA GCT TGT GGG GCC GTC ATG GTA CCA AGT ACC ATG CTT ATG GGT   2572
Pro Val Ala Cys Gly Ala Val Met Val Pro Ser Thr Met Leu Met Gly
        715             720             725

CAG GTG GTG ACT GCC TAT CCT ACC TTC GCC ACA CAA CAG CAG CAG GCA   2620
Gln Val Val Thr Ala Tyr Pro Thr Phe Ala Thr Gln Gln Gln Gln Ala
    730             735             740

CAG ACA TTA TCG GTA ACA CAA CAG CAG CAG CAG CAG CAG CAG CAG CCA   2668
Gln Thr Leu Ser Val Thr Gln Gln Gln Gln Gln Gln Gln Gln Gln Pro
745             750             755             760

CCA CAG CAA CAG CAA CAA CAA CAG CAG AGT TCC CAG GAA CAG CAG CTT   2716
Pro Gln Gln Gln Gln Gln Gln Gln Gln Ser Ser Gln Glu Gln Gln Leu
                765             770             775

CCT TCA GTT CAG CAG CCA GCT CAG GCC CAG CTG GGC CAG CCA CCA CAG   2764
Pro Ser Val Gln Gln Pro Ala Gln Ala Gln Leu Gly Gln Pro Pro Gln
            780             785             790

CAG TTC TTA CAG ACA TCT AGG TTG CTC CAC GGG AAT CCT TCG ACA CAG   2812
Gln Phe Leu Gln Thr Ser Arg Leu Leu His Gly Asn Pro Ser Thr Gln
        795             800             805

CTC ATC CTC TCT GCT GCC TTT CCA CTA CAA CAG AGC ACT TTC CCT CCT   2860
Leu Ile Leu Ser Ala Ala Phe Pro Leu Gln Gln Ser Thr Phe Pro Pro
    810             815             820

TCG CAC CAC CAG CAA CAC CAG CCT CAG CAG CAA CAG CAG CTT CCT CGG   2908
Ser His His Gln Gln His Gln Pro Gln Gln Gln Gln Gln Leu Pro Arg
825             830             835             840

CAC AGG ACT GAC AGC CTG ACT GAC CCT TCC AAG GTC CAG CCA CAG T     2954
His Arg Thr Asp Ser Leu Thr Asp Pro Ser Lys Val Gln Pro Gln
                845             850             855
```

Figure 8F

| | | | | | | |
|---|---|---|---|---|---|---|
|AGCACACACA|CTTCCTCTCT|GACATGCGAG|AGGAAGGGGA|TGGCCAGAAA|GAATCGCTCA|3014|
|GTTGGCATGC|GGTCAGAAGT|TGAACAGTTT|CACGAGGGTG|GTCTTGAGTG|TTCAGTCCCT|3074|
|TGATGAGACG|GTAGGGAAGT|GCTGCCCAGT|GCTTCAGATG|TCCATTAAAT|ACCAGCCAGT|3134|
|GGGAAATGGT|CATAGGGACA|CAGCCAATTC|TGACAGTTTC|TTTGCCCAGG|TATTTTTTGA|3194|
|TAGAAAGAGT|ATATTGCCAA|ATGCTAACAA|GCTCAGCTAT|CAACCAGATC|TTTACTGAAT|3254|
|CCGAAGAGCA|CTAACAGTGT|TGGTAGCTTT|AGTGGGTCTG|TGCCTGCATC|AAATATTACA|3314|
|GAGGGCACAC|CACTGCCAGG|GGTTTGCTTA|GAATGCCATG|AAGATAGTCC|AGTAGTTAAT|3374|
|AGTCCCCACC|CCAAACTCCT|CTCCCTGTTC|AGACAATGAT|GGAACCGTGA|TGACTTTGAG|3434|
|AATGTTGTGC|AGGTTTGAAT|TCACTGTGTA|CAGATGCTGT|AGTGTCTCTG|TGTCTGGATG|3494|
|GAGGAGAGAA|AGCCACTTTG|ATACAGAAAG|CATTATCTGT|CCCTCACAGG|TATGAGTGCA|3554|
|TTTCATTAGG|TTTGACACCA|TGTACAAACT|GATAACAACC|TCTCTTTTTT|CATTTTGTTT|3614|
|ACAACACAGT|AGTGTTCTCG|TTACTTTTCC|AGGGCACAAG|TCTTTTTGTC|CGTGCTTTGG|3674|
|CTGTGATGTC|ACAGTTTGTT|CAGTGAGGTA|ACAATGTGCT|GCTGGGAATG|GATTTTTTTA|3734|
|AGGTTAAATT|ATTGCTACAT|TTCCACTTAC|TCAGAAATAT|CCCTTATTTC|ATTATTTTTC|3794|
|AATTATGTTT|GAGAGAATTG|CACTGCTTTA|TTATTTTAGA|TGGTTGGTTG|AGAGTTTAAT|3854|
|CACATATTTT|GATATATTTC|ATAGTTGGAA|TATTTATGTA|AATGGTTTTC|AACAAGCCTG|3914|
|AAAGTAATTT|CAAGAATGTT|TCAGTTGTAA|GAGTAAAGTT|TGCACACAAA|ACATTTTAGG|3974|
|CACTTTTTTA|ACATTCTCAG|AGGTGGGAAT|TTTAACTTTT|AGGATTTGTT|GGAATCTTTT|4034|
|TATTATCTTT|AAAAATTTCA|ATGCTTCTTT|TAGTCAGAAA|TGATTCAGGG|TTATTTGAGG|4094|
|GGAAAAAACC|CATAGTGCCT|TGATTTTAAT|TCAGGTGATA|ACTCACCATC|TTGAATTCAT|4154|
|TGTCTGGTTT|CAGTAGCAGT|TTTGAAACCT|TAGTACATTT|TTAGCAGCAG|TGTCATTCTC|4214|
|AAGTCCCCAT|GAGGACTGCT|GCGTCTCTTG|GGCTGCCTGA|CAGCGTCACA|GCTGGGAATG|4274|
|GGATCCCAAA|ATCGTTTCCT|GTTTGCATCT|TCCTCTAAAG|CTAAGTAACT|CTTTTAGGAA|4334|
|TTACCAGTAA|ATACTTGCTC|AGAGACAAGG|GACAAGTTGT|CTTTAATTTT|CATTGCAGCA|4394|
|CTAGAATAAT|GTAACTCACA|TGCTTTTTAA|ACATTAAGAT|TTCATTTGGC|AATATCATTC|4454|
|TCTACAGGTA|ATAAACTCCA|ACAAAGCTAC|ATACATTTTA|AAAGGCATTT|TTTTAGATTT|4514|
|TATGGTACTA|ATAATGAGTT|TTTCAATTAA|AGAACAAAAG|ATCAGTAGGA|TATAGAATAT|4574|
|CAAGTATTAC|TGAGAAAAGG|GAGGATAAGT|GTGGCACATT|AGAATTGACC|TTAAAAGGAA|4634|
|AGTATGTGAT|GGTGAGGTGC|TAAACTGGTT|TCAGCAGTGC|AGATAACCTA|AGGCAGAGTT|4694|
|GCTAGATCAG|GGCTTGGGGA|ACTCGGAGTC|AGCTATCTGT|CTCTAGCTTT|GCTCTCATCA|4754|
|TCAGTAAGTG|TGTCTTTGTT|TTCCTGTTTA|CCTGACTGCA|ATTAAGTTAG|CAAGTTAGTG|4814|
|ATAAAAGAA|AACAACCAAA|GAAAATTGGT|ACCTACTCTT|CTGCGTAAGA|AGTGTGTCTA|4874|
|GATACCAGTC|AGTAACTCAC|ATATCACAGA|AGTCTTCTA|GCTGACATTC|ATACGAATAC|4934|
|CAGAAATAGT|TGTGAGAATA|CACATTTATG|CAAGTTTGTG|CACACGTGAC|GAAATCAATG|4994|
|TAAGTCGAGC|ACCCACATTG|CTTTTCTCCC|TTCCACATTG|CCTTCTTCTC|TTTGGCCATT|5054|
|CCATGTCCTC|GGAGTCGGAG|CTGTGCCTCG|TTTATCTTTT|TGCATCACAT|AGCGATAAGA|5114|
|ATTTAGCTAC|AGGAGATACA|ACATGCTAGT|TATGTAATGC|CTGCTGTTCT|TCACAGTTCA|5174|
|TCTCCCTGCT|TAAAAGTAGC|AGTTGATAAG|AAACTCTAGC|TGCTAAGGCT|GCTGTCCACA|5234|
|CGGAGATGCA|TGCTGGGCAA|CAGTTGTCAG|CACTAGCTGC|CTCTTAGCTC|CTTAATTCTT|5294|
|GGTTCCTTTG|GATGGCAAAC|TGTCTTTGTC|TGCTCCCCAC|ACGACTCCAG|TATTCTGAAG|5354|
|AAAGTTCATC|TTTTGCCTGT|TCATTTCTGT|AGCCAAAGCT|GACTGAAACC|CCAAATCTAA|5414|
|ATCATGAAAA|GATACCAAAA|AGAAACACTT|CTCAGCTTCT|TAGAAACCTT|AACTTCTCTT|5474|
|GCTGTATTTC|ATGGATTTGA|TTTTCTTTGA|AATTTTTGAT|TCTGGGCAGC|GCCTTTTAAT|5534|
|TAAGAAATTG|TTAGGATGAA|GGTCAAACAG|GTTCTCATTG|CCCTGCAGGT|ACCTTGCTCT|5594|

Figure 8G

```
GGACTGCTTC TGTATGGGGT GACTTGGGGT TGCTGAACAC ACAGGATTAG AACAGTAAAC 5654
ACAAAGCTGC CCTTGAGGCT GGCGTTAAAC CAGAGCCTCA ATATTGAAAA TATCAAGTCC 5714
TCTTTCCTTC CTTAGAGACG AGACTGTGAG AGGAAAGCAA CTGTGGTAGG TGGGCTTGCT 5774
TGCACATGAG CACCAAGACC ATTCCCCAAG CTCTATCCTC AGGGTAGCAT TTAGAGTGCT 5834
GTGTTCTGCT GTCACATAGA CATGGCTTAG GGATGTAGCA CTAATAAAAG AATGCCCGTG 5894
CTTTTGAATA GTTGTGATAG CAAACTCTAG GCTAACTAGC AAGTGTTTGA ATTCTGTGTG 5954
CTGTATAGTA GTTGGTCATT GCCTTAAAGC AGTCTCTTGG AAGTTGGGAG CACTGAAGCA 6014
GTCCAACCAT ATATGGGCAT CACGTTGAGG GAGATGAGCC TTGTTCAAGC CTTAGAAAGG 6074
ACCCTTAGTC TACACAGGTA GATTCTTTTC ACTTGGATAT TACTGTGTTT AAAATGTTTC 6134
CACTATGTTG AGGCAGTTTT TTAAAGTGGA ACACAGATAG GATTTTAGT ATTTCTTTTT 6194
TTGTTTCTTT GGTGATTAAA GGTTTGTTGG TAGACATTTG TGTAAAAGTT GTTCAAGCCT 6254
ATCATCTTTC CAGTACTTGT GGTCCTGTTC TTAGTACCAG AGTCCACAAT GGAAAGTGTA 6314
AACACTGGAT ATTAATATTG CTGAGGGTGC ATAGCCAGGT GTGAGCTGAC TGGAACTTCT 6374
CAGTGGTGAA GAAACAGCAC AACGGCACTT GCCATTTCA TAGTGATTGC ATAAAGAGAC 6434
CTTCTAAGTT TGTCTGGATT GAGTGAACAC TCTTCTAAGA GGAGCTTCT AAGTAAATGC 6494
AAAGGAAAAG AGTTGACTAT TTTTATAGCA TATTTAATAT ATTTGTATAT AACTATGAGT 6554
GTAGTAGGAA CCCTCCACAT GCCTCCCACT TTTCTAATTC CCTCCCCTTC TGCCGTAGCC 6614
CTAGTCCAGC CTCATCCGCA TGGGTAATGT GCCTACTGTC AGCCTACCTA CCAAAAGATA 6674
GTGCTGCTGC TTTCTGAGAC AGGTGAGATC AGACTCTCAT GCCTGGGGAT CCTTATGGGA 6734
GGAATAGCAC ACACTTAGAA CAACATACCA CAGTTTAAGA GCATCATTTT GAAAGGTAAT 6794
AAGCACTTTA TTGCAATTAT TCATTTAGAT AAAGTTTGTA TCTTAGGCAT TAACCGTTTT 6854
TAAAGGATCC CTAATCATCA CTTAGGTGAA ATGATAAACG ACACATTTCT GAGAAATGTT 6914
CAGGTCCAGT GAACCGTAGC AGGTTTATGG GAATGATTTC AAGGTAGCCA AATAAACTCT 6974
GACTTTTGTT TTGAATGTGG TGGAGTCAGG AGATTGTAGA TGTGTAGTTT GATTTAAACA 7034
CTATTGTAAA CCTATCTTGC CTATTGTGTG GACACCAAAA GAGACCAATG AGCCTGTTTA 7094
TTTTCAGAGG TCTAGGAATA TGCATCTGTC TGAGTAGATA TACAGAACTA ATCTATAAAC 7154
GGTTGGTAGT AATATTTTAG GATACAGTAA CTTAAAGAAT TATTGAGTGT TTTAAATGTG 7214
CCCTGAAATG TTGGCATGTC ATTTCAGCGT TCCCATTTGA GTTGCTCTTG TAATATTTTT 7274
GCACAAAAAG GACTGAGAAA AGACTGCTTT GGTTGAAGAA AACTATAATT TGGTCTTATT 7334
TTAATGTCTC CTGTGGAAAC ACTGGAGGTA AATTTGTTGG CATAGTTACT AATTCAGGAT 7394
ATTTAAAACA GTGTTGAACA GCTCATCAGA AATTAAGCAA ACTTATATAT TTAAAAATTA 7454
AAAATCTTTT TTTCCATGTG ACTGAAAAAA AAAAAAAAAA AAAA           7498
```

Fig 9-1

Exon 1a 71bp (SEQ ID NO: 3)

GCTGGAGAGAGGAAACCCCGGACGGCGAGAGCGCGAAGGAAATCTGGCCGCCCGCC
GCGCACGCGCTCCCG

Exon 1b 181bp (pos 1-181 in SEQ ID NO: 1)

GGGGAGGAGCGCGGCGGTAGCGGTGAATTTTGAGGGGTGGGTCGGGGGCGCGCACT
CGCCGCCCCTGGTGCTGCCGGCTCCCGGAGCCGTGGCGTGTCCCTGCTGTCGCCGCTC
GGCTGTCGCGAGCCGCCGCGGGCAGAGTCCCGGGCGGGGGAGGGAGGAAGCCGGA
GCCTCAGGCACG

Exon 2 79bp (pos 182-260 in SEQ ID NO: 1)

TGAAAGAAAAGCACAAGAAGAAACTTTTACAGGCGTTGTTGATTGGACTAGGCAAC
GATTCCCAAAATCACCAGCAAG

Exon 3 85bp (pos 261-345 in SEQ ID NO: 1)

AGTTCTGATGGTCAGTCACACAGAAGACGGCCTTGCGTCTGTGGGTGTTGGAGACTC
CATTCTAAAGATATAAAAAGTGAAAGAG

Exon 4 90bp (pos 346-435 in SEQ ID NO: 1)

GAGAAGTACAAATGTCTACCACAAGACGAAAACATAATGTGTTATGGTGTTTACCGT
AAGCTGTAGTAAAATGAGCTCAATTGTTGACAG

Exon 5 60bp (pos 436-495 in SEQ ID NO: 1)

AGATGACAGTAGTATTTTTGATGGATTGGTGGAAGAAGATGACAAGGAACAAAGCA
AAAAG

Exon 6 149bp (pos 496-644 in SEQ ID NO:1)

AGTATCTAGAAACAAATCAGAAAAGAAACGTAGAGATCAGTTCAATGTCCTCATTAA
GGAGCTGGGGTCTATGCTTCCTGGTAACGCGAGAAAGATGGACAAGTCTACTGTTCT
ACAGAAGAGCATTGATTTTTTGCGCAAACATAAAG

Exon 7 92bp (pos 645-736 in SEQ ID NO: 1)

AGACCACTGCACAGTCAGATGCTAGTGAGATTCGACAGGACTGGAAACCCACATTCC
TTAGTAATGAAGAGTTTACACAGTTAATGTTAGAG

Exon 8 90bp (pos 737-826 in SEQ ID NO: 1)

GCTCTTGATGGTTTTTTTTTAGCGATCATGACAGATGGAAGTATAATATATGTATCTG
AGAGTGTAACTTCGTTACTTGAACATTTACCA

Fig. 9-2

Exon 9 121bp (pos 827-947 in SEQ ID NO: 1)

TCTGATCTTGTGGATCAAAGTATATTTAATTTTATCCCAGAGGGAGAACATTCAGAG
GTTTATAAGATACTCTCTACTCATCTGCTGGAAAGTGACTCATTAACCCCTGAGTACT
TAAAAT

Exon 10 114bp (pos 948-1061 in SEQ ID NO:1)

CAAAAAATCAGTTAGAATTCTGTTGTCACATGCTTCGAGGAACAATAGACCCAAAGG
AGCCATCCACCTATGAATATGTGAGATTTATAGGAAATTTTAAATCTTTAACCAGTG

Exon 11 119bp (pos 1062-1180 in SEQ ID NO: 1)

TATCAACTTCAACACACAATGGTTTTGAAGGAACTATACAACGCACACATAGGCCTT
CTTATGAAGATAGAGTTTGTTTTGTAGCTACTGTCAGATTAGCTACACCTCAGTTCAT
CAAG

Exon 12 83bp (pos 1181-1263 IN SEQ ID NO: 1)

GAAATGTGTACTGTTGAAGAACCAAATGAAGAGTTTACATCTAGACACAGTTTAGAA
TGGAAGTTTCTATTTTTAGATCACAG

Exon 13 107bp (pos 1264-1370 in SEQ ID NO: 1)

GGCACCACCAATAATAGGCTATTTGCCATTTGAAGTCTTGGGAACATCAGGCTATGA
TTACTATCATGTGGATGACCTAGAAAATCTGGCAAAATGTCACGAGCACT

Exon 14 148bp (pos 1371-1518 in SEQ ID NO: 1)

TAATGCAATATGGAAAAGGCAAATCGTGTTACTATAGATTCCTGACCAAAGGCCAGC
AGTGGATATGGCTTCAGACTCATTATTATATTACTTACCATCAGTGGAATTCAAGGCC
AGAGTTCATTGTTTGTACTCACACTGTAGTAAG

Exon 15 76bp (pos 1519-1594 in SEQ ID NO: 1)

TTATGCAGAAGTTAGGGCTGAAAGACGGCGAGAACTTGGCATTGAAGAGTCTCTTCC
TGAGACAGCTGCTGACAAA

Exon 16 142bp (pos 1595-1736 in SEQ ID NO: 1)

AGCCAAGATTCTGGGTCTGACAATCGTATCAACACAGTGAGTCTCAAGGAAGCACTG
GAAAGGTTTGATCACAGCCCAACTCCTTCTGCCTCCTCTAGAAGCTCACGAAAGTCA
TCTCACACCGCAGTCTCAGACCCTTCCT

Fig. 9-3

Exon 17 101bp (pos 1737-1837 in SEQ ID NO: 1)

CCACACCGACAAAGATCCCTACTGATACTAGCACTCCTCCCAGACAGCATTTGCCAG
CTCATGAAAAGATGACACAGCGGAGGTCGTCCTTCAGCAGTCAG

Exon 18 90bp (pos 1838-1927 in SEQ ID NO: 1)

TCCATAAACTCCCAGTCAGTTGGTCCATCATTAACACAGCCAGCGATGTCTCAAGCT
GCAAATTTACCAATTCCACAAGGCATGTCACAG

Exon 19 153bp (pos 1928-2080 in SEQ ID NO: 1)

TTTCAGTTTCAGCTCAGTTAGGAGCCATGCAGCATCTAAAAGACCAGCTAGAGCAGC
GGACACGGATGATAGAGGCAAATATTCATCGGCAGCAAGAAGAACTAAGGAAAATT
CAAGAGCAACTTCAGATGGTCCATGGTCAAGGGCTACAG

Exon 20 195bp (pos 2081-2275 in SEQ ID NO: 1)

ATGTTTTTGCAGCAATCAAACCCTGGATTGAATTTTGGTTCTGTTCAACTTTCCTCTG
GAAATTCTAATATCCAGCAGCTCACACCTGTAAATATGCAAGGCCAGGTTGTCCCTG
CTAACCAGGTTCAGAGTGGACATATCAGCACAGGCCAGCACATGATACAGCAACAG
ACTTTACAAAGTACATCAACTCAG

Exon 21 206bp (pos 2276-2481 in SEQ ID NO: 1)

CAGAGTCAACAGAGTGTAATGAGTGGACACAGTCAGCAGACGTCTCTTCCAAGTCAG
ACACCGAGCACTCTCACAGCCCCACTGTACAATACGATGGTGATTTCCCAGCCTGCA
GCTGGGAGCATGGTCCAGATTCCATCCAGTATGCCACAGAACAGTACCCAGAGTGCT
ACAGTCACTACGTTCACTCAGGACAGACAGATAAG

Exon 22 295bp (pos 2482-2776 in SEQ ID NO: 1)

ATTTTCTCAAGGTCAGCAACTTGTGACCAAATTAGTGACTGCTCCTGTAGCTTGTGGG
GCCGTCATGGTACCAAGTACCATGCTTATGGGTCAGGTGGTGACTGCCTATCCTACCT
TCGCCACACAACAGCAGCAAGGACAGACATTATCGGTAACACAACAGCAGCAGCAG
CAGCAGCAGCAGCAGCCACCACAGCAACAGCAACAACAACAGCAGAGTTCCCAGGA
ACAGCAGCTTCCTTCAGTTCAGCAGCCAGCTCAGGCCCAGCTGGGCCAGCCACCACA
GCAGTTCTTACAG

Exon 23 4722bp End of Coding and 3UTR (pos 2777-7498 in SEQ ID NO: 1)

ACATCTAGGTTGCTCCACGGGAATCCTTCGACACAGCTCATCCTCTCTGCTGCCTTTC
CACTACAACAGAGCACTTTCCCTCCTTCGCACCACCAGCAACACCAGCCTCAGCAGC
AACAGCAGCTTCCTCGGCACAGGACTGACAGCCTGACTGACCCTTCCAAGGTCCAGC
CACAGTAGCACACACACTTCCTCTCTGACATGCGAGAGGAAGGGGATGGCCAGAAA
GAATCGCTCAGTTGGCATGCGGTCAGAAGTTGAACAGTTTCACGAGGGTGGTCTTGA
GTGTTCAGTCCCTTGATGAGACGGTAGGGAAGTGCTGCCCAGTGCTTCAGATGTCCA
TTAAATACCAGCCAGTGGGAAATGGTCATAGGGACACAGCCAATTCTGACAGTTTCT

Fig. 9-4

```
TTGCCCAGGTATTTTTTGATAGAAAGAGTATATTGCCAAATGCTAACAAGCTCAGCT
ATCAACCAGATCTTTACTGAATCCGAAGAGCACTAACAGTGTTGGTAGCTTTAGTGG
GTCTGTGCCTGCATCAAATATTACAGAGGGCACACCACTGCCAGGGGTTTGCTTAGA
ATGCCATGAAGATAGTCCAGTAGTTAATAGTCCCCACCCCAAACTCCTCTCCCTGTTC
AGACAATGATGGAACCGTGATGACTTTGAGAATGTTGTGCAGGTTTGAATTCACTGT
GTACAGATGCTGTAGTGTCTCTGTGTCTGGATGGAGGAGAGAAAGCCACTTTGATAC
AGAAAAGCATTATCTGTCCCTCACAGGTATGAGTGCATTTCATTAGGTTTGACACCAT
GTACAAACTGATAACAACCTCTCTTTTTTCATTTTGTTTACAACACAGTAGTGTTCTC
GTTACTTTTCCAGGGCACAAGTCTTTTTGTCCGTGCTTTGGCTGTGATGTCACAGTTT
GTTCAGTGAGGTAACAATGTGCTGCTGGGAATGGATTTTTTTAAGGTTAAATTATTGC
TACATTTCCACTTACTCAGAAATATCCCTTATTTCATTATTTTTCAATTATGTTTGAGA
GAATTGCACTGCTTTATTATTTTAGATGGTTGGTTGAGAGTTTAATCACATATTTTGA
TATATTTCATAGTTGGAATATTTATGTAAATGGTTTTCAACAAGCCTGAAAGTAATTT
CAAGAATGTTTCAGTTGTAAGAGTAAAGTTTGCACACAAAACATTTTAGGCACTTTTT
TAACATTCTCAGAGGTGGGAATTTTAACTTTTAGGATTTGTTGGAATCTTTTTATTATC
TTTAAAAATTTCAATGCTTCTTTTAGTCAGAAATGATTCAGGGTTATTTGAGGGGAAA
AAACCCATAGTGCCTTGATTTTAATTCAGGTGATAACTCACCATCTTGAATTCATTGT
CTGGTTTCAGTAGCAGTTTTGAAACCTTAGTACATTTTTAGCAGCAGTGTCATTCTCA
AGTCCCCATGAGGACTGCTGCGTCTCTTGGGCTGCCTGACAGCGTCACAGCTGGGAA
TGGGATCCCAAAATCGTTTCCTGTTTGCATCTTCCTCTAAAGCTAAGTAACTCTTTTA
GGAATTACCAGTAAATACTTGCTCAGAGACAAGGGACAAGTTGTCTTTAATTTTCAT
TGCAGCACTAGAATAATGTAACTCACATGCTTTTTAAACATTAAGATTTCATTTGGCA
ATATCATTCTCTACAGGTAATAAACTCCAACAAAGCTACATACATTTTAAAAGGCAT
TTTTTTAGATTTTATGGTACTAATAATGAGTTTTTCAATTAAAGAACAAAAGATCAGT
AGGATATAGAATATCAAGTATTACTGAGAAAAGGGAGGATAAGTGTGGCACATTAG
AATTGACCTTAAAAGGAAAGTATGTGATGGTGAGGTGCTAAACTGGTTTCAGCAGTG
CAGATAACCTAAGGCAGAGTTGCTAGACAGGGCTTGGGGAACTCGGAGTCAGCTAT
CTGTCTCTAGCTTTGCTCTCATCATCAGTAAGTGTGTCTTTGTTTTCCTGTTTACCTGA
CTGCAATTAAGTTAGCAAGTTAGTGATAAAAAGAAAACAACCAAAGAAAATTGGTA
CCTACTCTTCTGCRTAAGAAGTGTGTCTAGATACCAGTCAGTAACTCACATATCACAG
AAGTTCTTCTAGCTGACATTCATACGAATACCAGAAATAGTTGTGAGAATACACATT
TATGCAAGTTTGTGCACACGTGACGAAATCAATGTAAGTCGAGCACCCACATTGCTT
TTCTCCCTTCCACATTGCCTTCTTCTCTTTGGCCATTCCATGTCCTCGGAGTCGGARCT
GTGCCTCGTTTATCTTTTTGCATCACATAGCGATAACAATTTAGCTACAGGAGATACA
ACATGCTAGTTATGTAATGCCTGCTGTTCTTCACAGTTCATCTCCCTGCTTAAAAGTA
GCAGTTGATAAGAAACTCTAGCTGCTAAGGCTGCTGTCCACACGGAGATGCATGCTG
GGCAACAGTTGTCAGCACTAGCTGCCTCTTAGCTCCTTAATTCTTGGTTCCTTTGGAT
GGCAAACTGTCTTTGTCTGCTCCCCACACGACTCCAGTATTCTGAAGAAAGTTCATCT
TTTGCCTGTTCATTTCTGTAGCCAAAGCTGACTGAAACCCCAAATCTAAATCATGAAA
AGATACCAAAAGAAACACTTCTCAGCTTCTTAGAAACCTTAACTTCTCTTGCTGTAT
TTCATGGATTTGATTTTCTTTGAAATTTTTGATTCTGGGCAGCGCCTTTTAATTAAGAA
ATTGTTAGGATGAAGGTCAAACAGGTTCTCATTGCCCTGCAGGTACCTTGCTCTGGA
CTGCTTCTGTATGGGGTGACTTGGGGTTGCTGAACACACAGGATTAGAACAGTAAAC
ACAAAGCTGCCCTTGAGGCTGGCGTTAAACCAGAGCCTCAATATTGAAAATATCAAG
TCCTCTTTCCTTCCTTAGAGACGAGACTGTGAGAGGAAAGCAACTGTGGTAGGTGGG
CTTGCTTGCACATGAGCACCAAGACCATTCCCCAAGCTCTATCCTCAGGGTAGCATTT
AGAGTGCTGTGTTCTGCTGTCACATAGACATGGCTTAGGGATGTAGCACTAATAAAA
```

Fig 9-5

GAATGCCCGTGCTTTTGAATAGTTGTGATAGCAAACTCTAGGCTAACTAGCAAGTGT
TTGAATTCTGTGTGCTGTATAGTAGTTGGTCATTGCCTTAAAGCAGTCTCTTGGAAGT
TGGGAGCACTGAAGCAGTCCAACCATATATGGGCATCACGTTGAGGGAGATGAGCC
TTGTTCAAGCCTTAGAAAGGACCCTTAGTCTACACAGGTAGATTCTTTTCACTTGGAT
ATTACTGTGTTTAAAATGTTTCCACTATGTTGAGGCAGTTTTTTAAAGTGGAACACAG
ATAGGATTTTTAGTATTTCTTTTTTTGTTTCTTTGGTGATTAAAGGTTTGTTGGTAGAC
ATTTGTGTAAAAGTTGTTCAAGCCTATCATCTTTCCAGTACTTGTGGTCCTGTTCTTAG
TACCAGAGTCCACAATGGAAAGTGTAAACACTGGATATTAATATTGCTGAGGGTGCA
TAGCCAGGTGTGAGCTGACTGGAACTTCTCAGTGGTGAAGAAACAGCACAACGGCA
CTTGCCATTTTCATAGTGATTGCATAAAGAGACCTTCTAAGTTTGTCTGGATTGAGTG
AACACTCTTCTAAGAGGAGCTTCTCAAGTAAATGCAAAGGAAAAGAGTTGACTATTT
TTATAGCATATTTAATATATTTGTATATAACTATGAGTGTAGTAGGAACCCTCCACAT
GCCTCCCACTTTTCTAATTCCCTCCCCTTCTGCCGTAGCCCTAGTCCAGCCTCATCCGC
ATGGGTAATGTGCCTACTGTCAGCCTACCTACCAAAAGATAGTGCTGCTGCTTTCTGA
GACAGGTGAGATCAGACTCTCATGCCTGGGGATCCTTATGGGAGGAATAGCACACAC
TTAGAACAACATACCACAGTTTAAGAGCATCATTTTGAAAGGTAATAAGCACTTTAT
TGCAATTATTCATTTAGATAAAGTTTGTATCTTAGGCATTAACCGTTTTAAAGGATC
CCTAATCATCACTTAGGTGAAATCATAAACGACACATTTCTGAGAAATGTTCAGGTC
CAGTGAACCGTAGCAGGTTTATGGGAATGATTTCAAGGTAGCCAAATAAACTCTGAC
TTTTGTTTTGAATGTGGTGGAGTCAGGAGATTGTAGATGTGTAGTTTGATTTAAACAC
TATTGTAAACCTATCTTGCCTATTGTGTGGACACCAAAAGAGACCAATGAGCCTGTTT
ATTTTCAGAGGTCTAGGAATATGCATCTGTCTGAGTAGATATACAGAACTAATCTAT
AAACGGTTGGTAGTAATATTTTAGGATACAGTAACTTAAAGAATTATTGAGTGTTTTA
AATGTGCCCTGAAATGTTGGCATGTCATTTCAGCGTTCCCATTTGAGTTGCTCTTGTA
ATATTTTGCACAAAAAGGACTGAGAAAAGACTGCTTTGGTTGAAGAAAACTATAAT
TTGGTCTTATTTTAATGTCTCCTGTGGAAACACTGGAGGTAAATTTGTTGGCATAGTT
ACTAATTCAGGATATTTAAAACAGTGTTGAACAGCTCATCAGAAATTAAGCAAACTT
ATATATTTAAAAATTAAAAATCTTTTTTTCCATGTGACTG

Fig. 10

| SEQ ID NO. | Exon # | Exon Size | ....EXON/INTRON...... | Intron size | ......INTRON/EXON.......... | Exon # | SEQ ID NO |
|---|---|---|---|---|---|---|---|
| 4 | 1a | 71 | GCGCTCCCGgtgagtgcg | 0.9kb | tctggtgtttcttattgcagTGAAAGAAA | 2 | 27 |
| 5 | 1b | 189 | TCAGGCACGgtgaggacg | >22kb | cttttgttttttaaaacagAGTTCTGAT | 3 | 28 |
| 6 | 2 | 79 | ACCAGCAAGgtaatttcc | 7.0kb | atgttttctttctcacaagGAGAAGTAC | 4 | 29 |
| 7 | 3 | 85 | GTGAAAGAGgtaaaggcg | 0.4kb | ctctgtcttttctcttagAGATGACAG | 5 | 30 |
| 8 | 4 | 90 | TGTTGACAGgtatgtttt | 0.4kb | taatttcttttcttcatagAGTATCTAG | 6 | 31 |
| 9 | 5 | 60 | AGCAAAAAGgtagttagc | 3.0kb | acgtcaatcgttacagAGACCACTG | 7 | 32 |
| 10 | 6 | 149 | AACATAAAGgtaaagtgc | 8.2kb | accattatgtttaatttcagGCTCTTGAT | 8 | 33 |
| 11 | 7 | 92 | ATGTTAGAGgtatgtca | 5.9kb | tttttttatttcagTCTGATCTT | 9 | 34 |
| 12 | 8 | 90 | CATTTACCAgtaagtatg | 2.8kb | cttttatcacttattccagCAAAAAATC | 10 | 35 |
| 13 | 9 | 121 | ACTTAAAATgtaagtagg | 0.1kb | atgtcctgctgtttagTATCAACTT | 11 | 36 |
| 14 | 10 | 114 | TAACCAGTGgtaagtaa | 2.0kb | actgtaattgtttgtagGAAATGTGT | 12 | 37 |
| 15 | 11 | 119 | TTCATCAAGgtatgcttc | 0.2kb | atattactgataatttagGGCACCACC | 13 | 38 |
| 16 | 12 | 83 | AGATCACAGgtaacatta | 0.8kb | ttttattttattttagTAATGCAAT | 14 | 39 |
| 17 | 13 | 107 | ACGAGCACTgtaagtagc | 0.9kb | ttggttcttccattgtagTTATTGCAG | 15 | 40 |
| 18 | 14 | 148 | TGTAGTAAGgtaataact | 3.7kb | tgttcctctatcctcttagAGCCAAGAT | 16 | 41 |
| 19 | 15 | 76 | GCTGACAAAgtatgtttc | 0.6kb | tctcgtgactgtcttagCCACACCGA | 17 | 42 |
| 20 | 16 | 142 | ACCCTTCCTgtgagtgcc | 0.4kb | atctttattgctctagTCCATAAAC | 18 | 43 |
| 21 | 17 | 101 | AGCAGTCAGgtacgcctt | 4.2kb | ctttccatgctgctcttcagTTTCAGTTT | 19 | 44 |
| 22 | 18* | 90 | ATGTCACAGgtattttg | 1.0kb | tgtgatctttgtttcaaagATGTTTTTG | 20 | 45 |
| 23 | 19 | 153 | GGGCTACAGgtaacttat | 0.6kb | ttccatacgatctttctagCAGAGTCAA | 21 | 46 |
| 24 | 20 | 195 | TCAACTCAGgtaattgac | 2.1kb | tatttgtttctctcacagATTTTCTCA | 22 | 47 |
| 25 | 21 | 206 | ACAGATAAGgtagttgtc | >9.2kb | atcatcctttgttttagACATCTAGG | 23 | 48 |
| 26 | 22 | 295 | TTCTTACAGgtaaccccc | | | | |
| | | | donor splice seq | | | | |
| | | | | | | | |
| | 19 | 153 | GGGCTACAGgtaacttat | | Wild type (SEQ ID NO: 49) | | |
| | 19 | 153 | GGGCTACAGgttacttat | | Clock Mutant (SEQ ID NO: 50) | | |

* Alternatively spliced in wild-type

```
                                                      bHLH domain
MVFTVSCSKMSSIVDRDDSS  IFDGLVEEDDKDKA KRVSRN  KSEKKRRDQFNVLIKELGSM    60
LPGNARKMDKSTVLQKSIDF  L RKHKETTAQSDASEIRQDW  KPTFLSNEEFTQLM LEALDG   120
            PAS A
FFLAIMTDGSIIYVSESVTS  LLEHLPSDLVDQSIFNFIPE  GEH SEVYKILSTHLLESDSL   180
TPEYLKSKNQLEFCCHMLRG  TIDPKEPSTYEYVRFIGNFK  SLTSVSTSTHNGFEGTIQRT    240
                                      PAS B
HRPSYEDRVCFVATVRLATP  QFIKEMCTVEF PNEEFTSRH  SLEWKFLFLDHRAPPIIGYL    300
PFEVLGTSGYDYYHVDDL EN LAKCHEHLMQYGKGKSCYYR  FLTKGQQWIWLQTHYYITYH    360
QWNSRPEFIVCTHTVVSYAE  VRAERRRELGIEESLPETAA  DKSQDSGSDNRINTVSLKEA    420
LERFDHSPTPSASSRSSRKS  SHTAVSDPSSTPTKIPTDTS  TPPRQHLPAHEKMTQRRSSF    480
                                           Deleted in Mutant
SSQSINSQSVGPSLTQPAMS  QAANLPIPQGMSQ FQFSAQL  GAMQHLKDQLEQRTRMIEAN    540
IHRQQEELRKIQEQLQMVHG  QGLQ MFLQQSNPGLNFGSVQ  LSSGNSNIQQLTPVNMQGQV    600
VPANQVQSGHISTGQHMIQQ  QTLQSTSTQQSQQSVMSGHS  QQTSLPSQTPSTLTAPLYNT    660
MVISQPAAGSMVQIPSSMPQ  NSTQSATVTTFTQDRQIRFS  QGQQLVTKLVTAPVACGAVM    720
VPSTMLMGQVVTAYPTFATQ  QQQAQTLSVTQQQQQQQQP   PQQQQQQQSSQEQQLPSVQ     780
QPAQAQLGQPPQQFLQTSRL  LHGNPSTQLILSAAFPLQQS  TFPPSHHQQHQPQQQQQLPR    840
HRTDSLTDPSKVQPQ                                                    855
```

FIG. 13

```
                                          ┌────────bHLH domain──────────────┐
MVFTVSCSKMSSIVDRDDSS  IFDGLVEEDDKDKA│KRVSRN  KSEKKRRDQFNVLIKELGSM│  60
┌──────────────────────────────────┐│                             │
│LPGNARKMDKSTVLQKSIDF  L│RKHKETTAQSDASEIRQDW  KPTFLSNEEFTQLM│LEALDG│ 120
      PAS A           └─                                    └─
┌──────────────────────────────────────────────────────────────┐
│FFLAIMTDGSIIYVSESVTS  LLEHLPSDLVDQSIFNFIPE  GEH│SEVYKILSTHLLESDSL  180
└─────────────────────────────────────────────┘
TPEYLKSKNQLEFCCHMLRG  TIDPKEPSTYEYVRFIGNFK  SLTSVSTSTHNGFEGTIQRT  240
                                                  ┌──PAS B─────────────────┐
HRPSYEDRVCFVATVRLATP  QFIKEMCTVEE│PNEEFTSRH  SLEWKFLFLDHRAPPIIGYL│  300
┌──────────────────────┐
│PFEVLGTSGYDYYHVDDL│EN  LAKCHEHLMQYGKGKSCYYR  FLTKGQQWIWLQTHYYITYH  360
└─────────────────┘
QWNSRPEFIVCTHTVVSYAE  VRAERRRELGIEESLPETAA  DKSQDSGSDNRINTVSLKEA  420

LERFDHSPTPSASSRSSRKS  SHTAVSDPSSTPTKIPTDTS  TPPRQHLPAHEKMTQRRSSF  480
       ▼ exon 18 (30 aa) spliced out    ╲Deleted in Mutant
SSQ│FQFSAQLGAMQHLKDQL  EQRTRMIEANIHRQQEELRK  IQEQLQMVHGQGLQ│MFLQQS  540

NPGLNFGSVQLSSGNSNIQQ  LTPVNMQGQVVPANQVQSGH  ISTGQHMIQQQTLQSTSTQQ  600

SQQSVMSGHSQQTSLPSQTP  STLTAPLYNTMVISQPAAGS  MVQIPSSMPQNSTQSATVTT  660

FTQDRQIRFSQGQQLVTKLV  TAPVACGAVMVPSTMLMGQV  VTAYPTFATQQQQAQTLSVT  720

QQQQQQQQQPPQQQQQQQQS  SQEQQLPSVQQPAQAQLGQP  PQQFLQTSRLLHGNPSTQLI  780

LSAAFPLQQSTFPPSHHQQH  QPQQQQQLPRHRTDSLTDPS  KVQPQ                 825
```

CLOCK GENE AND GENE PRODUCT

TECHNICAL FIELD OF THE INVENTION

The field of the present invention is the circadian clock of mammals. More particularly, the present invention relates to mammalian genes and gene products that regulate aspects of the circadian rhythm in mammals and those processes controlled by the circadian rhythm.

BACKGROUND OF THE INVENTION

Circadian rhythms are a fundamental property of all eukaryotic and some prokaryotic organisms (Takahashi 1995). The underlying molecular mechanism appears similar among living systems, is cell autonomous and involves periodic macromolecular synthesis. Alterations in circadian rhythms are involved in sleep disorders such as "delayed sleep phase syndrome" which may be an alteration in the circadian period (lengthening) and the entrainment system. There is also evidence for circadian rhythm abnormalities in affective disorders. The most consistent feature of circadian rhythms observed in depressed patients is that a variety of physiological events occur earlier than normal (usually referred to as a "phase advance"). A shortened REM latency after sleep onset, which can be the manifestation of a change in the circadian coupling or organization of rhythms, appears to be a prominent characteristic of depression.

Further, a number of diagnostic tests depend on the time of day at which the test is performed. These include the dexamethasone suppression test for depression, intraocular pressure measurements for glaucoma, and plasma cortisol concentration for Addison's disease and Cushing's syndrome. In addition, a number of clinical treatments (such as chemotherapy or alleviation of hypertension) can be optimized through the delivery of therapeutic agents at the appropriate time of day. Circadian rhythmicity appears to be deeply embedded in most aspects of the biology of organisms—indeed it is a central feature of their organization. It seems unlikely that complete understanding of most regulatory processes can be achieved without an appreciation of their circadian dimensions.

Clock genes have been described in other model systems, most notably in Drosophila and Neurospora. Three known clock genes have been characterized at the molecular and functional level. These are the period (per) and timeless (tim) genes in Drosophila, and the frequency (frq) gene in Neurospora. This work is known to the art and is described in review papers by J. S. Takahashi, *Annual Review of Neuroscience* 18:531–553, 1995; and by J. C. Dunlap, *Annual Review of Genetics* 30:579–601, 1996. None of these three clock genes have been shown to possess a protein motif known to allow these proteins to bind DNA, rather it appears that in the case of PERIOD and TIMELESS, these proteins must interact with unidentified DNA-binding transcription factors.

The genetic approach to circadian rhythms was first described by Ron Konopka and Seymour Benzer (1971) who isolated single-gene mutations that altered circadian periodicity in Drosophila. In a chemical mutagenesis screen of the X chromosome, they found three mutants that either shortened ($per^S$), lengthened ($per^L$) or abolished ($per^0$) circadian rhythms of eclosion and adult locomotor activity. In 1984, two groups at Brandeis and Rockefeller independently cloned per in a series of experiments that showed that germline transformation with DNA could rescue a complex behavioral program (reviewed in Rosbash & Hall 1989). Each of the mutant per alleles is caused by intragenic point mutations that produce missense mutations in $per^S$ and $per^L$ and a nonsense mutation in $per^0$ (Bayfies et al. 1987, Yu et al. 1987). Only recently has the nature of per gene product (PER) become more clear. The Drosophila single-minded protein (SIM) (Nambu et al. 1991), the human aryl hydrocarbon receptor nuclear translocator (ARNT) (Hoffirian et al. 1991), and the aryl hydrocarbon receptor (AHR) (Burbach et al. 1992) all share with PER a domain called PAS (for PER, ARNT, SIM) (Nambu et al. 1991). The PAS domain contains about 270 amino acids of sequence similarity with two 51-amino acid direct repeats. Recent work shows that the PAS domain can function as a dimerization domain (Huang et al. 1993). Because other PAS members are transcriptional regulators and PER can dimerize to them, PER could function as a transcriptional regulator either by working in concert with a partner that carries a DNA-binding domain, or by acting as a dominant-negative regulator by competing with a transcriptional regulator for dimenization or DNA binding. Consistent with this role, PER is predominantly a nuclear protein in the adult central nervous system of Drosophila (Liu et al. 1992).

The expression of PER itself is circadian, and both per mRNA and PER protein abundance levels oscillate. Hardin et al. (1990) showed that per mRNA levels undergo a striking circadian oscillation. The per RNA rhythm persists in constant darkness and the period of the RNA rhythm is ~24 hours in $per^+$ flies and is ~20 hours in $per^S$ flies. The RNA of $per^0$ flies is present at a level ~50% of normal flies, but does not oscillate. In $per^0$ flies that have been rescued by germline transformation with wild-type $per^+$ DNA, both circadian behavior and per RNA cycles are restored. Importantly, in these transformed flies both the exogenous $per^+$ RNA and the endogenous $per^0$ RNA levels oscillate. In addition to a per RNA cycle, the PER protein also shows a circadian rhythm in abundance (Siwicki et al. 1988, Zerr et al. 1990, Edery et al. 1994b). The rhythm in PER protein also depends on per, because $per^0$ flies do not have a protein rhythm and because per mutants alter the PER rhythm (Zerr et al. 1990). Therefore, the circadian expression of per mRNA and protein levels both depend on an active per gene. Because $per^S$ shortens the period of the RNA cycle and because $per^+$ DNA transformation rescues $per^0$ RNA cycling, PER protein expression clearly regulates per RNA cycling. Hardin et al. (1990) propose that feedback of the per gene product regulates its own mRNA levels. Support for such a model has been provided by showing that transient induction of PER from a heat shock promoter/per cDNA transgene in a wild-type background can phase shift circadian activity rhythms in Drosophila (Edery et al. 1994a).

The PER protein rhythm appears to be regulated at both transcriptional and post-transcriptional levels. Hardin et al. (1992) have shown that levels of per precursor RNA cycle in concert with mature per transcripts. In addition, per promoter/CAT fusion gene constructs show that per 5' flanking sequences are sufficient to drive heterologous RNA cycles. These results suggest that circadian fluctuations in per mRNA abundance are controlled at the transcriptional level. In addition to a rhythm in per transcription and PER abundance, PER appears to undergo multiple phosphorylation events as it accumulates each cycle (Edery et al. 1994b). The nature and functional significance of the PER phosphorylation sites, however, are not known at this time. Interestingly, the peak of the per RNA cycle precedes the peak of the PER protein cycle by about 4–6 hours. The reasons for the lag in PER accumulation are not well understood. However, the recent isolation of a second clock mutant, named timeless (tim), has provided significant insight (Sehgal et al. 1994). Tim mutants fail to express circadian rhythms in eclosion and locomotor activity, but more importantly also fail to express circadian rhythms in per mRNA abundance (Sehgal et al. 1994). Furthermore, the nuclear localization of PER is blocked in tim mutants (Vosshall et al. 1994). In 1995, tim was cloned by positional cloning and by interaction with the PAS domain of PER in a yeast two-hybrid screen (Gekakis et al. 1995, Myers et al. 1995). Like PER, TIM is a large protein without any obvious sequence homologies to other proteins. While PER dimerizes to TIM via the PAS domain, TIM is not a member of the PAS family. The expression of tim RNA levels has a striking circadian oscillation which is in phase with the per RNA rhythm. The rhythm in tim RNA levels depends on PER and is abolished in $per^O$ mutants and shortened in $per^S$ mutants. Thus, per and tim express a coordinate circadian rhythm that is interdependent. TIM protein also shows a circadian rhythm with a phase similar to that of PER. Formation of a PER/TIM heterodimer appears to be required for nuclear entry of the complex. In the last year, four different laboratories discovered that light exposure causes a rapid degradation of TIM protein in flies and this action of light can explain how entrainment of the circadian clock in Drosophila occurs (Hunter-Ensor et al. 1996, Lee et al. 1996, Myers et al. 1996, Zeng et al. 1996). Thus, the identification of tim and its functional interaction with per is important because it suggests that elements of a transcription-translation-nuclear transport feedback loop are central elements of the circadian mechanism in Drosophila.

In addition to the Drosophila per and tim genes, progress has been made in elucidating the molecular nature of the Neurospora frequency (frq) gene (Dunlap 1993). Like per, the frq locus is defined by mutant alleles that either shorten, lengthen or disrupt circadian rhythms (Feldman & Hoyle 1973, Feldman 1982, Dunlap 1993). Cloned in 1989, the sequence of FRQ shows little resemblance to PER (except for a region containing threonine-glycine repeats) (McClung et al. 1989); however, recent molecular work shows striking functional similarities (Aronson et al. 1994). The frq gene expresses a circadian oscillation of mRNA abundance whose period is altered by frq mutations (Aronson et al. 1994). A null allele, $frq^9$, expresses elevated levels of frq transcript and does not show a rhythm in mRNA abundance (Aronson et al. 1994). Interestingly, no level of constitutive expression off $frq^+$ in a null background can rescue overt rhthmicity, which suggests that the circadian rhythm of frq mRNA is a necessary component of the oscillator (Aronson et al. 1994). However, overexpression of a $frq^+$ transgene does negatively autoregulate expression of the endogenous of a frq gene (Aronson et al. 1994). In addition, overexpression of $frg^+$ transgene in a wild-type background blocks overt expression of circadian rhythms (Aronson et al. 1994). The phase of the overt circadian rhythm can be determined by a step reduction in FRQ protein expression (Aronson et al. 1994). Taken together, these experiments show that frq is likely a central component of the Neurospora circadian oscillator and that a negative autoregulatory loop regulating frq transcription forms the basis of the oscillation (Aronson et al. 1994). Recently a direct action of light has been found on frq expression (Crosthwaite et al. 1995). Frq transcription is rapidly induced by light exposure and this effect of light can explain photic entrainment in Neurospora in a simple and direct manner.

Although there are remarkable functional similarities between per and frq, there are also distinct differences. The phases of the mRNA rhythms are different: per peaks at night (Hardin et al. 1990), whereas frq peaks during the day (Aronson et al. 1994). While per overexpression shortens circadian period (Smith & Konopka 1982, Baylies et al. 1987), frq overexpression does not change period but rather abolishes overt rhythmicity (Aronson et al. 1994). The null allele, $per^O$, leads to a constant level of mRNA that is about 50% of the peak level of wild-type levels in Drosophila (Hardin et al. 1990); while in Neurospora, $frq^9$ mRNA levels are significantly elevated relative to wild-type (Aronson et al. 1994). Finally, the action of light on these two systems is opposite: light degrades TIM protein in Drosophila; whereas, it activates the transcription of frq in Neurospora These differences can be interpreted in at least two ways: 1) the elements of each system are not fully defined and frq and per could define different elements in a conserved pathway within the oscillator feedback loop; or 2) the Drosophila and Neurospora circadian clocks could be functionally analogous rather than phylogenetically homologous. Irrespective of the interpretation, however, it appears likely that a transcription-translation autoregulatory feedback loop may be a common feature of circadian clocks.

Searching for per homologs in mammals has not been very productive despite ten years of effort by a number of laboratories. This is probably due to the relatively low level of sequence similarity of per even among the Drosophilids (Hall 1990). Putative per homologs in mammals have been reported in searches directed against the threonine-glycine (TG) repeat region of PER (Shin et al. 1985, Matsui et al. 1993) and the region of the $per^S$ mutation (Siwicki et al. 1992). However, the TG-repeat clones show no other sequence similarity to PER, and the antigenes detected by antibodies to the $per^S$ region have not been characterized molecularly. New efforts targeted against the PAS dimerization domain (Huang et al. 1993), which is moderately well-conserved among insects (Reppert et al. 1994), using either PCR-based approaches or the yeast two-hybrid system (Fields & Song 1989) could eventually succeed as more bona fide per homologs are cloned in species more closely related to insects. Alternatively, as other Drosophila clock genes are cloned in the future, some should have sequence conservation with mammals as found, for example, with genes regulating pattern formation (Krumlauf 1993) or signal transduction (Zipursky & Rubin 1994). However, at this time no confirmed orthologs of per, tim or frq have been cloned in any vertebrate.

Very little information on the genetics of mammalian circadian rhythms is available. Most work in the field has used quantitative genetic approaches such as comparisons of circadian phenotype among inbred strains of mice and rats, recombinant inbred strain analysis, or selection of natural variants (Hall 1990, Schwartz & Zimmerman 1990, Lynch & Lynch 1992). The most comprehensive analysis of inbred mouse strains was done by Schwartz & Zimmerman (1990) who compared 12 different strains and found that the most extreme strains (C57BL/6J and BALB/cByJ) had a period difference of about one hour in constant darkness. Reciprocal F1 hybrid and recombinant inbred strain analysis provided no evidence of monogenic inheritance of the circadian period. Polygenic inheritance of circadian traits (or more strictly, failure to detect monogenic inheritance) has been the conclusion of every quantitative genetic analysis performed thus far.

A notable exception to the general finding of polygenic control of circadian phenotype is the spontaneous mutation, tau, found in the golden hamster (Ralph & Menaker 1988). Tau is a semidommant, autosomal mutation that shortens circadian period by two hours in heterozygotes and by four hours in homozygotes. Its phenotype is remarkably similar to the Drosophila per^S allele being semidominant, changing period to the same extent, and increasing the amplitude of the phase response curve to light (Ralph & Menaker 1988, Ralph 1991). The tau mutation has been extremely useful for physiological analysis. For example, the circadian pacemaker function of the suprachiasmatic nuclei (SCN) has been definitively demonstrated by transplantation of SCN tissue derived from tau mutant hamsters to establish that the genotype of the donor SCN determines the period of the restored rhythm (Ralph et al. 1990). Furthermore, the effects of having both tau mutant and wild-type SCN tissue in the same animal show that both mutant (~20 h) and wild-type (~24 h) periodicities can be expressed simultaneously suggesting that very little interaction of the oscillators occurs under these conditions (Vogelbaum & Menaker 1992). Additional cellular interactions can also be studied by transplantation of dissociated SCN cells derived from tau mutant and wild-type animals (Ralph & Lehman 1991). Thus, a number of issues that could not be addressed previously have been resolved or approached by the use of the tau mutation.

Unfortunately, not much progress has been made on the genetic and molecular nature of tau. Genetic mapping and molecular cloning of tau remains difficult because of the paucity of genetic information in the golden hamster. Thus far the tau mutation has contributed substantially to physiological analysis, but it will be difficult to elucidate the nature of the tau gene product unless candidate genes become apparent or the hamster is developed as a genetic system.

BRIEF SUMMARY OF THE INVENTION

In one aspect, the present invention provides an isolated and purified polynucleotide comprising a nucleotide sequence consisting essentially of a nucleotide sequence selected from the group consisting of (a) the sequence of SEQ ID NO:1 from about nucleotide position 491 to about nucleotide position 2953; (b) sequences that are complementary to the sequences of (a), and (c) sequences that, when expressed, encode a polypeptide comprising an amino acid residue sequence encoded by the sequence of (a). A polynucleotide can be a DNA or RNA molecule. A preferred polynucleotide contains the nucleotide sequence from nucleotide position number 419, 416, 392, 389 or 1 to nucleotide position number 2953 of SEQ ID NO:1.

In another embodiment, a polynucleotide of the present invention is contained in an expression vector. The expression vector preferably further comprises an enhancer-promoter operatively linked to the polynucleotide. In an especially preferred embodiment, the polynucleotide contains a nucleotide sequence as set forth above. The present invention still further provides a host cell transformed with a polynucleotide or expression vector of this invention. Preferably, the host cell is a bacterial cell such as an E. coli.

In another aspect, the present invention provides an oligonucleotide of from about 15 to about 50 nucleotides containing a nucleotide sequence that is identical or complementary to a contiguous sequence of at least 15 nucleotides a polynucleotide of this invention. A preferred oligonucleotide is an antisense oligonucleotide that is complementary to a portion of the polynucleotide of SEQ ID NO:1.

In another aspect, the present invention provides a polypeptide of mammalian origin. In one embodiment, that polypeptide is an isolated and puried polypeptide of about 855 or less amino acid residues that contains the amino acid residue sequence of at least one of:
  a) from residue position 35 to residue position 855 of SEQ ID NO:2;
  b) from residue position 11 to residue position 855 of SEQ ID NO:2;
  c) from residue position 10 to residue position 855 of SEQ ID NO:2;
  d) from residue position 2 to residue position 855 of SEQ ID NO:2; or
  e) from residue position 1 to residue position 855 of SEQ ID NO:2.

Preferably, a polypeptide of the present invention is a recombinant human polypeptide. In another aspect, the present invention provides a process of making a polypeptide of this invention comprising transforming a host cell with an expression vector that comprises a polynucleotide of the present invention, maintaining the transformed cell for a period of time sufficient for expression of the polypeptide and recovering the polypeptide. Preferably, the host cell is an eukaryotic host cell such as a mammalian cell, or a bacterial cell. An especially preferred host cell is an E. coli. The present invention also provides a polypeptide made by a process of this invention.

The present invention also provides a pharmaceutical composition comprising a polypeptide, polynucleotide, expression vector or oligonucleotide of this invention and a physiologically acceptable diluent.

In another aspect, the present invention provides uses for the polypetides, polynucleotides and oligonucleotides of the present invention.

BRIEF DESCRIPTION OF THE DRAWINGS

In the drawings which form a portion of the specification:

FIG. 5 is a schematic illustration of the breeding strategy used to produce TG36 progeny.

FIG. 9 (in four panels, 9-1, 9-2, 9-3 and 9-4) shows the nucleotide sequence of individual exons.

FIG. 10 shows the splice acceptor and donor sequences for the exons.

FIG. 11 shows a comparison between the amino acid residue sequence of the CLOCK polypeptide with human NPAS2 and mouse NPAS2.

FIG. 12 shows the amino acid sequence of CLOCK with the bHLH, PAS-A, PAS-B domains of a mutant Clock gene.

FIG. 13 shows the amino acid sequence of a CLOCK variant resulting from an alternate splice.

DETAILED DESCRIPTION OF THE INVENTION

I. The Invention

Figure 1:
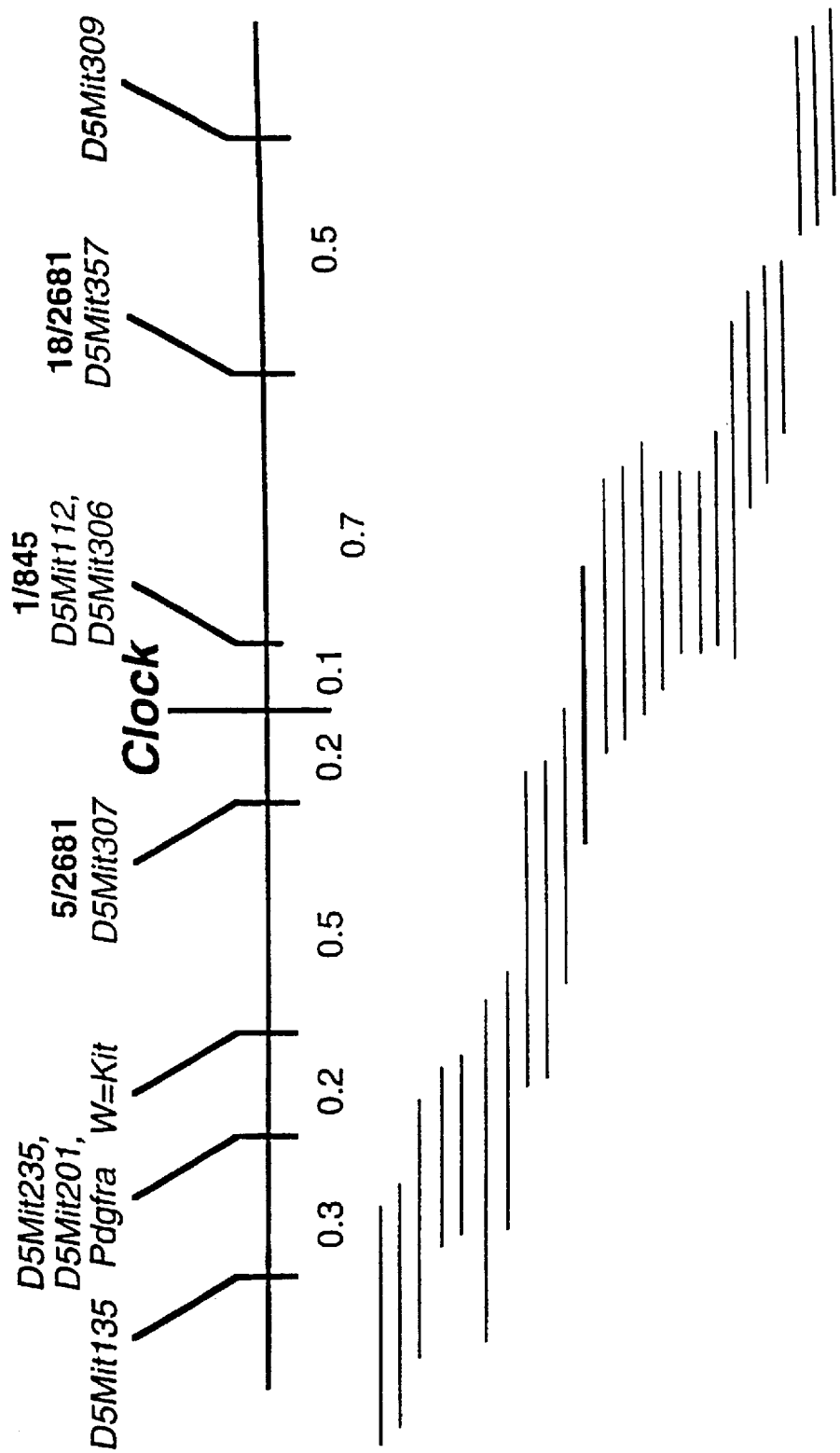
FIG. 1 shows the location of the Clock gene locus in the mouse genome using genetic meiotic mapping.

The present invention provides isolated and purified polypeptide components of the mammalian circadian clock, polynucleotides that encode those polypeptides, expression vectors containing those polynucleotides, host cells transformed with those expression vectors, a process of making the polypeptide components using those polynucleotides and vectors and processes using those polypeptides and polynucleotides.

II. Clock Polypeptides

In one aspect, the present invention provides a polypeptide that is an integral component of the mammalian circadian clock. The polypeptide serves to regulate various aspects of circadian rhythm in mammals. The polypeptide is referred to herein as the CLOCK polypeptide. The CLOCK polypeptide contains about 855 or less amino acid residues. The amino acid residue sequence of an 855 residue embodiment of CLOCK, which embodiment is the gene product of the Clock gene, described hereinafter, is set forth in SEQ ID NO:2.

It can be seen from SEQ ID NO:2 that the 855 residue embodiment is a member of the basic helix-loop-helix (bHLH)-PAS domain family of proteins. The basic region of the bHLH domain is known to mediate DNA binding. Thus, CLOCK likely interacts directly with DNA. The HLH and PAS domains are further known to be protein dimerization domains and indicate that CLOCK can interact with itself or with other HLH-PAS domain family members. The C-terminal portion of SEQ ID NO:2 can also be seen to have a number of glutamine-rich, proline-rich and serine-rich regions that are characteristic of activation domains of transcription factors. The CLOCK polypeptide functions as a transcription factor.

There are two methionine (Met) residues in the N-terminal portion of SEQ ID NO:2, both of which can serve as the N-terminus of a CLOCK polypeptide. Those two Met residues are located at residue positions 1 and 10 of SEQ ID NO:2. Thus, a CLOCK polypeptide of the present invention can contain the amino acid residue sequence of SEQ ID NO:2 extending from residue number 1 or residue number 10 to the C-terminus (residue number 855). As is well known in the art, polypeptides with an N-terminal Met residue can be produced without that Met residue, which Met-minus polypeptide has the same function as the Met-positive embodiment. Thus, a CLOCK polypeptide of the present invention can contain the amino acid residue sequence of SEQ ID NO:2 from residue number 2 or residue number 11 to residue number 855.

As is also well know in the art, proteins having b-HLH dormans can be processed such that the polypeptide starts at the beginning of that b-HLH domain. In SEQ ID NO:2, the b-HLH begins at amino acid residue number 35. Thus, an embodiment of a CLOCK polypeptide of the present invention contains a polypeptide having the amino acid residue sequence of SEQ ID NO: 2 from residue number 35 to residue number 855.

As set forth in detail hereinafter, four forms of the CLOCK polypeptide have been identified in the mouse. Those four forms are: (1) SEQ ID NO:2; (2) residues 1 to 513 and residues 565 to 855 of SEQ ID NO:2; (3) residues 1 to 483 and residues 514 to 855 of SEQ ID NO:2; and (4) residues 1 to 483 and residues 565 to 855 of SEQ ID NO:2.

The present invention also contemplates amino acid residue sequences that are substantially duplicative of the sequences set forth herein such that those sequences demonstrate like biological activity to disclosed sequences. Such contemplated sequences include those sequences characterized by a minimal change in amino acid residue sequence or type (e.g., conservatively substituted sequences) which insubstantial change does not alter the basic nature and biological activity of the CLOCK polypeptide.

It is well known in the art that modifications and changes can be made in the structure of a polypeptide without substantially altering the biological function of that peptide. For example, certain amino acids can be substituted for other amino acids in a given polypeptide without any appreciable loss of function. In making such changes, substitutions of like amino acid residues can be made on the basis of relative similarity of side-chain substituents, for example, their size, charge, hydrophobicity, hydrophilicity, and the like.

As detailed in U.S. Pat. No. 4,554,101, incorporated herein by reference, the following hydrophilicity values have been assigned to amino acid residues: Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5)- Leu (−1.8); Ile (−1.8) Tyr (−2.3); Phe (−2.5); and Trp (−3.4). It is understood that an amino acid residue can be substituted for another having a similar hydrophilicity value (e.g., within a value of plus or minus 2.0) and still obtain a biologically equivalent polypeptide.

In a similar manner, substitutions can be made on the basis of similarity in hydropathic index. Each amino acid residue has been assigned a hydropathic index on the basis of its hydrophobicity and charge characteristics. Those hydropathic index values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−0.9); Tyr (−1.3); Pro (−1.6); His (−3.2); Glu (−3.5); Gln (−3.5); Asp (−3.5); Asn (−3.5); Lys (−3.9); and Arg (−4.5). In making a substitution based on the hydropathic index, a value of within plus or minus 2.0 is preferred.

The CLOCK polypeptide of the present invention contains numerous phosphorylation sites. This invention contemplates phosphorylated as well as unphosphorylated embodiments A CLOCK polypeptide of the present invention has numerous uses. By way of example, such a polypeptide can be used in a screening assay for the identification of drugs or compounds that inhibit the action of CLOCK polypeptide (e.g., DNA binding). The CLOCK polypeptide is an integral component of the circadian clock of mammals. As set forth below, animals lacking the ability to produce the CLOCK polypeptide have significant dysfunctions in their circadian clock. Mutant animals producing an altered CLOCK polypeptide can be given the normal CLOCK polypeptide together with suspected agonists or antagonists and the effects of such treatment on the restoration of a normal circadian rhythn can be determined. The CLOCK polypeptide can also be used to treat animals having circadian rhythm dysfunctions as set forth hereinafter.

In addition, a CLOCK polypeptide of the present invention can be used to produce antibodies that immunoreact specifically with the CLOCK polypeptide or antigenic determinants thereof. Means for producing antibodies are well known in the art. An antibody directed against CLOCK polypeptide can be a polyclonal or a monoclonal antibody.

Antibodies against CLOCK polypeptide can be prepared by immunizing an animal with a CLOCK polypeptide of the present invention or an immunogenic portion thereof. Means for immunizing animals for the production of antibodies are well known in the art. By way of an example, a mammal can be injected with an inoculum that includes a polypeptide as described herein above. The polypeptide can be included in an inoculum alone or conjugated to a carrier protein such as keyhole limpet hemocyanin (KLH). The polypeptide can be suspended, as is well known in the art, in an adjuvant to enhance the immunogenicity of the polypeptide. Sera containing immunologically active antibodies are then produced from the blood of such immunized animals using standard procedures well known in the art.

The identification of antibodies that immunoreact specifically with CLOCK polypeptide is made by exposing sera suspected of containing such antibodies to a polypeptide of the present invention to form in a conjugate between antibodies and the polypeptide. The existence of the conjugate is then determined using standard procedures well known in the art.

A CLOCK polypeptide of the present invention can also be used to prepare monoclonal antibodies against CLOCK polypeptide and used as a screening assay to identify such monoclonal antibodies. Monoclonal antibodies are produced from hybridomas prepared in accordance with standard techniques such as that described by Kohler et al. (*Nature* 256:495, 1975). Briefly, a suitable mammal (e.g., BALB/c mouse) is immunized by injection with a polypeptide of the present invention. After a predetermined period of time, splenocytes are removed from the mouse and suspended in a cell culture medium. The splenocytes are then fused with an immortal cell line to form a hybridoma. The formed hyridomas are grown in cell culture and screened for their ability to produce a monoclonal antibody against CLOCK polypeptide. Screening of the cell culture medium is made with a polypeptide of the present invention.

III. Clock Polynucleotides

In another aspect, the present invention provides an isolated and purified polynucleotide that encodes a CLOCK polypeptide of mammalian origin. The polynucleotide can be a DNA molecule (e.g., genomic sequence, cDNA) or an RNA molecule (e.g., mRNA). Where the polynucleotide is a genomic DNA molecule, that molecule can comprise exons and introns interspersed therein.

As set forth hereinafter in the Examples, the Clock gene contains numerous exons. One of skill in the art will readily appreciate that the entire genome including introns is contemplated by the present invention. Where the polynucleotide is a cDNA molecule, disclosed sequences include coding regions as well as 5'- and 3'-untranslated regions.

Only coding DNA sequences are disclosed herein. The present invention also provides, however, non-coding strands that are complementary to the coding sequences as well as RNA sequences identical to or complementary to those coding sequences. One of ordinary skill will readily appreciate that corresponding RNA sequences contain uracil (U) in place of thymidine (T).

In one embodiment, a polynucleotide of the present invention is an isolated and purified cDNA molecule that contains a coding sequence for a CLOCK polypeptide of this invention. An exemplary and preferred such cDNA molecule is shown as SEQ ID NO:1. SEQ ID NO:2 is the deduced amino acid residue sequence of the coding region of SEQ ID NO:1. As set forth above, a CLOCK polypeptide of the present invention can be a truncated or shortened form of SEQ ID NO:2. Thus, preferred polynucleotides of this invention depend on the specific CLOCK polypeptide preferred.

By way of example, where the CLOCK polypeptide contains the amino residue sequence of SEQ ID NO:2 from residue number 1 to residue acid number 855, a preferred polynucleotide contains the nucleotide sequence of SEQ ID NO:1 from nucleotide number 389 to nucleotide number 2953. Where the CLOCK polypeptide contains the amino acid residue sequence of SEQ ID NO:2 from residue number 2 to residue number 855, a preferred polynucleotide contains the nucleotide sequence of SEQ ID NO:1 from nucleotide number 392 to nucleotide number 2953. Where the CLOCK polypeptide contains the amino acid residue sequence of SEQ ID NO:2 from residue number 10 to residue number 855, a preferred polynucleotide contains the nucleotide sequence of SEQ ID NO:1 from nucleotide number 416 to nucleotide number 2953. Where the CLOCK polypeptide contains the amino acid residue sequence of SEQ ID NO:2 from residue number 11 to residue number 855, a preferred polynucleotide contains the nucleotide sequence of SEQ ID NO:1 from nucleotide number 419 to nucleotide number 2953. Where the CLOCK polypeptide contains the amino acid residue sequence of SEQ ID NO:2 from residue number 35 to residue number 855, a preferred polynucleotide contains the nucleotide sequence of SEQ ID NO:1 from nucleotide number 491 to nucleotide number 2953. Other preferred polypeptides such as those encoding the four distinct forms of CLOCK found in the mouse, will be readily apparent to a skilled artisan by reference to the cDNA and amino acid residue sequences disclosed herein.

The present invention also contemplates DNA sequences which hybridize under stringent hybridization conditions to the DNA sequences set forth above. Stringent hybridization conditions are well known in the art and define a degree of sequence identity greater than about 70%–80%. The present invention also contemplates naturally occurring allelic variations and mutations of the DNA sequences set forth above so long as those variations and mutations code, on expression, for a CLOCK polypeptide of this invention as set forth hereinbefore.

As is well known in the art, because of the degeneracy of the genetic code, there are numerous other DNA and RNA molecules that can code for the same polypeptides as those encoded by SEQ ID NO:1, or portions thereof. The present invention, therefore, contemplates those other DNA and RNA molecules which, on expression, encode for a polypeptide that contains a polypeptide encoded by SEQ ID NO:1, or portions thereof as set forth above. Having identified the amino acid residue sequence of CLOCK polypeptides, and with knowledge of all triplet codons for each particular amino acid residue, it is possible to describe all such encoding RNA and DNA sequences. DNA and RNA molecules other than those specifically disclosed herein and, which molecules are characterized simply by a change in a codon for a particular amino acid are within the scope of this invention.

A Table of codons representing particular amino acids is set forth below in Table 1.

TABLE I

| First position | Second Position | | | | Third position |
|---|---|---|---|---|---|
| (5'end) | T/U | C | A | G | (3'end) |
| T/U | Phe | Ser | Tyr | Cys | T/U |
|  | Phe | Ser | Tyr | Cys | C |
|  | Leu | Ser | Stop | Stop | A |
|  | Leu | Ser | Stop | Trp | G |
| C | Leu | Pro | His | Arg | T/U |
|  | Leu | Pro | His | Arg | C |
|  | Leu | Pro | Gln | Arg | A |
|  | Leu | Pro | Gln | Arg | G |
| A | Ile | Thr | Asn | Ser | T/U |
|  | Ile | Thr | Asn | Ser | C |
|  | Ile | Thr | Lys | Arg | A |
|  | Met | Thr | Lys | Arg | G |
| G | Val | Ala | Asp | Gly | T/U |
|  | Val | Ala | Asp | Gly | C |
|  | Val | Ala | Glu | Gly | A |
|  | Val | Ala | Glu | Gly | G |

A simple change in a codon for the same amino acid residue within a polynucleotide will not change the structure of the encoded polypeptide. By way of example, it can be seen from SEQ ID NO:1 that a TCA codon for serine exists at nucleotide positions 422–424 and at positions 512–514. It can also be seen from that same sequence, however, that serine can be encoded by a AGC codon (see e.g., nucleotide positions 419–421 and 617–619). Substitution of the latter AGC codon for serine with the TCA codon for serine, or visa versa, does not substantially alter the DNA sequence of SEQ ID NO:1 and results in expression of the same polypeptide. In a similar manner, substitutions of codons for other amino acid residues can be made in a like manner without departing from the true scope of the present invention.

A polynucleotide of the present invention can also be an RNA molecule. An RNA molecule contemplated by the present invention is complementary to or hybridizes under stringent conditions to any of the DNA sequences set forth above. As is well known in the art, such an RNA molecule is characterized by the base uracil in place of thymidine. Exemplary and preferred RNA molecules are mRNA molecules that encode a CLOCK polypeptide of this invention.

IV. Clock Olizonucleotides

The present invention also contemplates oligonucleotides from about 15 to about 50 nucleotides in length, which oligonucleotides serve as primers and hybridization probes for the screening of DNA libraries and the identification of DNA or RNA molecules that encode a CLOCK polypeptide. Such primers and probes are characterized in that they will hybridize to polynucleotide sequences encoding a CLOCK polypeptide. An oligonucleotide probe or primer contains a nucleotide sequence that is identical to or complementary to a contiguous sequence of at least 15 nucleotides of a polynucleotide of the present invention. Thus, where an oligonucleotide probe is 25 nucleotides in length, at least 15 of those nucleotides are identical or complementary to a sequence of contiguous nucleotides of a polynucleotide of the present invention. Exemplary polynucleotides of the present invention are set forth above.

A preferred oligonucleotide is an antisense oligonucleotide. The present invention provides a synthetic antisense oligonucleotide of less than about 50 nucleotides, preferably less than about 35 nucleotides, more preferably less than about 25 nucleotides and most preferably less than about 20 nucleotides. An antisense oligonucleotide of the present invention is directed against a DNA or RNA molecule that encodes a CLOCK polypeptide. Preferably, the antisense oligonucleotide is directed against the protein translational initiation site or the transcriptional start site. In accordance with this preferred embodiment, an antisense molecule is directed against a region of SEQ ID NO:1 from about nucleotide position 370 to about nucleotide position 410 or a portion of SEQ ID NO:1 from about nucleotide position 400 to about nucleotide position 440. It is understood by one of ordinary skill in the art that antisense oligonucleotides can be directed either against a DNA or RNA sequence that encodes a specific target. Thus, an antisense oligonucleotide of the present invention can also be directed against polynucleotides that are complementary to those shown in SEQ ID NO:1 as well as the equivalent RNA molecules.

Preferably, the nucleotides of an antisense oligonucleotides are linked by pseudophosphate bonds that are resistant to clevage by exonuclease or endonuclease enzymes. Preferably the pseudophsphate bonds are phosphorothioate bonds. By replacing a phosphodiester bond with one that is resistant to the action of exo-and/or endonuclease, the stability of the nucleic acid in the presence of those enzymes is increased. As used herein, pseudophosphate bonds include, but are not limited to, methylphosphonate, phosphomorpholidate, phosphorothioate, phosphorodithioate and phosphoroselenoate bonds.

An oligonucleotide primer or probe, as well as an antisense oligonucleotide of the present invention can be prepared using standard procedures well known in the art. A preferred method of polynucleotide synthesis is via cyanoethyl phosphoramidite chemistry. A detailed description of the preparation, isolation and purification of polynucleotides encoding mammalian CLOCK is set forth below V. Expression Vectors and Transformed Cells The present invention further provides expression vectors that contain a polynucleotide of the invention and host cells transformed or transfected with those polynucleotides or expression vectors.

A polynucleotide that encodes a CLOCK polypeptide is placed into an expression vector suitable for a given host cell such that the vector drives expression of the polynucleotide in that host cell. Vectors for use in particular cells are well known in the art and include viral vectors, phages or plasmids.

In one embodiment, a host cell is an eukaryotic host cell and an expression vector is an eukaryotic expression vector (i.e., a vector capable of directing expression in a eukaryotic cell). Such eukaryotic expression vectors are well known in the art. In another embodiment, the host cell is a bacterial cell. An especially preferred bacterial cell is an *E. coli*. Thus, a preferred expression vector is a vector capable of directing expression in *E. coli*

A polynucleotide of an expression vector of the present invention is preferably operatively associated or linked with an enhancer-promoter. A promoter is a region of a DNA molecule typically within about 100 nucleotide pairs in front of (upstream of) the point at which transcription begins. That region typically contains several types of DNA sequence elements that are located in similar relative positions in different genes. As used herein, the term "promoter" includes what is referred to in the art as an upstream promoter region or a promoter of a generalized RNA polymerase transcription unit.

Another type of transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from a transcription start site so long as the promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" or its grammatical equivalent means that a regulatory sequence element (e.g. an enhancer-promoter or transcription terminating region) is connected to a coding sequence in such a way that the transcription of that coding sequence is controlled and regulated by that enhancer-promoter. Means for operatively linking an enhancer-promoter to a coding sequence are well known in the art.

An enhancer-promoter used in an expression vector of the present invention can be any enhancer-promoter that drives expression in a host cell. By employing an enhancer-promoter with well known properties, the level of expression can be optimized. For example, selection of an enhancer-promoter that is active in specific cells (e.g., cells of the SCN) permits tissue or cell specific expression of the desired product. Still further, selection of an enhancer-promoter that is regulated in response to a specific physiological signal can permit inducible expression.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Enhancer-promoters and transcription-terminating regions are well known in the art. The selection of a particular enhancer-promoter or transcription-terminating region will depend, as is also well known the art, on the cell to be transformed.

VI. Method of Making Clock Polynucleotide

In another aspect, the present invention provides a process of making a CLOCK polypeptide. In accordance with that process, a suitable host cell is transformed with a polynucleotide of the present invention. The transformed cell is maintained for a period of time sufficient for expression of the CLOCK polypeptide. The formed polypeptide is then recovered. Preferably, the polynucleotide is contained in an expression vector as set forth above.

VII. Pharmaceutical Compositions

The present invention also provides a pharmaceutical composition comprising a polypeptide, polynucleotide, oligonucleotide or expression vector of this invention and a physiologically acceptable diluent.

In a preferred embodiment, the present invention includes one or more antisense oligonucleotides, polypeptides or expression vectors, as set forth above, formulated into compositions together with one or more non-toxic physiologically tolerable or acceptable diluents, carriers, adjuvants or vehicles that are collectively referred to herein as diluents, for parenteral injection, for oral administration in solid or liquid form, for rectal or topical administration, or the like.

The compositions can be administered to humans and animals either orally, rectally, parenterally, intracisternally, intravaginally, intraperitoneally, locally, or as a buccal or nasal spray.

Compositions suitable for parenteral administration can comprise physiologically acceptable sterile aqueous or non-aqueous solutions, dispersions, suspensions or emulsions and sterile powders for reconstitution into such sterile solutions or dispersions. Examples of suitable diluents include water, ethanol, polyols, suitable mixtures thereof, vegetable oils and injectable organic esters such as ethyl oleate. Proper fluidity can be maintained, for example, by the use of a coating such as lecithin, by the maintenance of the required particle size in the case of dispersions and by the use of surfactants.

Compositions can also contain adjuvants such as preserving, wetting, emulsifying, and dispensing agents. Prevention of the action of microorganisms can be insured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceuticalform can be brought about by the use of agents delaying absorption, for example, aluminum monostearate and gelatin.

Besides such inert diluents, the composition can also include sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonit, agar-agar and tragacanth, or mixtures of these substances, and the like.

VIII. Process of Using CLOCK Polypeptides, Polynucleotides and Oligonucleotides

The present invention provides processes for using the polypeptide, polynucleotides, and oligonucleotides of the present invention. The compositions and methods of the present invention have a variety of uses. Having described the Clock gene and its expression product, the CLOCK polypeptide, it is possible to inhibit expression of the Clock gene using gene targeting technology as is well know in the art. Using such technology, for example, the Clock gene can be removed from the genome of the mouse or that gene can otherwise be mutated so as to prevent expression of the CLOCK polypeptide. As a result of such treatments, a mouse model is created that is characterized by having circadian clock dysfunctions. That model can then be used in screening essays to identify therapeutic agents that affect circadian rhythm or to study a variety of chemical, physiological, or behavioral activities associated with the circadian rhythm.

As set forth above, the amino acid residue sequence of the CLOCK polypeptide indicates that it is a transcription factor and contains a DNA binding domain. The CLOCK polypeptide, or the DNA binding domain portion thereof, can therefore be used to identify the specific DNA binding site and/or to identify agonist or antagonist substances that interfere with DNA binding of the CLOCK polypeptide. Means for accomplishing such screening assays are well known in the art.

Briefly, once the DNA binding site is identified, that DNA binding site, together with the DNA binding domain of the CLOCK polypeptide, can be exposed to a variety of agents suspected of being agonists or antagonists to DNA binding. The ability of those compounds to interfere with binding of the CLOCK polypeptides to its DNA binding site is indicative of the agonist or antagonist nature of those substances. Alternatively, the DNA binding site can be placed in an expression vector such that binding of a CLOCK polypeptide to that binding site allows for expression of a reporter gene operatively linked to the DNA binding site. The ability of compounds to inhibit or enhance expression of the reporter gene is indicative of agonist or antagonist activity.

The CLOCK polypeptide, or the DNA binding domain thereof, can also be used to screen DNA libraries to identify the specific binding site on a DNA molecule. Screening can be accomplished with genomic libraries in general or with specifically targeted portions of genomic DNA. As set forth above, for example, it is likely that the DNA binding domain of the CLOCK polypeptide binds within the promoter region of the Clock gene itself. Binding studies can therefore be targeted to this region of the Clock gene.

Once the DNA binding site of the CLOCK polypeptide has been determined, the three dimensional structure of the CLOCK polypeptide, or its DNA binding domain, bound to the target DNA site can be determined using techniques well known in the art, such as X-ray crystallography. Knowledge of the three-dimensional structure of the bound CLOCK polypeptide will thus allow for computer aided rational drug design for identification of agonist or antagonist compounds.

The well known yeast two-hybrid system can be used to determine whether the CLOCK polypeptide interacts with another protein (heterodimerization) or with itself (homodimerization). Briefly, yeast cells are transformed with a reporter gene operatively associated with a promoter that contains a binding site for GAL 4. That same yeast is then transformed with a polynucleotide that encodes a CLOCK polypeptide of the present invention, or a dimerization domain thereof. Finally, that same yeast cell is transformed a protein expression cDNA library. Transformed yeast will only survive if the CLOCK polypeptide interacts with a second protein resulting from expression of the protein expression cDNA library and that interaction causes GAL 4 to bind to the promoter region of the reporter gene and express that reporter gene.

In yet another embodiment, compositions of the present invention can be used to screen genomic libraries in plants and animals to identify the corresponding Clock genes in these species. Identification of the Clock gene in these species is important because the growth and metabolic rate of plants and animals is known to be regulated, at least in part, by the circadian rhythm. By way of example, photosynthesis in plants is known to comprise both a light and dark reaction. Manipulation of the circadian clock in plants, therefore, can result in alteration of those light and dark reactions. Similarly, the growth rate of animals used for feed (cattle and pigs) is known to be a function of the circadian rhythm. The ability to manipulate the circadian rhythm in those animals can thus result an enhanced growth of those important animals.

The expression of diurnal (i.e. 24-hr) rhythms is a fundamental property of almost all forms of life. These rhythms are regulated by an internal "biological clock" that in many organisms, including humans, can be synchronized by the light dark cycle. This internal 24-hr clock is referred to as a "circadian clock" because in the absence of any diurnal environmental cues, the period of the clock is rarely exactly 24 hours but is instead about 24 hrs (i.e. circa diem).

The circadian clock in mammals is known to regulate 24 hour rhythms in biochemical, cellular, metabolic and behavioral activity in most, if not all, physiological systems. The following is a list of exemplary activities controlled at least in part by the circadian clock and activities that affect that clock, which can be manipulated to restore the function of an abnormal allele of the Clock gene.

1. The circadian clock is a major regulator of the sleep-wake cycle (Borbély, 1994; Kryger et al., 1994) and many pathologic changes in the sleep wake cycle are associated with circadian rhythm disorders (Roehrs and Roth, 1994). Therefore, this patent covers any use of Clock, or its protein product, for the development or use of new techniques and/or pharmaceutical approaches for the treatment of any sleep disorders.
2. When people move rapidly across time zones, they suffer from a well-known syndrome, referred to as jet-lag, until their biological clock and sleep-wake cycle become resynchronized to the new time zone (Graeber, 1994). Therefore, this patent covers any use of Clock, or its protein product, for the development or use of new techniques and/or pharmaceutical approaches for the treatment of jet-lag.
3. When people must be awake during the normal sleep period, and/or asleep during the normal wake period, they suffer decrements in health, performance and productivity as well as an increased rate of accidents (Monk, 1990; Monk, 1994; Smith et al., 1994; US Congress, September, 1991). Therefore, this patent covers any use of Clock, or its protein product, for the development or use of new techniques and/or pharmaceutical approaches for the treatment of disorders of time-keeping associated with having to be awake during the biological clock time of normal sleep and asleep during the biological clock time of normal wake. This coverage of the patent includes the use of Clock, and/or it's protein product for alleviating the adverse effects associated with shift work where workers are working during the time of normal sleep and sleeping during the time of normal wake.
4. The circadian clock regulates the timing of fatigue and alertness (Monk et al., 1984; Roth et al., 1994). Therefore, this patent covers any use of Clock, or its protein product, for the development or use of new techniques and/or pharmaceutical approaches for altering the cycle of fatigue and alertness, as well as for decreasing fatigue or increasing alertness by altering circadian rhythmicity.
5. Circadian rhythm disruption has been associated with many forms of altered mental states, including but not limited to depression (both unipolar and bipolar), premenstrual syndrome post-menopausal syndrome, and schizophrenia (Hallonquist et al., 1986; Ohta and Endo, 1985; Van Cauter and Turek, 1986; Wehr and Goodwin, 1983; Wehr et al., 1983; Wehr et al., 1979). Therefore, this patent covers any use of Clock, or its protein product, for the development or use of new techniques and/or pharmaceutical approaches for the treatment of any mental disorders.
6. Studies have shown that the human has a pronounced cycle of mood and performance (Benca, 1994; Monk et al., 1985). Therefore, this patent covers any use of Clock or its protein product, for the development or use of new techniques and/or pharmaceutical approaches for altering the mood state or performance.
7. The circadian clock regulates the timing of many physiological and endocrine processes that when disturbed lead to various mental and physical disorders (Richter, 1979; Turek and Van Cauter, 1994; Van Cauter and Turek, 1995). Therefore, this patent covers any use of Clock, or its protein product, for the development or use of new techniques and/or pharmaceutical approaches for the treatment of any mental and physical disorders.
8. Abnormal circadian rhythm and abnormal sleep-wake cycles have been associated with various neurological diseases (Aldrich, 1994; Bliwise, 1994; Hartmann, 1994; Hineno et al., 1992; Hyde et al., 1995; Lugaresi and Montagna, 1994; Poirel, 1991; Weltzin et al., 1991). Therefore, this patent covers any use of Clock; or its protein product, for the development or use of new techniques and/or pharmaceutical approaches for the treatment of any neurological disorders.
9. The circadian clock regulates the timing of many physiological and endocrine processes associated with stress (Sapolsky, 1992; Tornatzky and Miczek, 1993; Van Cauter and Turek, 1995). Therefore, this patent covers any use of Clock, or its protein product, for the development or use of new techniques and/or pharmaceutical approaches for relieving stress or altering the stress response in humans.
10. Many components of the cardiovascular system show rhythmic variation, and the timing of such major insults to the cardiovascular system, such as heart attack and stroke, are known to be regulated by the circadian clock system and/or be influenced by the time-of-day (Aschoff, 1992; Cohen and Muller, 1992; George, 1994; Gillis and Flemons, 1994; Maron et al., 1994; Sano et al., 1995). Therefore, this patent covers any use of Clock, or its protein product, for the development or use of new techniques and/or pharmaceutical approaches for the treatment of any diseases of the cardiovascular system.

11. The circadian clock plays a central role in the regulation of the diurnal cycle in feeding behavior (Rusak and Zucker, 1975). Furthermore, many components of the system involved with feeding as well as the regulation of metabolism, body fat and weight control are regulated by the circadian clock system (Benca and Casper, 1994; de Graaf et al., 1993; Larsen et al., 1991; Orr, 1994; Van Cauter and Turek, 1995). Therefore, this patent covers any use of Clock, or its protein product, for the development or use of new techniques and/or pharmaceutical approaches for the treatment of any disorders of feeding behavior as well as attempts to regulate diet and/or food intake.

12. The circadian clock regulates the timing of many physiological and endocrine events associated with diabetes (Spallone et al., 1993; Van Cauter and Turek, 1995). Therefore, this patent covers any use of Clock, or its protein product, for the development or use of new techniques and/or pharmaceutical approaches for the treatment of diabetes and related illnesses.

13. The circadian clock regulates the timing of many components of the immune system (Calvo et al., 1995; Constantinescu, 1995; Krueger and Kamovsky, 1995). Therefore, this patent covers any use of Clock, or its protein product, for the development or use of new techniques and/or pharmaceutical approaches for the treatment of any disorders of the immune system.

14. For many infectious diseases, including those of viral, bacterial or parasitic origins, the circadian clock regulates the optimum time for infection to occur, as well as the response to the infection by the host organism (Walker et al., 1981). Therefore, this patent covers any use of Clock, or its protein product, for the development or use of new techniques and/or pharmaceutical approaches for the prevention, diagnosis and/or treatment of infectious diseases.

15. The circadian clock regulates the timing of many processes associated with reproduction (Turek and Van Cauter, 1994). Therefore, this patent covers any use of Clock, or its protein product, for the development or use of new techniques and/or pharmaceutical approaches for the treatment of any reproductive disorder as well as for enhancing fertility, treating infertility or for any birth control methods as well as for affecting sexual function.

16. Many of the physiological processes and hormones involved in pregnancy and parturition are regulated by the circadian clock (Turek and Van Cauter, 1994). Therefore, this patent covers any use of Clock, or its protein product, for the development or use of new techniques and/or pharmaceutical approaches for aiding in the maintenance of pregnancy and/or in the process of parturition.

17. The circadian clock regulates the timing of many components of the respiratory system (Douglas, 1994; Orem, 1994). Therefore, this patent covers any use of Clock, or its protein product, for the development or use of new techniques and/or phan-naccutical approaches for the treatment of any respiratory illness.

18. There are pronounced diurnal variations in the functions of the liver (Colantonio et al., 1989; García-Pagáan et al., 1994). Therefore, this patent covers any use of Clock, or its protein product, for the development or use of new techniques and/or pharmaceutical approaches for the treatment of liver disease and or for altering liver function.

19. Many components of the endocrine system undergo pronounced daily changes in function (Van Cauter and Turek, 1995). Therefore, this patent covers any use of Clock, or its protein product, for the development or use of new techniques and/or pharmaceutical approaches for the treatment of any endocrine disorders, or for altering in endocrine rhythms for any purposes.

20. The circadian clock regulates the timing of the pineal melatonin rhythm (Arendt, 1995). Therefore, this patent covers any use of Clock; or its protein product, for the development or use of new techniques and/or pharmaceutical approaches for using melatonin and/or melatonin related drugs in humans for therapeutic purposes, including the use of melatonin and/or melatonin related drugs as anti-oxidants.

21. The therapeutic and toxic effects of many drugs are influenced by the time of day at which the drug is delivered and/or by the pattern of drug administration (Larsen et al., 1993; Lemmer, 1989; Walker et al., 1981). Therefore, this patent covers any use of Clock, or its protein product, for the development or use of new approaches for the use of any pharmacological agents to improve human health or welfare.

22. The therapeutic and toxic effects of many drugs are influenced by the time of day at which the drug is delivered and/or by the pattern of drug administration (Walker et al., 1981). Therefore, this patent covers any use of Clock, or its protein product, for the development or use of new techniques and/or pharmaceutical approaches in the screening of drugs for new therapeutic purposes as well as the use of Clock and its protein product for diagnostic purposes.

23. The circadian clock regulates many physiological processes that are involved in the development or suppression of many forms of cancer (Walker et al., 1981). Therefore, this patent covers any use of Clock, or its protein product, for the development or use of new techniques and/or pharmaceutical approaches for the treatment or diagnosis of any cancer, as well as other forms of abnormal cell division.

24. The circadian clock regulates many of the processes associated with growth and development (Albertsson-Wlkland and Rosberg, 1988, Hokken-Koelega et al., 1990; Mirmiran et al., 1990; Van Cauter and Turek, 1995). Therefore, this patent covers any use of Clock, or its protein product, for the development or use of new techniques and/or pharmaceutical approaches for influencing growth and development.

25. The circadian clock regulates processes associated with cell division (Edmunds Jr, 1988). Therefore, this patent covers any use of Clock, or its protein product, for the development or use of new techniques and/or pharmaceutical approaches for influencing cell division and the cellular cycle.

26. There are major changes in the circadian clock system with advancing age, and age-related changes in the circadian clock system may underlie many of the adverse health effects associated with aging (Turek et al.,1995; Van Cauter and Turek, 1995). Therefore, this patent covers any use of Clock, or its protein product, for the development or use of new techniques and/or pharmaceutical approaches for the treatment of any age-related illnesses or age-related changes in human physiology.

27. Light may have many effects on the brain that are mediated through the transmission of neural information through the central circadian clock in mammals, the hypothalamic suprachiasmatic nucleus (SCN) (Card and Moore, 1991; Meijer, 1991; Penev et al., 1997). Therefore, this patent covers any use of Clock, or its protein product, for the development or use of new techniques and/or pharmaceutical approaches for the use of light to alter neural activity in the brain.

28. The light-dark cycle is a major regulator of the timing of circadian rhythms that are controlled by the circadian clock of which Clock is a component (Turek, 1994; Turek and Van Reeth, 1996; Van Cauter and Turek, 1995). Therefore, this patent covers any use of Clock or its protein product, for the development or use of new techniques and/or pharmaceutical approaches that involve the use of light or dark to shift or influence, in any way, circadian rhythm.

29. While the light-dark cycle is a major regulator of the timing of circadian rhythm in most humans, for many blind humans the light-dark cycle is not able to synchronize the circadian clock in a normal fashion (Sack et al., 1992). Therefore, this patent covers any use of Clock, or its protein product, for the development or use of new techniques and/or pharmaceutical approaches for the treatment of blind people.

30. The light-dark cycle influences many functions of the retina including photoreceptor cells. Furthermore, the circadian clock regulates the timing of many genetic, molecular and cellular processes in the retina (Decker et al., 1995; LaVail, 1976; Young, 1980). Therefore, this patent covers any use of Clock, or its protein product, for the development or use of new techniques and/or pharmaceutical approaches for the treatment in any fashion of retinal dysfunction.

31. The circadian clock regulates a diurnal rhythm in mental and physical performance in animals, including humans (Benca, 1994; Monk et al., 1985; Richter, 1979; Turek and Van Cauter, 1994; Van Cauter and Turek, 1995). Therefore, this patent covers any use of Clock, or its protein product, for the development or use of new techniques and/or pharmaceutical approaches for enhancing human mental and physical performance.

32. Increased exercise at certain times of the day is known to be able to shift circadian rhythms that are controlled by the circadian clock (Van Reeth et al., 1994). Therefore, this patent covers any use of Clock, or its protein product, for the development or use of new techniques and/or pharmaceutical approaches that involve the use of exercise to shift or influence in any way circadian rhythms.

33. The disruption of normal circadian rhythmicity in intensive care facilities has been associated with decreased wellness and increased morbidity (Mann et al., 1986). Therefore, this patent covers any use of Clock, or its protein product, for the development or use of new techniques and/or pharmaceutical approaches for improving the environment of intensive care facilities or the health of the subjects such facilities.

34. The circadian clock plays a central role in the regulation of diurnal rhythms in plant and animal species that are of commercial value to humans (1988; Reiter and Follett, 1980). Therefore, this patent covers any use of Clock, or its protein product, for the development or use of new techniques and/or pharmaceutical approaches for enhancing the growth, development, performance, productivity, or health of such species, including those involved in the production of food for human consumption, as well as animal products used in producing apparel.

35. The circadian clock plays a central role in measuring the length of the day, which changes on an annual basis in all regions on earth outside of those close to the equator (1988; Reiter and Follett, 1980; Turek and Van Cauter, 1994). This seasonal change in day length influences the growth, development, health, reproduction, performance and productivity of many species, including humans (1988; Reiter and Follett, 1980; Turek and Van Cauter, 1994). Therefore, this patent covers any use of Clock, or its protein product, for the development or use of new techniques and/or pharmaceutical approaches for influencing any seasonal rhythms in any species, including the use of melatonin and/or melatonin related drugs to influence seasonal cyclicity.

36. The treatment of one sub-type of depression, referred to as Seasonal Affective Disorder (SAD), has been the exposure to extra bright light during the short days of winter (Penev et al., 1997; Terman, 1994; Wetterberg, 1994). Such treatment may be effective because of the effect of light on the circadian clock system. Therefore, this patent covers any use of Clock, or its protein product, for the development or use of new techniques and/or pharmaceutical approaches for the treatment of SAD or any other disorders that are associated with the seasonal change in daylength.

37. Since Clock is the first gene to be discovered and cloned in a mammal that is a component of the circadian clock, it will lead to the discovery of new Clock genes that have sequence homology with Clock and its protein product. Therefore, this patent covers any use of Clock, or its protein product, to discover and clone new genes, and their protein products by sequence homology (and their commercial value).

38. Since Clock is the first gene to be discovered and cloned in a mammal that is a component of the circadian clock, it will lead to the discovery of new Clock genes, and their protein products, that interact with Clock or the Clock protein product. Therefore, this patent covers the use of Clock, or its protein product, to discover new genes, and their protein products that are found by determining which genes and their protein products interact with Clock, and its protein product, in a functional way.

39. Since Clock is the first gene to be discovered and cloned in a mammal that is a component of the circadian clock, it will lead to the discovery of new Clock genes, and their protein products, that interact with Clock or the Clock protein product. Therefore, this patent covers the use of Clock, or its protein product to screen for molecules that may have sequence similarity or functional relationships to clock or its protein product.

40. The circadian clock regulates the timing of the expression of many genes and the production of their protein products (Jacobshagen and Johnson, 1994; Lausson et al., 1989; Loros et al., 1989; Millar and Kay, 1991; Taylor, 1989). Therefore, this patent covers any use of Clock, or its protein product, for the development or use of new techniques and/or pharmaceutical approaches in the use of gene therapy where a particular gene and/or its protein product needs to be under or over-expressed.

41. The circadian clock is a major regulator of the sleep-wake cycle and many pathological changes in the sleep-wake cycle are associated with circadian rhythm disorders (Kryger et al., 1994). Therefore, this patent covers any use of Clock, or its protein product, for the development or use of new techniques and/or pharmaceutical approaches for the discovery of genes and their protein products that are involved in the regulation of the sleep-wake cycle.

The Examples to follow illustrate particular embodiments of the present invention and are not limiting of the specification and claims in any way.

EXAMPLE 1

Isolation and phenotypic analysis of the mouse Clock mutation

Because orthologs of the canonical clock genes (period, timeless, and frequency) have not been found in mammals, and because other strategies to identify mammalian clock genes have not yet been successful, a mutagenesis screening strategy to isolate clock mutations in the mouse was initiated (Takahashi et al. 1994). Circadian behavior in the mouse is precise and easily quantitated, thus it is very well suited for genetic screening. Wild type C57BL/6J strain mice, which were used for this screen, exhibit a robust circadian rhythm of wheel running activity (Pittendnigh & Daan 1976, Schwartz & Zimmerman 1990). This behavioral assay was used to screen for mice carrying mutations that cause abnormal circadian periods in constant darkness. Because most clock mutations that have been isolated in other organisms have been semidominant (Hall & Kyniacou 1990, Dunlap 1993), dominant and semidommant mutations were screened for. Analysis of about 300 $G_1$ progeny of ENU-treated mice revealed one mouse that expressed a circadian period that was more than one hour longer than (and six standard deviations above) the normal period of 23.7 hours (Vitaterna et al. 1994). This long period phenotype was inherited as a single-locus, semidommant, autosomal mutation, which was designated Clock.

Mice homozygous for the Clock mutation expressed extremely long circadian periods of about 28 hours for the first two weeks of exposure to constant darkness, after which there was a complete loss of circadian rhythmically. The Clock gene, thus, regulates at least two fundamental properties of the circadian clock system: the intrinsic circadian period and the persistence of circadian rhythmicity. No anatomical defects in the SCN have been observed in association with the Clock mutation (Vitatema et al. 1994), which suggests that the loss of circadian rhythmicity in constant darkness cannot be attributed to a gross anatomical or developmental defect.

In addition to the effects on period and persistence of circadian rhythms in Clock mutants, at least two other circadian effects of the mutation have been documented. The period of Clock heterozygous mice is unstable and their free-running periods tended to lengthen with time in constant darkness. In addition, the photic entrainment of Clock heterozygotes is also altered. Clock/+ mice were able to entrain to 28-hour light cycles, while wild-type mice did not. Importantly, Clock/+ mice also exhibited high-amplitude phase-resetting responses to 6-hour light pulses (Type 0 resetting) as compared to wild-type mice which exhibited low amplitude (Type 1) phase resetting. Because of their loss of rhythmically in constant conditions, phase shifts in response to light pulses could not be measured in Clock/Clock homozygotes, but two findings indicate that these animals can entrain: the phase of a restored rhythm following a light pulse and the phase of the free-run following entrainment to a light dark cycle were both determined by the phase of the light signal. The increased efficacy of photic resetting stimuli and the decrease in period stability suggest that the Clock mutation may reduce circadian pacemaker amplitude in Clock heterozygotes.

To determine whether the Clock mutation affects other rhythms in mice, circadian drinking rhythms were measured. The Clock mutation affected the period and persistence of circadian drinking rhythms in a manner similar to that seen with activity suggesting that the mutation acts globally on rhythms in mice and is not restricted to locomotor activity.

The phenotype of Clock is as robust as the "best" clock mutations in Drosophila and Neurospora (Dunlap 1993). By robust is meant that the period change is on the order of 4 to 5 hours, which is followed by a complete loss of circadian rhythmicity. The magnitude of the period change in Clock homozygotes was equivalent to that seen with the $per^L$ and $frq^7$ alleles that also cause periods of 28–30 hours in their respective organisms (Dunlap 1993). The loss of circadian rhythmicity seen in Clock homozygotes resemble that seen in $per^0$ and $frq^9$ alleles, which are null mutations in those respective genes (Dunlap 1993). The robustness of Clock is important for two reasons. First, mutations that have modest effects on period length (on the order of a one-hour change in period in homozygotes) could be due to secondary effects of mutations on the circadian clock system. Second, the most robust mutants in Drosophila and Neurospora are found at the per, tim and frq loci, which are genes that appear to be critical and essential elements of the circadian mechanism in these organisms (discussed above).

EXAMPLE 2

Antimorohic Behavior of Clock Mutation

The initial analysis of the Clock mutation indicated that the mutation exhibited a semidominant phenotype (Vitatema et al. 1994). There are several possible causes of a semi-dominant phenotype, including the possibility that the mutation was induced in a gene that otherwise is not involved in the generation of circadian rhythms, but when mutated, interferes with the normal generation of these rhythms. To demonstrate that a particular gene is necessary for a particular biological process, one normally requires a loss-of-function allele of that gene leading to a loss of the phenotype in question. From genetic mapping (described below) it was found that Clock is contained within a radiation induced deletion on chromosome 5, $W^{19H}$, that includes the Kit (=W, Dominant White Spotting) locus (Lyon et al. 1984). This was found by mapping the SSLP content of $W^{19H}$ in ($W^{19H}$×Mus castaneous/Ei) $F_1$ progeny. Multiple genetic loci, mapping both proximal from and distal of Clock, are within the $W^{19H}$ deletion, indicating that Clock maps within this deletion. Access to this deletion that encompasses Clock allowed for further analysis of the phenotypic effect of this mutation. Muller's classic analysis of Drosophila mutations (Muller 1932), as well as more recent analysis of dominant mutations in Caenorhabditis elegans (Park & Horvitz 1986), provided a framework in which to analyze the Clock mutation. Muller described five types of mutant alleles, distinguished by manipulating the copy number of the mutant and wildtype alleles (via, e.g., deletions). These are hypomorph, amorph, hypermorph, antimorph, and neomorph alleles. The circadian phenotype of $W^{19H}$ heterozygous mice (hemizygous for the wild-type allele of Clock) is indistinguishable from the wild-type phenotype on a comparable strain background, indicating that the null allele of Clock is recessive to wild-type. By mating Clock/Clock mice to mice heterozygous for this deletion to generate $F_1$ progeny, it was possible to measure the phenotype of Clock/null animals (these $F_1$ animals are distinguishable from their Clock/+ litter mates by the presence of deletion-induced white coat color markings). Of particular intrest is the observation that the mean circadian period expressed by Clock/null animals (25.6±0.1.5 hours) is significantly longer than that of Clock/+ animals (24.2±0.05 hours, $p<10^{-7}$) This indicated that the wild-type allele interacts with the Clock mutation to ameliorate the severity of the Clock mutant phenotype. This is the essential feature of an antimorphic (Muller 1932), and is in contrast to what would be expected of a neomorph mutation, in which case the wild-type allele would have no effect on the expression or severity of the mutant allele. Furthermore, because $W^{19H}$ is large (~2.8 cM) and because multiple loci, both proximal from and distal of Clock, lie within the deletion, it appears unlikely that the breakpoints of the deletion interact directly with the Clock gene. That Clock is an antimorph (one type of dominant negative mutation) implies that the wild-type allele function in the normal generation of circadian rhythms in the mouse. This provides strong evidence that Clock defines a gene central to the mammalian circadian system.

The antimorphic behavior of the Clock allele provided clues about the nature of this mutation. Antimorphic behavior suggested that the mutant allele generates a molecule that competes with the wild-type function. This, and the observation that Clock/deletion and Clock/+ have much more severe phenotypes that +/deletion, allows the conclusion that the Clock mutation is unlikely to be either a null mutation (amorph), or a partial loss of function (hypomorph). Further, because +/deletion has no phenotype different from wild-type, the Clock phenotype does not appear to be the result of haplo-insufficiency. Perhaps most important, it is likely that the mutation conferring the altered behavior in Clock mutant mice may affect the coding sequence of the gene, due to its ability to interfere with the function of the wild-type allele.

EXAMPLE 3

Genetic Mapping of Clock

The first step in the molecular identification of Clock locus was to map its location in the mouse genome. Given the extensive genetic mapping information available in the mouse (Takahashi et at. 1994), it was possible to map Clock rapidly by linkage analysis using intraspecific mapping crosses and simple sequence length polymorphisms (SSLPs) from the MIT/Whitehead Institute genetic map (Vitaterna et al. 1994). Clock mapped to the mid portion of mouse chromosome 5 between two SSLP markers, D5Mit24 and D5Mit83, in a region that shows conserved synteny with human chromosome 4. The possibility of a human homolog of Clock on chromosome 4 is significant because it allows for focusing attention upon this region of the genome for possible linkage to circadian traits in human subjects as well as providing a candidate gene for other disorders associated with circadian rhythm dysfunctions such as delayed sleep phase syndrome (Vignau et al. 1993) and affective disorders (Wehr & Rosenthal 1989).

In order to identify a more precise chromosomal region in which to focus physical mapping and molecular cloning efforts, a high-resolution genetic map of the Clock region was genereated using SSLPs and 1804 meioses obtained from 6 intraspecific and 2 interspecific crosses. This SSLP mapping placed Clock close to the Kit (=W, Dominant white spotting) locus (Geissler et al. 1988b). High resolution genetic mapping, with a PruII RFLP identified using a Kit cDNA probe, placed Kit 0.7 cM (7 recombinants/988 meioses) proximal from Clock.

Using additional SSLP markers on a total of 2681 meioses, Clock has now been placed within a 0.3 cM interval, approximately 0.2 cM (5 recombinants/2681 meioses) distal of D5Mit307 and 0.1 cM (1 recombinant/ 845meioses) proximal from D5Mit/D5Mit306 (see FIG. 1). The location of this distal recombination has been confirmed in test-cross progeny.

EXAMPLE 4

Physical Mapping of the Clock Region

Figure 2:
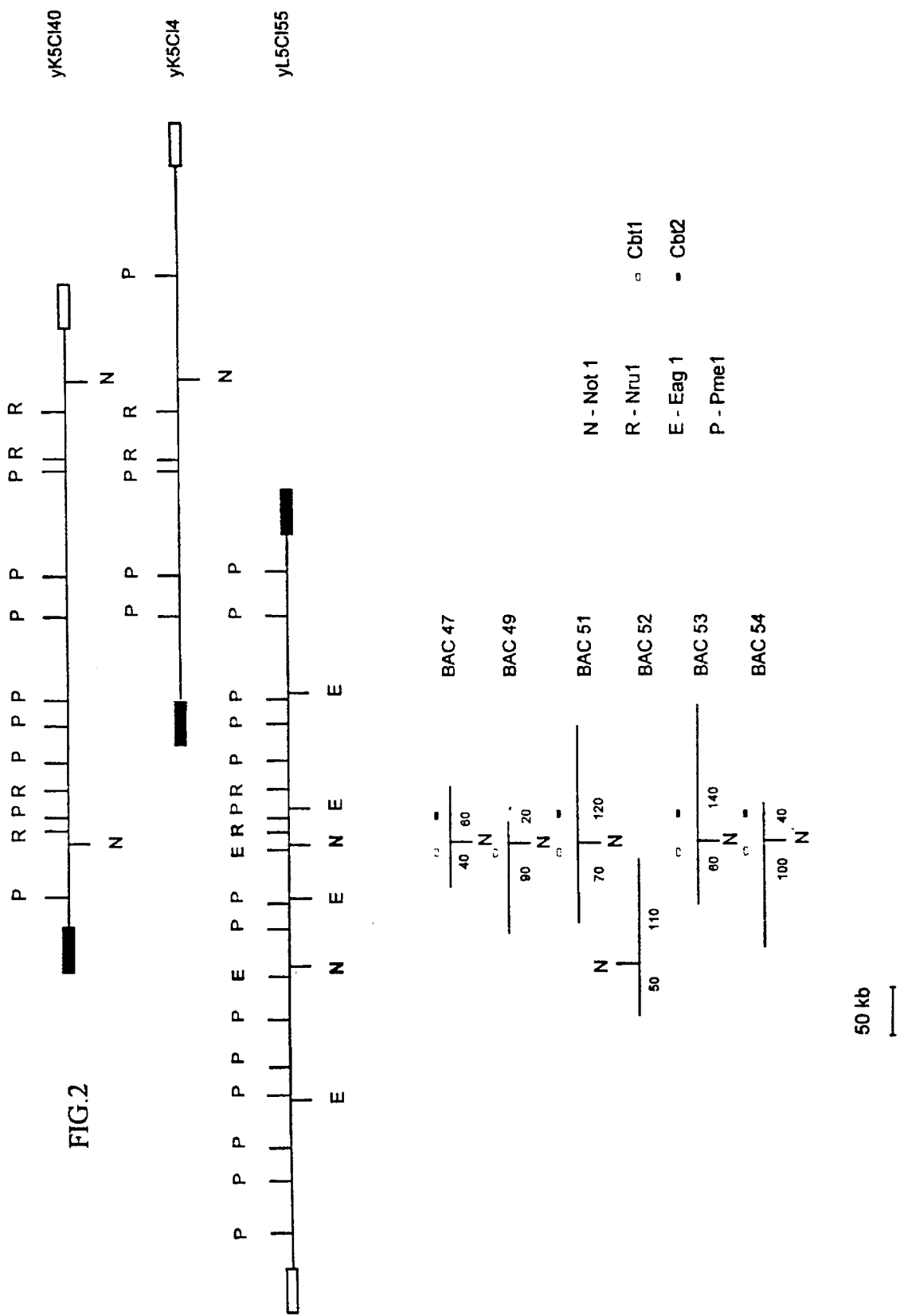
FIG. 2 is a schematic illustration of restriction mapping of YAC and BAC clones in the Clock region.

Based upon the high-resolution genetic map of the Clock region, a physical map which spanned the critical genetic region that must contain Clock (D5Mit307 - D5Mit112) was constructed. To do this, yeast, artificial chromosome (YAC) clones that map to the region were isolated. Using a YAC library that has been pooled for PCR screening (Kusumi et al. 1993), and SSLP markers, as well as sequence tagged sites (STSs), from the region surrounding Clock, over 40 YAC clones were isolated and a contig of ~4 Mb that spans the Clock region (FIG. 1) was constructed. YAC clones within the critical region were characterized by end cloning and long-range restriction mapping with pulse field gel electrophoresis (PFGE). Three nonchimeric YAC clones were identified and one of these YACs, which is 930 kb, contains both flanking markers and therefore must contain Clock. Long-range restriction mapping of the reduced genetic interval D5Mit307 - D5Mit112 indicated that it was about 400 kb in length (See FIG. 2). Most of this 400 kb critical region was then re-cloned in bacteria artificial chromosome (BAC) clones. BACs, which are intermediate in size (~100–200 Kb) between YACs and cosmids, have several advantages when compared to YAC clones. Although they are generally smaller than YAC clones, BACs are rarely chimeric, they are circular clones, thus they are much easier to manipulate, and they rarely suffer recombination or deletion damage (Shizuya et al. 1992). Using direct sequencing of the ends of the BAC clones, 12 BACs were placed on the YAC physical map using STSs. Subclone libraries from these BAC clones were placed to isolate 7 new SSLP markers. One of these markers, D5NWU1 was non-recombinant with Clock, and a second marker, D5NWU2, defined the closest distal recombinant with Clock on the genetic and physical map. Thus the critical region containing Clock was now defined by the flanking markers D5Mit307 and D5NWU2 which defined an interval less than 400 kb.

EXAMPLE 5

Transcription Unit Analysis in the Clock Region

Within the critical region containing Clock there are no known candidate genes that have previously been identified. Therefore three different approaches identifying candidate genes were initiated: 1) direct screening of SCN cDNA libraries with BAC clones as probes; 2) hybridization selection of cDNAs from SCN libraries using BAC clones as driver; and 3) shotgun sequencing random M13 libraries made from BAC clones.

The first two of these methods used a pair of oligo dT primed cDNA libraries. Tissue derived from mouse SCN region was microdissected from a total of about 100 mice at four different circadian time points (circadian time (CT) 1,7,13, and 19). For one of these libraries, poly $A^+$RNA was extracted from SCN tissue collected in constant darkness at each time point. For the other library, poly $A^+$RNA was extracted from SCN tissue collected at the same four time points: however, the animals were previously exposed to a 30 to 90 minute pulse of light. CDNA libraries were directionally cloned using the ZAP Express lambda vector (Stratagene). Primary library sizes were $1.7 \times 10^6$ and $1.2 \times^6$ pfu, and $1 \times 10^6$ clones from each library were plate amplified. Average insert sizes were 2.3 and 2.2 kb and raged from 600 to 5200 bp. These cDNA libraries are important resources because the SCN is very small (about 16–20,000 neurons or ~20 g protein per mouse) and is difficult and expensive to obtain high quality mRNA samples.

A. Direct screening of the cDNA libraries using whole BAC inserts.

Figure 3:
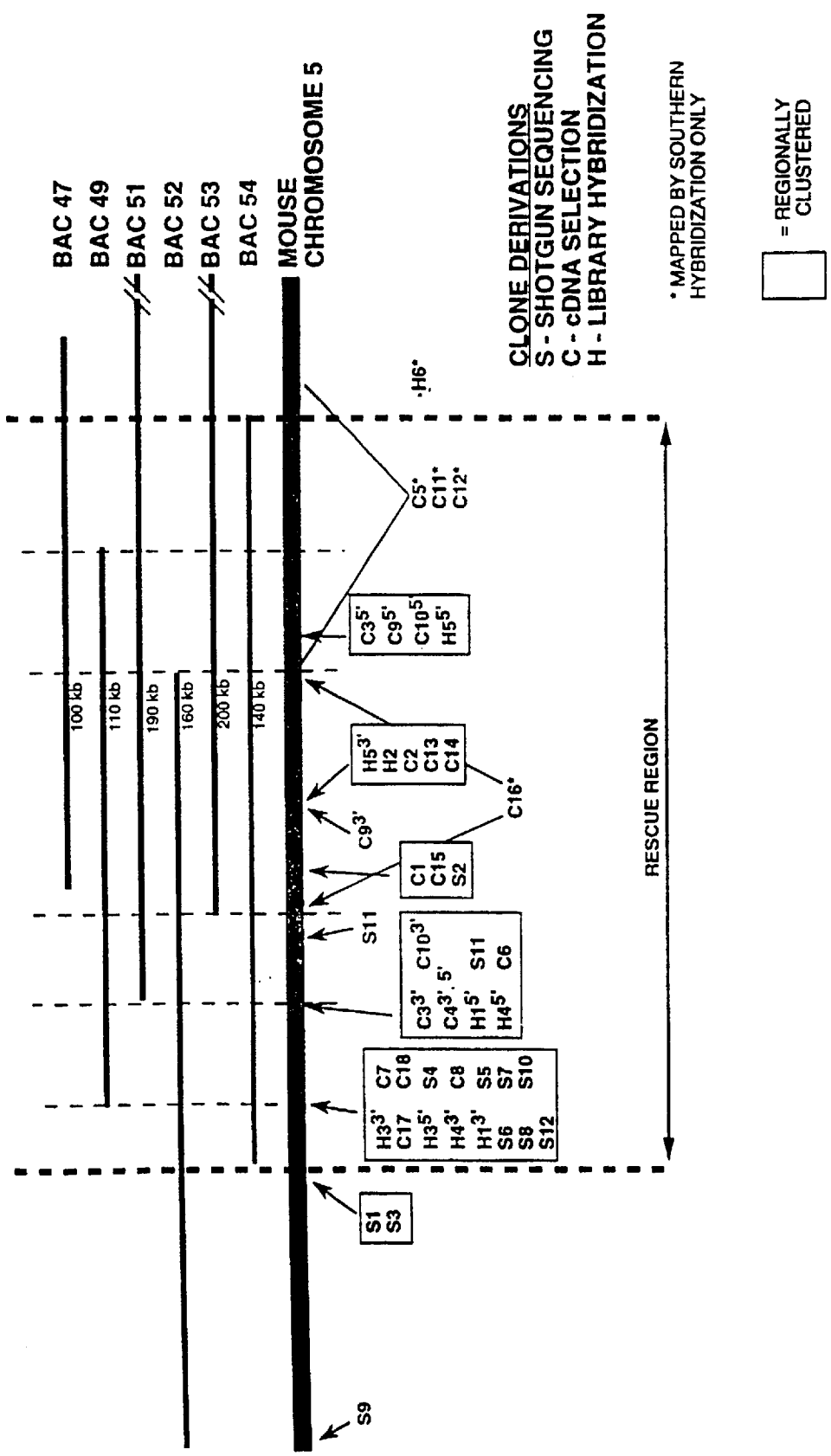
FIG. 3 is a schematic illustration of a transcript map of the Clock region.

Two different BAC clones were used which together cover >¾ of the critical region containing Clock. BAC DNA for probes was purified by restirction digest with Not I to release inserts and separation of field inversion gel electrophoresis (FIGE). BAC insert DNA was radiolabeled using random priming and the probe was preannealed with Cot-1 mouse DNA to suppress repetitive DNA sequences using methods similar to those developed for probes from entire YAC clones (Marchuk & Collins 1994). The cDNAs identified using the method were characterized in two ways. The ends of the clones were sequenced and these sequences were used to search the DNA and protein databases, using the Basic Local Alignment Search Tool (BLAST) (Altschul et al. 1990). Also, these cDNA clones were used as probes on a Southern blot consisting of BAC clones, restriction digested with HindIII, that map to the critical genetic region. Using these two methods, it was possible to eliminate false positive clones by identifying clones containing repetitive sequences (e.g., L1 elements) and clones that did not map to the critical genetic region (i.e., they did not hybridize to the BAC clone Southern blot). This process led to the identification of fifteen cDNA clones that fell into 6 classes of cDNA clones mapping in the Clock region. These 6 classes of clones are referred to as "H1 through H6" in (See FIG. 3).

B. cDNA selection experiments.

The second method used to identify transcription unit sequences was an adaption of the cDNA selection protocol described by Lovett (Lovett 1994). For these experiments, SCN cDNA from lambda DNA was prepared from plate lysates from the SCN libraries described above. Lambda DNA from the cDNA library (instead of excised phagemid DNA) was used because the purification of cDNA inserts were excised by digestion with BamHI and XhoI and gel purified from lambda vector arms. cDNA was then digested with DpnII, and BamHI adapters form the representational difference analysis (RDA) method (Lisitsyn et al. 1993) were ligated. Amplicons from the cDNA fragments were then made by PCR as described in the RDA procedure. Genomic DNA from BAC clones was released with Not I digestion and inserts were purified on pulse-field gel electrophoresis (PFGE). BAC DNA was the digested with Sau3AI, and a different set of BamHI RDA adapters was ligated. Amplicons from the BAC DNA were then made by PCR using a biotin end-labeled oligonucleotide primer. cDNA and BAC amplicons were then hybridized in the presence of Cot-1 mouse genomic, ribosomal and vector DNA to suppress background. Hybrids were then captured with streptavidin-coated magnetic beads as described by Lovett. Two rounds of selection were performed and the efficiency was monitored with a positive control (spiked with c-fos clone), a negative control (jun-B) and Cot-1 DNA level.

Selected clones were then eluted and cloned into pBluescript vector. Clones were then picked into six 96-well plates. Replica filters were made and screened with the following probes: BAC 51 (positive probe), BAC 48 (negative probe), c-fos, and Cot-1 DNA. Clones that were positive for BAC 51 and negative for the other three probes were analyzed. Sixty cDNA such clones were selected. These 60 selected clones were then sequenced to identify duplicates and tested for mapping back to the Clock region on Southern blots of HindIII digested BAC clones from the critical region. Out of the 60 clones, 38 appeared valid by sequence, 14 had repetitive sequences and 8 were false positives (ribosomal or vector DNA). All 38 clones mapped to the Clock region BAC Southern blots. The selected cDNA fragments appeared to fall into about 13 classes. These fragments were then used to screen the SCN libraries to obtain longer cDNA clones. Eighteen cDNA clones that mapped to the region on by Southern blot were obtained (these clones are referred to as "C1 through C18" in FIG. 3), and these clones fell into 10 different classes of clones.

C. Shotgun sequencing of BAC clones.

In addition to the cDNA-identifying approaches described above, random sequencing of genomic DNA were used as a third method of transcription unit analysis. With this approach: 1) a genomic scaffold (i.e., one to two-fold coverage of the region) could be used for sequenced-tagged site (STS) mapping and for finer mapping of cDNAs isolated by the first two techniques (as opposed to mapping by BAC Southern); 2) database searches using genomic sequence could identify cDNAs not found by direct screening and cDNA selection; and 3) genomic sequence would uncover new SSLP markers that could further diminish the region containing Clock. Upon further consideration, selected BACs were sequenced to completion. Complete genomic sequence allowed precise mapping of STSs, exon mapping of cDNA clones, promoter analysis, and interpretation of other experiments such as BAC rescue and Southern blot analysis.

Two parametes are critical for successful shotgun sequencing project: extremely pure source DNA and a high-throughput/low-cost template preparation protocol. Two independent shotgun libraries using two BACs, which together covered about ⅔ of the Clock critical region were constructed. BAC DNA was prepared by large-scale alkaline lysis of two-liter liquid cultures followed by a two-step CsCl gradient purification using methods adpated from the *C. elegans* genome project (Favello et al. 1995). The second CsCl purification of plasmid (BAC) DNA was necessary to ensure low *E. coli* chromosomal DNA contamination. The protocol typically yielded 5–15 µg intact BAC DNA from two liters of liquid culture. 5 µg DNA were sonicated, blut-ended, and run on an agarose gel for size selection of insert DNA. The 1.3–1.7 kb range was gel-purified and blut-end ligated into M13. Ligation products were electroporated into *E. coli* XL1 Blue MRF' and plated; 25-fold dilution of the ligation mixture was necessary to prevent arcing during electroporation. Clear plaques were picked into SM buffer for storage.

High-throughput M13 template preparation was essential for efficient BAC sequencing. Probability theory indicates that 4× coverage of a length of DNA is necessary to achieve 98% of the complete sequenc. The number of templates needed to achive "n"× coverage is defined as n*total length of DNA/sequenced length per template Knowing the length of the BAC DNAs (160 kb and 140 kb) and assuming 500 bases of good sequence per template, 1280 templates and 1120 templates, respectively, were needed to reach 4× coverage of each library. A magnetic bead isolation protocool adapted form Hawkins et al. (1994) in a 96-tube format was used to rapidly prepare sequence-ready M13 template. 650 µl M13 cultures were grown in 96-tube racks. Cultures were centrifuged, lysated were transferred to new tubes, and DNA was released by heat/detergent lysis of M13 protein coats. Magnetic beads and hybridization solution (2×stock: 26% PEG 8000, 20 mM $MgC_{12}$) were added to the tubes for selective DNA hybridization to the beads. The beads were magnetically collected and supernatant was discarded. DNA was eluted with water; the beads were magnetically collected, and the DNA was transferred to a 96-well plate for storage. This protocol typically yielded 1–2 µg sequencing template per sample; 192 templates could be prepared in about 5 hours. Fluorescence cycle sequencing was performed by an ABI PRISM Turbo 800 Molecular Biology LabStation with -21 M13 Dye Primer chemistry, and the products were run on an ABI PRISM 377 DNA sequencer. The Sequencher program (Gene Codes) removed vector sequence and low-quality sequence from each shotgun sequence and then aligned the sequences into contigs. Average sequence length was 580 bases. Each sequence was used to search BLAST databases (BLASTN-nr, BLASTN-dbEST, BLASTX-nr, and TBLASTX-dbEST) to identify Clock candidates by gene, EST, or protein homology. In addition, various gene finding programs were also used.

The 160 kb BAC was sequenced to 4x coverage and aligned into about 20 contigs of 4–30 kb each. Clones that defined the ends of contigs were selected for "reverse sequencing", where the opposite end of the 1.5 kb inserts was sequenced by M13 Reverse Dye Primer chemistry in an attempt to join contigs. This approach reduced the number of contigs to 12, and more importantly, it provided enough information to order all contigs by STS alignment. The 140 kb BAC has been sequenced to 3x coverage so far, and its region overlapping the 160 kb BAC provided sufficient information to reduce the number of contigs in the latter to five. Extensive sequencing of these two BACs in the Clock critical region has proven to be extremely informative: all cDNAs isolated by direct screening and by cDNA selection were physically mapped, and additional Clock candidates identified by sequence homology (designated S1 through S12 in FIG. 3). The genomic sequence provides critical information for analysis of transcription units (such as identification of exon boundaries), interpretation of BAC rescue experiments, and Clock mutation identification and analysis.

EXAMPLE 6

Transgenic mouse expression of BAC clone and phenotypic rescue of Clock

Because the mutation was a point mutation induced by ENU, a second parallel approach using transgenic rescue to clone the Clock gene was undertaken. Transgenic mice were made by injecting BAC DNA from the clones that mapped to the Clock region. Three sets of DNA preparations were used: 1) circular full-length BAC 54 (140 kb); 2) linear NotI fragment of BAC54 (100 kb); and 3) circular full-length BAC 52 (the clone that overlaps with BAC 54 by~90 kb. Circular DNA was purified using alkaline lysis and cesium chloride gradient ultracentrifugation protocol described for the cosmid DNA purification with some modifications (Favello et al. 1995). The 100 kb linear NotI fragment of BAC 54 was gel-purified using pulse-field gel electrophoresis.

Figures 1, 4:
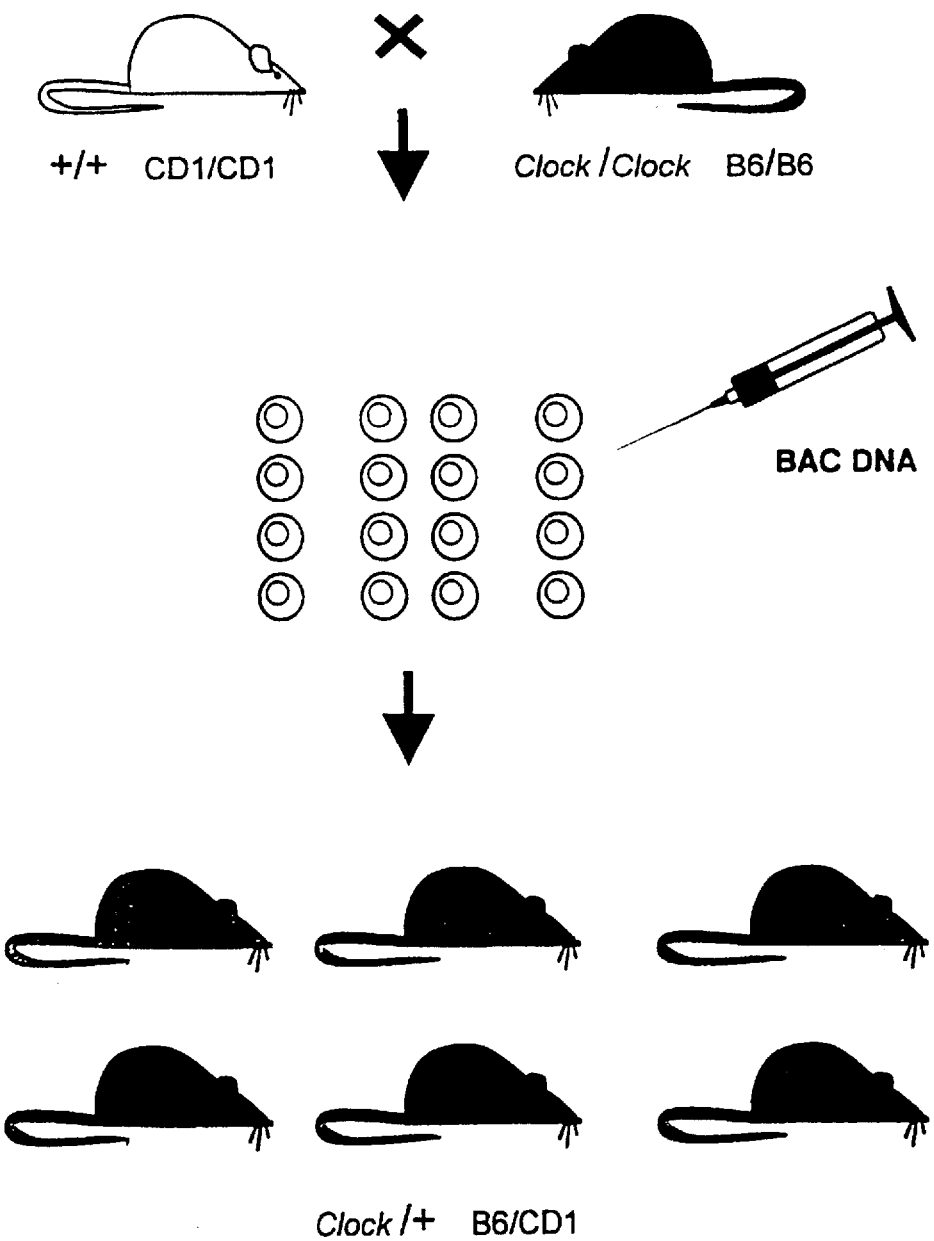
FIG. 4 is a schematic illustration of the breeding strategy used to produce and rescue Clock mutants.
Figures 2, 4:
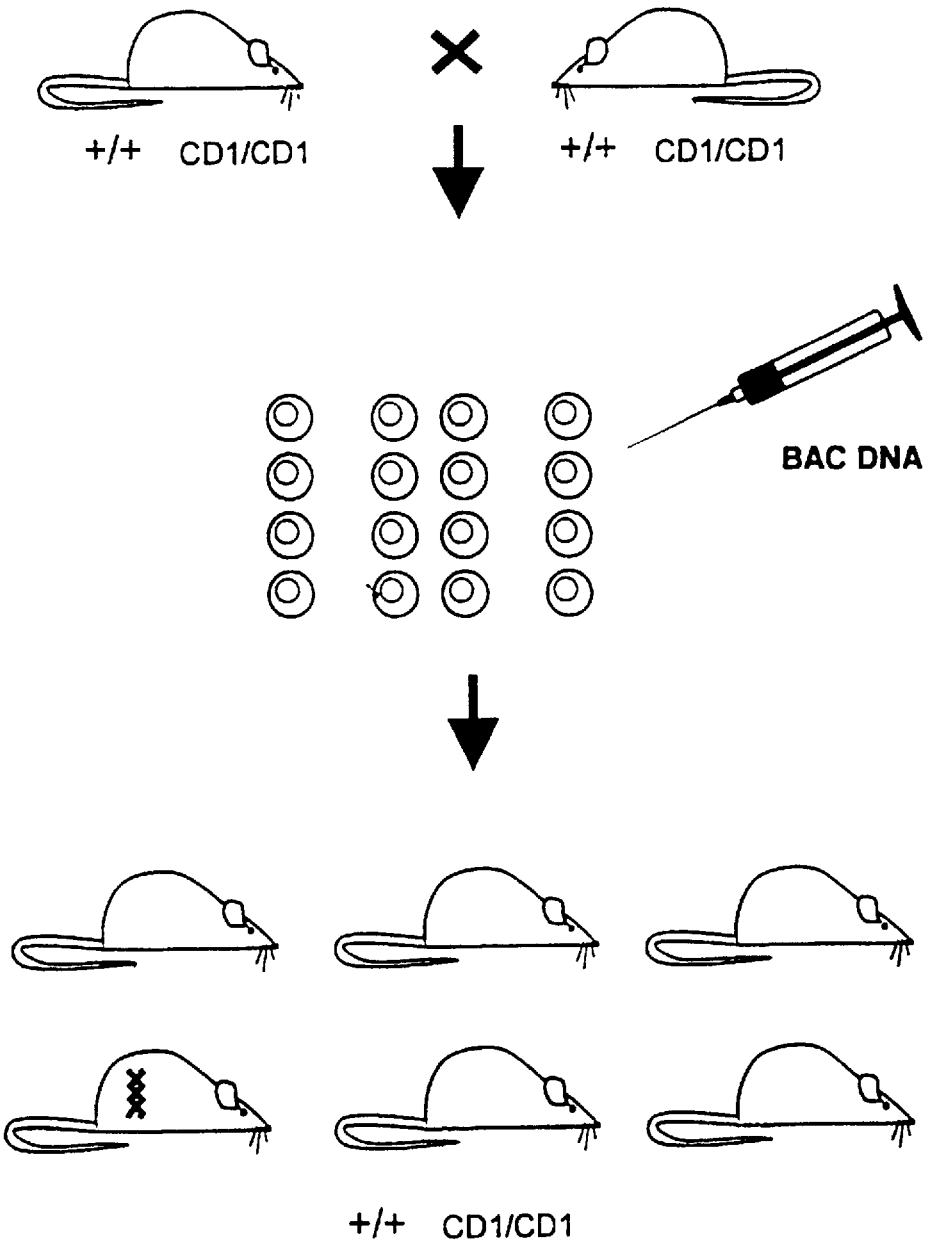

Isolated BAC DNA was injected at a concentration of 1 μg/μl into fertilized mouse oocytes isolated from crosses between either CD1 +/+ females and (BALB/cJxC57BL/6J) F2 Clock/Clock males or CD1 +/+ females and CD1 +/+ males as described previously (See FIG. 4) (Hogan et al. 1994). Transgenic mice were identified both by PCR and Southern blot analysis of the genomic DNA prepared from tall biopsies as described (Hogan et al. 1994). Out of 64 mice born from the BAC54 injected embryos, 6 were positive for the transgene by both methods. Four mice out of 54 were positive for the 100 kb linear fragment of BAC 54, and 2 out of 12 born were positive for BAC 52 DNA (See Table 2).

TABLE 2

Summary of BAC Transgenic Mice Lines

| Transgenic line | Founder genotype | DNA injected | Transgene copy number | Transmitance |
|---|---|---|---|---|
| TG14 | Clock/+ | BAC54 circular DNA, 140 kb | 2–3 | 50% |
| TG36 | Clock/+ | BAC54 circular DNA circular k-b | 3–4 | 50% |
| TG55 | +/+ | BAC54 circular DNA circular kb | 8–10 | 50% |
| TG60 | +/+ | BAC54 circular DNA, 140 kb | 1 | 50% |
| TG19 | +/+ | BAC54 circular DNA, 140 kb | N/D | 50% |
| TG48 | Clock/+ | BAC54 circular DNA, 140 kb | N/D | 13% |
| TG80 | +/+ | BAC54 100 kb linear Not1 -fragment | 2–3 | 50% |
| TG97 | | BAC54 100 kb linear Not I -fragment | 10–12 | 50% |
| TG98 | +/+ | BAC54 100 kb linear Not1 -fragment | ND | 50% |
| TG191 | Clock/4 | BAC54 100 kb linear Not1 -fragment | ND | 10% |
| TG121 | Clock/+ | BAC52 circular DNA,160 kb | 1 | 50% |
| TG126 | Clock/+ | BAC54 circular DNA, 160 kb | 4–5 | 50% |

Mice postive for the transgene integration by both methods were crossed to either Clock/+ females (for male founders ) or Clock/Clock males (for female founders). F1 progeny from these crosses were 1) tested for the presence of the transgene, 2) genotyped for Clock locus by flanking SSLP markers, and 3) wheel-tested for circadian phenotype as described previously (Vitaterna et al. 1994). Results of the phenotypic assay are summarized in Table 3. Circadian period length from each mouse was calculated for the 20-day interval during the exposure to constant darkness by a $Chi^2$ periodogram analysis.

Four lines generated from BAC 54 injections (TG14, 36, 55, 60) showed complete rescue of the Clock mutant phenotype both in heterozygous and homozygous Clock mutant animals. An example is provided for line TG36 which is representative of this group. The breeding scheme used in the experiment in shown in FIG. 5. Activity records showed the phenotypic rescue with BAC 54 transgene in Clock homozygotes. As described above, the Clock mutation has been shown to lengthen circadian period by 1 hr in heterozygotes and by 4 hr in homozygotes. All transgenic animals that were genotyped as Clock/+ or Clock/Clock from these four lines showed a circadian period similar to wild type (Table 3). This result demonstrates that the Clock gene is localized within the 140 kb BAC clone.

To reduce this interval to a single gene, the transgenic functional assay was performed with a smaller DNA fragment (BAC 54 100 kb linear fragment) and an overlapping BAC clone (160 kb BAC 52 clone). Both of these genomic fragments failed to rescue the Clock mutation (Table 3).

TABLE 3

Period Estimates

| Trasgenic Line | +/+ | ++/tg | Clock/+ | Clock/+ tg | Clock/Clock | Clock/Clock tg |
|---|---|---|---|---|---|---|
| TG14 | N/A | N/A | 24.22 ± 0.183 n = 5 | 23.08 ± 0.146 n = 7 | 27.06 ± 0.314 n = 7 | 23.27 ± 0.099 n = 9 |
| TG36 | 23.48 ± 0.048 n = 11 | 22.89 ± 0.05 n = 10 | 24.18 ± 0.053 n = 20 | 23.21 ± 0.047 n = 20 | 27.36 ± 0.282 n = 8 | 23.18 ± 0.082 n = 14 |
| TG55 | 23.41 ± 0.091 n = 10 | 22.92 ± 0.137 n = 8 | 24.12 ± 0.21 n = 8 | 22.77 ± 0.099 n = 7 | N/A | N/A |
| TG60 | N/A | N/A | 23.91 ± 0.1 n = 13 | 23.13 ± 0.122 n = 6 | N/A | N/A |
| TG80 | 23.44 ± 0.101 n = 18 | 23.50 ± 0.07 n = 5 | 23.92 ± 0.125 n = 19 | 23.64 ± 0.083 n = 4 | N/A | N/A |
| TG97 | N/A | N/A | 23.93 ± 0.04 n = 4 | 26.67 ± 0.065 n = 7 | N/A | N/A |
| TG121 | 23.50 ± 0.142 n = 4 | 23.66 ± 0.125 n = 2 | 23.99 ± 0.11 n = 13 | 23.96 ± 0.032 n = 5 | 26.83 ± 0.4 n = 2 | 26.87 ± 0.161 n = 4 |

Taken together, the results from all of these transgenic rescue experiments are consistent with only a single gene in the 140 kb BAC clone which we describe below.

EXAMPLE 7 mRNA Expression, Sequence and Structure of the Clock Gene

The mRNA expression of candidate genes was screened by Northern analysis in Clock mutant vs. wild-type mice. This led to the observation of reduced mRNA expression of a candidate M13 clone with a PAS domain sequence first recognized by shotgun sequencing. This M13 genomic clone contained exons from a transcription unit that we subsequently identified as the Clock gene. There are two major transcripts from the Clock locus of ~8 and ~11 kb (using the cDNA clones, YZ50 or YZ54, as a probe on Northern blots). There was a reduction in the abundance of both transcripts in the hypothalamus and eye of homozygous Clock mutants as compared to wild type mice. In addition, there was also a diurnal rhythm in the level of Clock mRNA in wild-type mice in both the hypothalamus and eye with high levels in the day and low levels at night. This rhythm in Clock mRNA is consistent with the presence of circadian oscillators in both of these tissues (i.e., the suprachiasmatic nucleus and retina). In situ hybridization revealed that the expression of Clock mRNA is enriched in the SCN with lower levels in other regions of the brain. Taken together the reduced mRNA expression in Clock mutants, the diurnal rhythm in mRNA abundance in the hypothalamus and the eye, and the enrichment of mRNA expression in the SCN all strongly suggested that this candidate gene encoded Clock. No other candidate genes revealed any changes in mRNA expression on Northern blots. This led to further analysis of this PAS domain candidate gene including the elucidation of the entire gene, analysis and the exon-intron structure of the gene, sequencing of cDNA clones expressed from the gene, identification of coding sequence of cDNA clones expressed from the gene, identification of the coding sequence and deduced amino acid sequence of the CLOCK protein.

Figure 6:
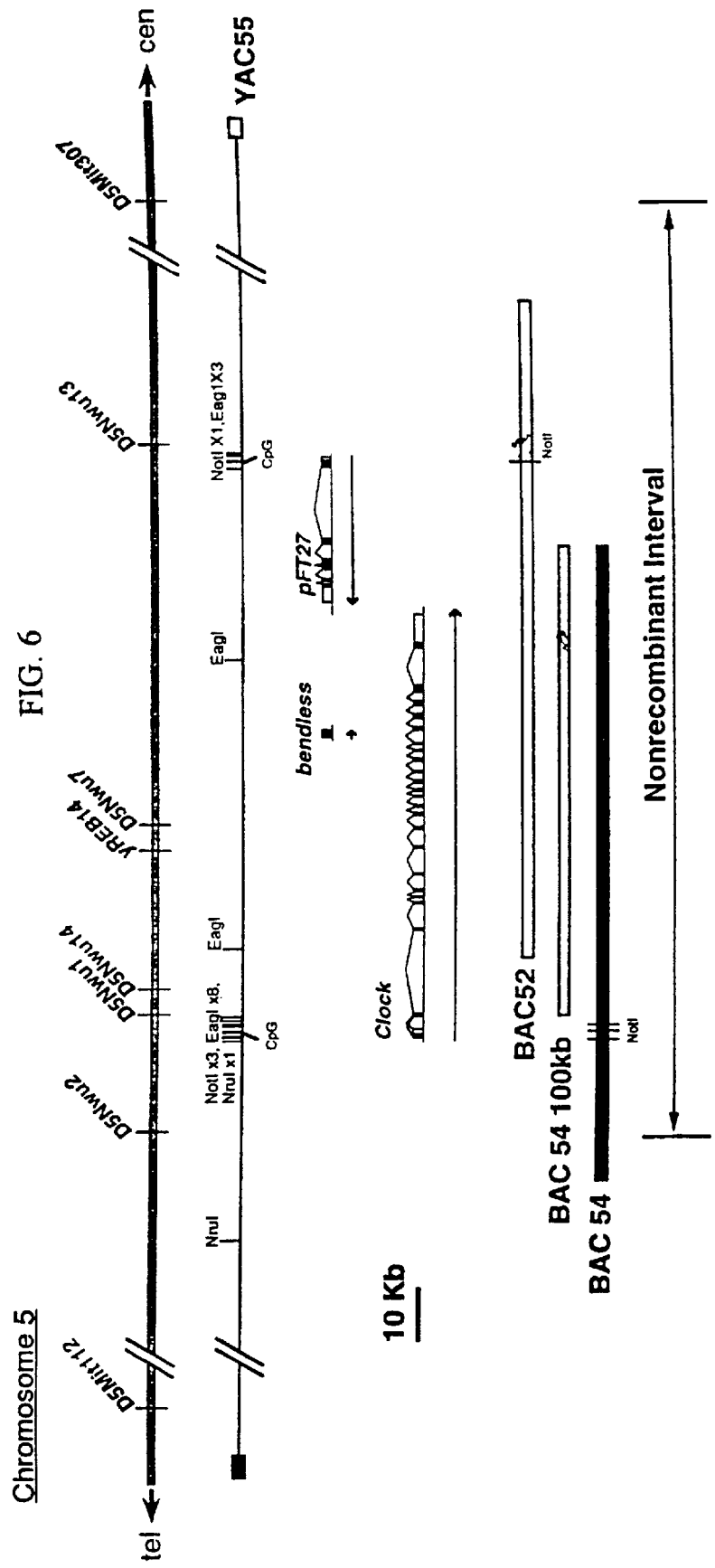
FIG. 6 is a schematic illustration of the physical location of the Clock gene.

FIG. 6 shows a diagram of the physical extent and location of the Clock gene. Based on a set of 10 classes of cDNA clones from the gene, the transcribed region of the Clock gene spans over 90 kb of genomic sequence and contains 24 exons. Two of the exons (exons 1A and 1 B) are distal to the NotI site in BAC54, and thus the 100 kb fragment from BAC 54 and 160 kb clone of BAC 52 do not contain the 5' region of the Clock gene. Because of its substantial size, the Clock gene is the only transcription unit in BAC 54 that can account for the results of the transgenic rescue experiments. Based upon the physical location of this gene and the rescue experiments, we can conclude that this candidate gene encodes Clock.

Figure 7:
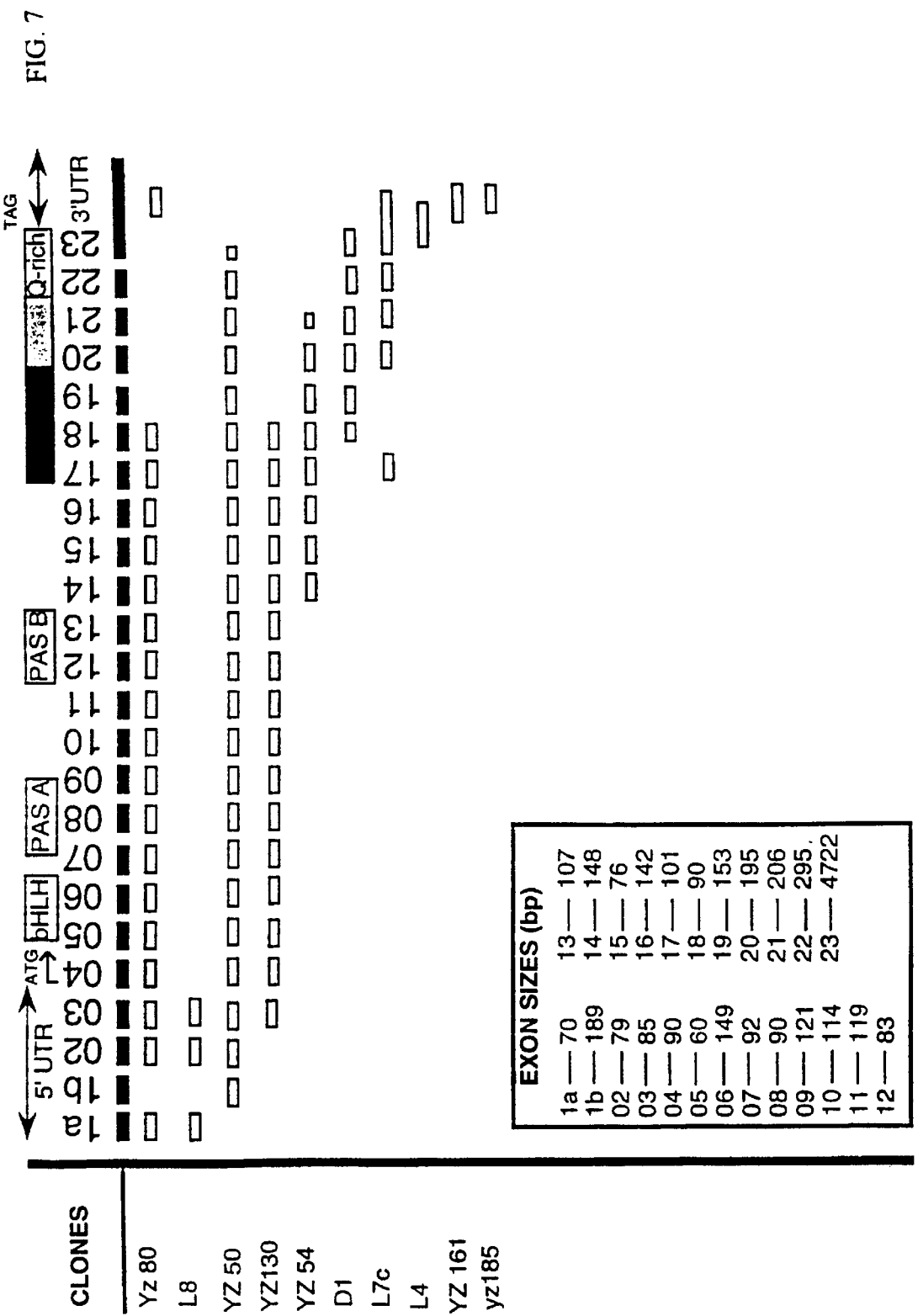
FIG. 7 shows the exon structure of the Clock gene and the exon content of different cDNA clones FIG. 8 (in three panels, 8-1, 8-2 and 8-3) shows the complete nucleotide sequence of the Clock gene based upon genomic exon sequences. The nucleotide sequence of the Clock gene is designated SEQ ID NO:1 and the deduced amino acid residue sequence of the CLOCK polypeptide is designated as SEQ ID NO:2.

The exon structure of Clock is shown in FIG. 7. Ten classes of cDNA clones have been found. There is alternative use of exons 1A and 1B in clones YZ50, L8 and YZ80. In addition there is alternative splicing of exons 18 which can be seen in clone L7c, which also has a deletion of exon 19 caused by the Clock mutation (described below)

The complete nucleotide sequence of Clock based upon genomic exon sequences is shown in FIG. 8 (8-1, 8-2, 8-3). The sequences of individual exons are shown in FIG. 9 (9-1, 9-2, 9-3, 9-4). The splice donor and acceptor site sequences are shown for the intron/exon boundaries in FIG. 10. There is an open reading frame of 2568 base pairs between nucleotides 389 and 2953 which encodes a 855 amino acid conceptually translated protein (called CLOCK). Following the coding sequence, which terminates with a TAG codon in Exon 23, there is a very long 3' untranslated sequence that terminates at ~7500 bp (defined by a subset of cDNA clones with poly A tails at this location), and additional 3'untranslated sequence that continues for another ~2500 bp to form a second transcript of ~10 kb. The 7.5 kb and 10 kb transcripts based on cDNA and genomic sequence correspond well with the ~8 kb and ~11 kb mRNA transcripts estimated from Northern blots.

Figure 11:
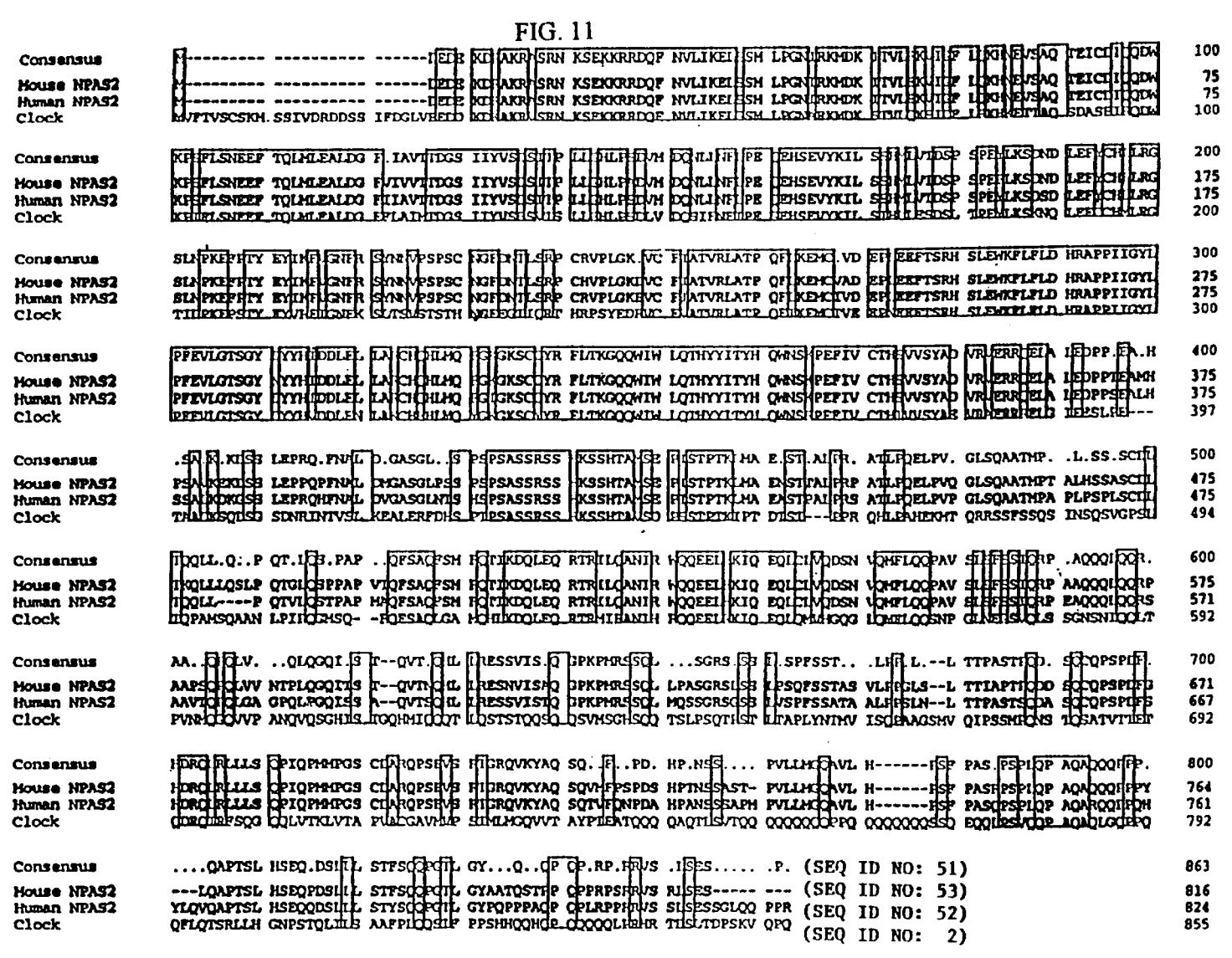

The Clock gene encodes a member of the basic helix-loop-helix (bHLH) ~PAS domain family of proteins. A search of the NCBI database using BLASTN shows that the Clock nucleotide sequence is most similar to human MOP4 (68% identical), human N-PAS2 (69% identical) and mouse NPAS2 (67% identical). A search of the NCBI database with the conceptually translated protein sequence using BLASTX shows a similarity to these same three proteins as well as weaker similarity with a large number of bHLH-PAS proteins. An amino acid alignment of CLOCK with human NPAS2 and mouse NPAS2 is shown in FIG. 11. There is sequence similarity among the three proteins in the basic helix-loop-helix domain as well as the entire PAS domain. In addition, there are serine-rich and glutamine-rich regions that are well conserved in the midportion and C-terminal region of the proteins. Unlike NPAS2, however, CLOCK has a poly-glutamine stretch near the C-ternnus.

In the sequence of the mutant Clock allele, there is a single nucleotide base substitution from A to T that alters the third position of the 5' (donor) splice site of exon 19. This changes the consensus sequence at this splice site from gt a to gtt, which is known in the art to cause exon skipping (Krawczak, M., J. Reiss, D. N. Cooper, *Human Genetics* 90:41 –54, 1992). As shown in FIG. 10, 20 out of 22 donor splice sites in the Clock gene have the consensus sequence gta and the remaining 2 sites are gtg, which is also consistent with a purine at the third position. The A to T point mutation in the mutant Clock allele is consistent with that expected from an ENU-induced mutation (Provost and Short, 1994). In the case of Clock this leads to a deletion of exon 19. The deletion of exon 19 causes a deletion of 51 amino acids (corresponding to amino acids numbers 514 to 564 in SEQ ID NO:2). FIG. 12 shows the amino acid sequence of CLOCK with the bHLH, PAS-A and PAS-B domains as well as the deletion in the mutant. FIG. 13 shows the exon 18 alternatively spliced version of a Clock, which leads to removal of 30 amino acids (corresponding to amino acids numbers 484 to 513 in SEQ ID NO:2). Both the wild-type and mutant versions of the Clock mRNA and protein, express an isoform missing exon 18. Thus, at least 4 different coding versions of CLOCK have been identified.

The deduced amino acid sequence of the Clock gene product provides insights about its function as a transcription factor. The basic region of the bHLH domain is known to mediate DNA binding and shows that CLOCK likely interacts directly with DNA. The HLH and PAS domains are each known to be protein dimenization domains and predict that CLOCK can interact directly either with itself or with other bHLH or PAS proteins. The C-terminal region of CLOCK has a number of glutamine-rich, proline-rich and serine-rich stretches that are characteristic of activation domain transcription factors.

The disclosures listed below and all other disclosures cited herein are incorporated into the specification by reference.

Altschul, S. F., W. Gish, W. Miller, E. W. Myers, D. J. Lipman. 1990. Basic Local Alignment Search Tool. *J Mol. Biol.* 215:403–410

Aronson, B. D., K. A. Johnson, J. J. Loros, J. C. Dunlap. 1994. Negative feedback defining a circadian clock: autoregulation in the clock gene frequency. *Science* 263:1578–1584

Baylies, M. K., T. A. Bargiello, F. R. Jackson, M. W. Young. 1987. Changes in the abundance and structure of the per gene product can alter periodicity of the Drosophila clock. *Nature* 326:390–392

Burbach, K. M., A. Poland, C. A. Bradfield. 1992. Cloning of the Ah-receptor cDNA reveals a distinctive ligand-activated transcription factor. *Proc. Natl. Acad. Sci. USA* 89:8185–8189

Crosthwaite, S. K., J. J. Loros, D. J. C. 1995. Light-induced resetting of a circadian clock is mediated by a rapid increase in frequency transcript. *Cell* 81:1003–1012

Dunlap, J. C. 1993. Genetic analysis of circadian clocks. *Annu. Rev. Physiol.* 55:683–729

Edery, I., J. E. Rutila, M. Rosbash. 1994a. Phase shifting of the circadian clock by induction of the Drosophila period protein. *Science* 263:237–240

Edery, I., L. J. Zwiebel, M. E. Dembinska, M. Rosbash. 1994b. Temporal phosphorylation of the Drosophila period protein. *Proc. Natl. Acad. Sci. USA* 91:2260–2264

Favello, A., L. Hillier, R. K. Wilson. 1995. Genomic DNA sequencing methods. In *Methods in Cell Biology*, eds. HF Epstein, DC Shakes, pp.551–569. San Diego: Academic Press.

Feldman, J. F. 1982. Genetic approaches to circadian clocks. *Ann. Rev. Plant Physiol.* 33:583–608

Feldman, J. F., M. N. Hoyle. 1973. Isolation of circadian clock mutants of *Neurospora crassa*. *Genetics* 75:605–613

Fields, S., O.-K. Song. 1989. A novel genetic system to detect protein-protein interactions. *Nature* 340:245–246

Geissler, E. N., M. A. Ryan, D. E. Housman. 1988b. The dominant-white spotting (W) locus of the mouse encodes the c-kit proto-oncogene. *Cell* 55:185–192

Gekakis, N., L. Saez, A.-M. Delahaye-Brown, M. P. Myers, A. Sehgal, M. W. Young, C. J. Weitz. 1995. Isolation of timeless by PER protein interaction: Defective interaction between timeless protein and long-period mutant PER$^L$. *Science* 270:811–815

Hall, J. C. 1990. Genetics of circadian rhythms. *Annu. Rev. Genet.* 24:659–697

Hall, J. C., C. P. Kyriacou. 1990. Genetics of biological rhythms in Drosophila. *Adv. Insect Physiol.* 22:221–297

Hardin, P. E., J. C. Hall, M. Rosbash. 1990. Feedback of the Drosophila period gene product on circadian cycling of its messenger RNA levels. *Nature* 343:536–540

Hardin, P. E., J. C. Hall, M. Rosbash. 1992. Circadian oscillations in period gene mRNA levels are transcriptionally regulated. *Proc. Natl. Acad. Sci. USA* 89:11711–11715

Hoffman, E. C., H. Reyes, F.-F. Chu, F. Sader, L. H. Conley, B. A. Brooks, O. Hankinson. 1991. Cloning of a factor required for activity of the Ah (dioxin) receptor. *Science* 252:954–958

Hogan, B., R. Beddington, F. Constantini, E. Lacey. 1994. *Manipulating the Mouse Embryo, A Laboratory Manual*. Plainview, N.Y.: Cold Spring Harbor Laboratory Press. pp.

Huang, Z. J., I. Edery, M. Rosbash. 1993. PAS is a dimerization domain common to Drosophila Period and several transcription factors. *Nature* 364:259–262

Hunter-Ensor, M., A. Ousley, A. Sehgal. 1996. Regulation of the Drosophila protein timeless suggests a mechanism for resetting the circadian clock by light. *Cell* 84:677–685

Konopka, R. J., S. Benzer. 1971. Clock mutants of *Drosophila melanogaster*. *Proc. Natl. Acad. Sci. USA* 68:2112–2116

Krumlauf, R. 1993. Hox genes and pattern formation in the branchial region of the vertebrate head. *Trends Genet.* 9:106–112

Kusumi, K., J. S. Smith, J. A. Segre, D. S. Koos, E. S. Lander. 1993. Construction of a large-insert yeast artificial chromosome library of the mouse genome. *Mammalian Genome* 4:391–392

Lee, C., V. Parikh, T. Itsukaichi, K. Bae, I. Edery. 1996. Resetting the Drosophila clock by photic regulation of PER and a PER-TIM complex. *Science* 271:1740–1744

Lisitsyn, N., N. Lisitsyn, M. Wigler. 1993. Cloning the differences between two complex genomes. *Science* 259:946–951

Liu, X., L. J. Zwiebel, D. Hinton, S. Benzer, J. C. Hall, M. Rosbash. 1992. The period gene encodes a predominantly nuclear protein in adult Drosophila. *J Neurosci.* 12:2735–2744

Lovett, M. 1994. Fishing for complements: finding genes by direct selection. *Trends in Genetics* 10:352–357

Lynch, G. R., C. B. Lynch. 1992. Using quantitative genetic methods to understand mammalian circadian behavior and photoperiodism. In *Techniques for the Genetic Analysis of brain and Behavior*, eds. D Goldowitz, D Wahlsten, R E Wimer, pp. 251–268. New York: Elsevier.

Lyon, M. F., P. H. Glenister, J. F. Loutit, E. P. Evans, J. Peters. 1984. A presumed deletion covering the W and Ph loci of the mouse. *Genetical Research* 44:161–168

Marchuk, D. A., F. S. Collins. 1994. The use if YACs to identify expressed sequences: cDNA screening using total YAC insert. In *YAC Libraries: A User's Guide*, eds. D L Nelson, B H Brownstein, pp. 113–126. New York: W. H. Freeman and Co.

Matsui, M., Y. Mitsui, N. Ishida. 1993. Circadian regulation of per repeat mRNA in the suprachiasmatic nucleus of rat brain. *Neurosci. Lett.* 163:189–192

McClung, C. R., B. A. Fox, J. C. Dunlap. 1989. The Neurospora clock gene frequency shares a sequence element with the Drosophila clock gene period. *Nature* 339:558–562

Muller, H. J. 1932. *Further studies on the nature and causes of gene mutations*. Sixth International Congress of Genetics, Ithaca, N.Y., Brooklyn Botanic Gardens.

Myers, M. P., K. Wager-Smith, A. Rothenfluh-Hilfiker, M. W. Young. 1996. Light-induced degradation of TIMELESS and entrainment of the Drosophila circadian clock. *Science* 271:17361740

Myers, M. P., K. Wager-Smith, C. S. Wesley, M. W. Young. 1995. Positional cloning and sequence analysis of the Drosophila clock gene, timeless. *Science* 270:805–808

Nambu, J. R., J. Lewis, K. A. Wharton Jr., S. T. Crews. 1991. The Drosophila single-minded gene encodes a helix-loop-helix protein that acts as a master regulator of CNS midline development. *Cell* 67:1157–1167

Park, E.-C., H. R. Horvitz. 1986. Mutations with dominant effects on the behavior and morphology of the nematode *Caenorhabditis elegans*. *Genetics* 113:821–852

Pittendrigh, C. S., S. Daan. 1976. A functional analysis of circadian pacemakers in nocturnal rodents: I. The stability and lability of spontaneous frequency. *J Comp. Physiol.* 106:223–252

Ralph, M. R. 1991. Suprachiasmatic nucleus transplant studies using the tau mutation in golden hamsters. In *Suprachiasmatic Nucleus: The Mind's Clock*, eds. D C Klein, R Y Moore, S M Reppert, pp. 341–348. New York: Oxford University Press.

Ralph, M. R., R. G. Foster, F. C. Davis, M. Menaker. 1990. Transplanted suprachiasmatic nucleus determines circadian period. *Science* 247:975–978

Ralph, M. R., M. N. Lehman. 1991. Transplantation: a new tool in the analysis of the mammalian hypothalamic circadian pacemaker. *Trends Neurosci.* 14:362–366

Ralph, M. R., M. Menaker. 1988. A mutation of the circadian system in golden hamsters. *Science* 241:1225–1227

Reppert, S. M., T. Tsai, A. L. Roca, I. Sauman. 1994. Cloning of a structural and functional homolog of the circadian clock gene period from the giant silkmoth *Antheraea pernyi*. *Neuron* 13:1167–1176

Rosbash, M., J. C. Hall. 1989. The molecular biology of circadian rhythms. *Neuron* 3:387–398

Schwart, W. J., P. Zimmerman. 1990. Circadian timekeeping in BALB/c and C57BL/6 inbred mouse strains. *J. Neurosci.* 10:3685–3694

Sehgal, A., J. L. Price, B. Man, M. W. Young. 1994. Loss of circadian behavioral rhythms and per RNA oscillations in the Drosophila mutant timeless. *Science* 263:1603–1606

Shin, H.-S., T. A. Bargiello, B. T. Clark, F. R. Jackson, M. W. Young. 1985. An unusual coding sequence from a Drosophila clock gene is conserved in vertebrates. *Nature* 317:445–448

Shizuya, H., B. Birren, U. J. Kim, V. Mancino, T. Slepak, Y. Tachiiri, M. Simon. 1992. Cloning and stable maintenance of 300-kilobase-pair fragments of human DNA in *Escherichia coli* using an F-factor-based vector. *Proc. Natl. Acad. Sci. USA* 89:8794–8797

Siwicki, K. K., C. Eastman, G. Petersen, M. Rosbash, J. C. Hall. 1988. Antibodies to the period gene product of Drosophila reveal diverse tissue distribution and rhythmic changes in the visual system. *Neuron* 1:141–150

Siwicki, K. K., W. J. Schwartz, J. C. Hall. 1992. An antibody to the Drosophila period protein labels antigens in the suprachiasmatic nucleus of the rat. *J. Neurogenetics* 8:33–42

Smith, R. F., R. J. Konopka. 1982. Effects of dosage alterations at the per locus on the period of the circadian clock of Drosophila. *Mol. Gen. Genet.* 185:30–36

Takahashi, J. S. 1995. Molecular neurobiology and genetics of circadian rhythms in mammals. *Annu. Rev. Neurosci.* 18:531–553

Takahashi, J. S., L. H. Pinto, M. H. Vitaterna. 1994. Forward and reverse genetic approaches to behavior in the mouse. *Science* 264:1724–1733

Vignau, J., M. Dahlitz, J. Arendt, J. English, J. D. Parkes. 1993. Biological rhythms and sleep disorders in man: The delayed sleep phase syndrome. In *Light and Biological Rhythms in Man*, ed. L Wetterberg, pp.261–271. Oxford: Pergamon Press.

Vitaterna, M. H., D. P. King, A.-M. Chang, J. M. Kornhauser, P. L. Lowrey, J. D. McDonald, W. F. Dove, L. P. Pinto, F. W. Turek, J. S. Takahashi. 1994. Mutagenesis and mapping of a mouse gene, Clock, essential for circadian behavior. *Science* 264:719–725

Vitaterna, M. H., D. P. King, A.-M. Chang, J. M. Komhauser, P. L. Lowrey, J. D. McDonald, W. F. Dove, L. P. Pinto, F. W. Turek, J. S. Takahashi. 1994. Mutagenesis and mapping of a mouse gene, Clock, essential for circadian behavior. *Science* 264:719–725

Vogelbaum, M. A., M. Menaker. 1992. Temporal chimeras produced by hypothalamic transplants. *J. Neurosci.* 12:3619–3627

Vosshall, L. B., J. L. Price, A. Sehgal, L. Saez, M. W. Young. 1994. Block in nuclear localization of period protein by a second clock mutation, timeless. *Science* 263:1606–1609

Wehr, T. A., N. E. Rosenthal. 1989. Seasonality and affective illness. *Am. J. Psychiatry* 146:829–839

Yu, Q., A. C. Jacquier, Y. Citri, M. Hamblen, J. C. Hall, M. Rosbash. 1987. Molecular mapping of point mutations in the period gene that stop or speed up biological clocks in *Drosophila melanogaster*. *Proc. Natl. Acad. Sci. USA* 84:784–788

Zeng, H., Z. Qian, M. P. Myers, M. Rosbash. 1996. A light-entrainment mechanism for the Drosophila circadian clock. *Nature* 380:129–135

Zerr, D. M., J. C. Hall, M. Rosbash, K. K. Siwicki. 1990. Circadian fluctuations of period protein immunoreactivity in the CNS and the visual system of Drosophila. *J. Neurosci.* 10:2749–2762

Zipursky, S. L., G. M. Rubin. 1994. Determination of neuronal cell fate: Lessons from the R7 neuron of Drosophila. *Annu. Rev. Neurosci.* 17:373–397

1988. *Reproduction, Nutrition and developpement*. Paris, Institut National de la Recherche Agronomique, pp Albertsson-Wikland, K. and S. Rosberg. 1988. Analyses of 24-hour growth hormone profiles in children: Relation to growth. *J Clin Endocrinol Metab* 67:

Aldrich, M. S. 1994. Parkinsonism. In: *Principles and Practice of Sleep Medicine*. M H Kryger, T Roth and W C Dement Eds., Philadelphia, W. B. Saunders Co., 783–789.

Arendt, J. 1995. *Melatonin and the Mammalian Pineal Gland*. London, Chapman & Hall, pp 331.

Aschoff, J. 1992. Day-night variations in the cardiovascular system. Historical and other notes by an outsider. In: *Temporal Variations of the Cardiovascular System*.

Schmidt/Engel/Blümchen Eds., Berlin Heidelberg, Springer-Verlag, 3–14.

Benca, R. M. 1994. Mood disorders. In: *Principles and Practice of Sleep Medicine*. M H Kryger, T Roth and W C Dement Eds., Philadelphia, W. B. Saunders Co., 899–913.

Benca, R. M. and R. C. Casper. 1994. Sleep in eating disorders. In: *Principles and Practice of Sleep Medicine*. M H Kryger, T Roth and W C Dement Eds., Philadelphia, W. B. Saunders Co., 927–933.

Bliwise, D. L. 1994. Dementia. In: *Principles and Practice of Sleep Medicine*. M H Kryger, T Roth and W C Dement Eds., Philadelphia, W. B. Saunders Co., 790–800.

Borbély, A. A. 1994. Sleep homeostasis and models of sleep regulatoin. In: *Principles and Practice of Sleep Medicine*. M H Kryger, T Roth and W C Dement Eds., Philadelphia, W. B. Saunders Co., 309–320.

Calvo, J. R., M. Rafii-El-Idrissi, D. Pozo and J. M. Guerrero. 1995. Immunomodulatory role of melatonin: Specific binding sites in human and rodent lymphoid cells. *J Pineal Res* 18:119–126.

Card, J. P. and R. Y. Moore. 1991. The organization of visual circuits influencing the circadian activity of suprachiasmatic nucleus. In: *Suprachiasmatic Nucleus: The Mind's Clock*. D C Klein, R Y Moore and S M Reppert Eds., New York, Oxford University Press, 51–76.

Cohen, M. C. and J. E. Muller. 1992. Onset of acute myocardial infarction—circadian variation and triggers. *Cardiovascular Res*. 26:831–838.

Colantonio, D., P. Pasqualetti, R. Casale, P. Desiati, G. Giandomenico and G. Natali. 1989. Atrial natriuretic peptide-renin-aldosterone system in cirrhosis of the liver: Circadian study. *Life Sciences* 45:631–635.

Constantinescu, C. S. 1995. Melanin, Melatonin, melanocyte-stimulating hormone, and the susceptibility to autoimmune demyelination: A rationale for light therapy in multiple sclerosis. *Med Hypotheses* 45:455–458.

de Graaf, C., P. Jas, K. van der Kooy and R. Leenen. 1993. Circadian rhythms of appetite at different stages of a weight loss programme. *Intl J Obesity* 17:521–526.

Decker, K., U. Disque-Kaiser, M. Schreckenberger and S. Reuss. 1995. Demonstration of retinal afferents in the RCS rat, with reference to the retinohypothalamic projection and suprachiasmatic nucleus. *Cell Tissue Res* 282:473–480.

Douglas, N. J. 1994. Control of ventilation during sleep. In: *Principles and Practice of Sleep Medicine*. M H Kryger, T Roth and W C Dement Eds., Philadelphia, W. B. Saunders Co., 204–211.

Edmunds Jr, L. N. 1988. *Cellular and Molecular Bases of Biological Clocks*. New York, Springer-Verlag, pp 497.

García-Pagán, J. C., F. Feu, A. Castells, A. Luca, H. R. C., F. Rivera, J. Bosch and J. Rodés. 1994. Circadian variations of portal pressure and variceal hemorrhage in patients with cirrhosis. *Hepatology* 19:595–601.

George, C. F. P. 1994. Cardiovascular disease and sleep. In: *Principles and Practice of Sleep Medicine*. M H Kryger, T Roth and W C Dement Eds., Philadelphia, W. B. Saunders Co., 835–846.

Gillis, A. M. and W. W. Flemons. 1994. Cardiac arrhythmias during sleep. In: *Principles and Practice of Sleep Medicine*. M H Kryger, T Roth and W C Dement Eds., Philadelphia, W. B. Saunders Co., 847–860.

Graeber, R. C. 1994. Jet lag and sleep disruption. In: *Principles and Practice of Sleep Medicine*. M H Kryger, T Roth and W C Dement Eds., Philadelphia, W. B. Saunders Co., 463–470.

Hallonquist, J. D., M. A. Goldberg and J. S. Brandes. 1986. Affective disorders and circadian rhythms. *Can. J Psychiatry* 31:259–271.

Hartmann, E. 1994. Bruxism. In: Principles and Practice of Sleep Medicine. M H Kryger, T Roth and W C Dement Eds., Philadelphia, W. B. Saunders Co., 598–601.

Hineno, T., M. Mizobuchi, K. Hiratani, Y. Inami and Y. Kakimoto. 1992. Disappearance of circadian rhythms in Parkinson's disease model induced by 1-methyl-4-phenyl-1,2,3,6-tetrahydropyridine in dogs. *Brain Res*. 580:92–99.

Hokken-Koelega, A. C. S., W. H. L. Hackeng, T. Stijnen, J. M. Wit, S.M.P.F. de Muinck Keizer-Schrama and S. L. S. Drop. 1990. Twenty-four-hour plasma growth hormone (GH) profiles, urinary GH excretion, and plasma insulin-like growth factor-I and -II levels in prepubertal children with chronic renal insufficiency and severe growth retardation. *J Clin Endocrinol Metab* 71:688–695.

Hyde, T. M., M. F. Egan, R. J. Brown, D. R. Weinberger and J. E. Kleinman. 1995. Diurnal variation in tardive dyskinesia. *Psychiatry Research* 56:53–57.

Jacobshagen, S. and C. H. Johnson. 199 4. Circadian rhythms of gene expression in chlamydomonas reinhardtii: circadian cycling of mRNA abundances of cab II, and possibly of B-tubulin and cytochrome c. *European J Cell Biol*. 64:142–152.

Krueger, J. M. and M. L. Kanovsky. 1995. Sleep as a neuroimmune phenomenon: A brief historical perspective. *Adv Neuroimmunol*. 5:5–12.

Kryger, M. H., T. Roth and M. Carskadon. 1994. Circadian Rhythms in Humans: An overview. In: *Principles and Practice of Sleep Medicine*. M H Kryger, T Roth and W C Dement Eds., Philadelphia, W. B. Saunders Co., 301–308.

Kryger, M. H., T. Roth and W. C. Dement. 1994. *Principles and Practice of Sleep Medicine*. Philadelphia, W. B. Saunders Co., pp 1067.

Larsen, K. R., M. T. Dayton and J. G. Moore. 1991. Circadian rhythm in gastric mucosal blood flow in fasting rat stomach. *J surgical Res* 51:275–280.

Larsen, K. R., J. G. Moore, M. T. Dayton and Z. Yu. 1993. Circadian rhythm in aspirin (ASA)-induced injury to the stomach of the fasted rat. *Digestive Diseases and Sciences* 38:1435–1440.

Lausson, S., N. Segond, G. Milhaud and J. F. Staub. 1989. Circadian rhythms of calcitonin gene expression in the rat. *J Endocrinol* 122:527–534.

LaVail, M. M. 1976. Rod outer segment disk shedding in rat retina: Relationship to cyclic lighting. *Science* 194:1071–1074.

Lemmer, B. 1989. Temporal aspects of the effects of cardiovascular active drugs in humans. In: *Chronopharmacology—Cellular and Biochemical Interactions*. B Lemmer Eds., New York, Marcel Dekker, 525–541.

Loros, J. J., S. A. Denome and J. C. Dunlap. 1989. Molecular cloning of genes under control of the circadian clock in Neurospora. *Science* 243:385–388.

Lugaresi, E. and P. Montagna. 1994. Fatal familial insomnia: A new prion disease. In: *Principles and Practice of Sleep Medicine*. M H Kryger, T Roth and W C Dement Eds., Philadelphia, W. B. Saunders Co., 547–548.

Mann, N. P., R. Haddow, L. Stokes, S. Goodley and N. Rutter. 1986. Effect of night and day on preterm infants in a newborn nursery: Randomised trial. *British Med J* 293: 1265–1267.

Maron, B. J., J. Kogan, M. A. Proschan, G. M. Hecht and W. C. Roberts. 1994. Circadian variability in the occurrence of sudden cardiac death in ps with hypertrophic cardiomyopathy. *JACC* 23:1405–1409.

Meijer, J. H. 1991. Integration of visual information by the suprachiasmatic nucleus. In: *Suprachiasmatic Nucleus: The Mind's Clock*. D C Klein, R Y Moore and S M Reppert Eds., New York, Oxford University Press, 107–119.

Millar, A. J. and S. A. Kay. 199 1. Circadian control of cab gene transcription and mRNA accumulation of arabidopsis. *The Plant Cell* 3:541–550.

Mirmiran, M., J. H. Kok and J. G. Koppe. 1990. Emergence of circadian rhythms in early human development. In: *Sleep*. J Horne Eds., Bochum, Pontenagel Press, 26–28.

Monk, T. H. 1990. Shiftworker performance. *Occupational Medicine* 5:183–198.

Monk, T. H. 1994. Shift work. In: *Principles and Practice of Sleep Medicine*. M H Kryger, T Roth and W C Dement Eds., Philadelphia, W. B. Saunders Co., 471–476.

Monk, T. H., J. E. Fookson, M. Moline, L. and C. P. Pollak. 1985. Diurnal variation in mood and performance in a time-isolated environment *Chronobiol. Int.* 2:185–193.

Monk, T. H., E. D. Weitzman, J. E. Fookson and M. L. Moline. 1984. Circadian rhythms in human performance efficiency under free-running conditions. *Chronobiologia* 11:343–354.

Ohta, T. and S. Endo. 1985. Chronobiological comparison of sleep-wake rhythm between chronic schizophrenia and normal control. *Folia Psychiat Neurol Jpn* 39:489–498.

Orem, J. 1994. Respiratory neurons and sleep. In: *Principles and Practice of Sleep Medicine*. M H Kryger, T Roth and W C Dement Eds., Philadelphia, W. B. Saunders Co., 177–193.

Orr, W. C. 1994. Gastrointestinal physiology. In: *Principles and Practice of Sleep Medicine*. M H Kryger, T Roth and W C Dement Eds., Philadelphia, W. B. Saunders Co., 252–259.

Penev, P. D., P. C. Zee and F. W. Turek. 1997. Serotonin in the spotlight. *Nature* 385:123.

Poirel, C. 1991. Circadian chronobiology of epilepsy: Murine models of seizure susceptibility and theoretical perspectives for neurology. *Chronobiologia* 18:49–69.

Reiter, R. J. and B. K. Follett. 1980. *Progress in Reproductive Biology: Seasonal Reproduction in Higher Vertebrates*. Switzerland, S. Karger, pp Richter, C. P. 1979. *Biological Clocks in Medicine and Psychiatry*. Springfield, Ill., Charles C. Thomas Publisher, pp 111.

Roehrs, T. and T. Roth. 1994. Chronic insomnias associated with circadian rhythm disorders. In: *Principles and Practice of Sleep Medicine*. M H Kryger, T Roth and W C Dement Eds., Philadelphia, W. B. Saunders Co., 477–481.

Roth, T., T. A. Roehrs, M. A. Carskadon and W. C. Dement. 1994. Daytime sleepiness and alertness. In: *Principles and Practice of Sleep Medicine*. M H Kryger, T Roth and W C Dement Eds., Philadelphia, W. B. Saunders Co., 40–49.

Rusak, B. and I. Zucker. 1975. Biological rhythms and animal behavior. *Ann. Rev. Psychol.* 26:137–171.

Sack, R. L., A. J. Lewy, M. L. Blood, L. D. Keith and H. Nakagawa 1992. Circadian rhythm abnormalities in totally blind people: Incidence and clinical significance. *J Clin Endocrinol Metab* 75:127–134.

Sano, H., H. Hayashi, M. Makino, H. Tadezawa, M. Hirai, H. Saito and S. Ebihara. 1995. Effects of suprachiasmatic lesions on circadian rhythms of blood pressure, heart rate and locomotor activity in the rat. *Jpn Circ J* 59:565–573.

Sapolsky, R. M. 1992. *Stress, The Aging Brain, and the Mechanisms of Neuron Death*. Cambridge, Mass., The MIT Press, pp Smith, L., S. Folkard and C. J. M. Poole. 1994. Increased injuries on night shift. *Lancet* 344:1137–1139.

Spallone, V., L. Bernardi, L. Ricordi, P. Solda, M. R. Maiello, A. Calciati, S. Gambardella, P. Fratino and G. Menzinger. 1993. Relationship between the circadian rhythms of blood pressure and sympathovagal balance in diabetic autonomic neuropathy. *Diabetes* 42:1745–1752.

Taylor, W. C. 1989. Transcriptional regulation by a circadian rhythm. *The Plant Cell* 1:259–264.

Terman, M. 1994. Light treatment. In: *Principles and Practice of Sleep Medicine*. M H Kryger, T Roth and W C Dement Eds., Philadelphia, W. B. Saunders Co., 1012–1029.

Tornatzky, W. and K. A. Miczek. 1993. Long-term impairment of autonomic circadian rhythms after brief intermittent social stress. *Physiol. Behav.* 53:983–993.

Turek, F. W. 1994. Circadian rhythms. In: *Recent Progress in Hormone Research*. W Bardin Eds., New York, Academic Press, 43–90.

Turek, F. W., P. Penev, Y. Zhang, O. Van Reeth, J. S. Takahashi and P. Zee. 1995. Alterations in circadian system in advanced age. In: *Ciba Foundation Symposium No 183: Circadian Clocks and Their Adjustment*. J Waterhouse Eds., London, Pitman Press, 212–234.

Turek, F. W. and E. Van Cauter. 1994. Rhythms in Reproduction. In: *Physiology of Reproduction*. E Knobil and J Neill Eds., New York, Raven Press, 487–540.

Turek, F. W. and O. Van Reeth. 1996. Circadian Rhythms. In: *Handbook of Physiology*: Chapter 4 - Environmental Physiology. M J Fregly and C M Blatteis Eds., Oxford, Oxford University Press, 1329–1360.

US Congress, O.o.T.A. September, 1991. *Biological Rhythms: Implicationsfor the Worker*. Washington, US Government Printing Office, pp Van Cauter, E. and F. W. Turek. 1986. Depression: a disorder of timekeeping? *Perspect. Biol. Med.* 29:510–519.

Van Cauter, E. and F. W. Turek. 1995. Endocrine and other biological rhythms. In: *Endocrinology*. L J DeGroot Eds., Philadelphia, W. B. Saunders, 2487–2548.

Van Reeth, O., J. Sturis, M. M. Bryne, J. D. Blackman, M. L'Hermite-Balériaux, R. Leproult, C. Oliner, S. Refetoff, F. W. Turek and E. Van Cauter. 1994. Nocturnal exercise phase-delays the circadian rhythms of melatonin and thyrotropin secretion in normal men. *Am. J. Physiol.* 266:E964–E974.

Walker, C. A., C. M. Winget and K. F. A. Soliman. 1981. *Chronopharmacology and Chronotherapeutics*. Tallahassee, Fla., Florida A&M University Foundation, pp 417.

Wehr, T. A. and F. K. Goodwin. 1983. *Circadian rhythms in psychiatry*. Pacific Grove, Calif., Boxwood, pp Wehr, T. A., D. Sack, N. Rosenthal, W. Duncan and J. C. Gillin. 1983. Circadian rhythm disturbances in manic-depressive illness. *Federation Proc.* 42:2809–2814.

Wehr, T. A., A. Wirz-Justice and F. K. Goodwin. 1979. Phase advance of the circadian sleep-wake cycle as an antidepressant. *Science* 206:710–713.

Weltzin, T. E., L. K. G. Hsu, C. Pollice and W. H. Kaye. 1991. Feeding patterns in bulimia nervosa. *Biol. Psychiatry* 30:1093–1110.

Wetterberg, L. 1994. Light and biological rhythms. *J Internal Medicine* 235:5–19.

Young, R. W. 1980. The chemistry of the retina: function, renewal, rhythms, and the nucelus. *Neurochemistry* 1:123–142.

What is claimed:

1. An isolated and purified polynucleotide comprising a sequence selected from the group of nucleic acid sequences consisting of:
   (a) from nucleotide position 1 to nucleotide position 2953 of SEQ ID NO:1;
   (b) from nucleotide position 389 to nucleotide position 2953 of SEQ ID NO:1;
   (c) from nucleotide position 392 to nucleotide position 2953 of SEQ ID NO:1;
   (d) from nucleotide position 419 to nucleotide position 2953 of SEQ ID NO:1;
   (e) from nucleotide position 491 to nucleotide position 2953 of SEQ ID NO:1;
   (f) SEQ ID NO:1;
   (g) sequences complementary to (a), (b), (c), (d), (e), or (f);
   (h) extrachromosomal sequences which on expression produce a polypeptide comprising the amino acid sequence residue of SEQ ID NO:2 from residue number 35 to residue number 855.

2. The polynucleotide of claim 1 that is a DNA molecule.

3. The polynucleotide of claim 1 that is a RNA molecule.

4. The polynucleotide of claim 1 having the sequence of SEQ ID NO:1 from nucleotide position 1 to nucleotide position 2953.

5. The polynucleotide of claim 1 having the sequence of SEQ ID NO:1 from nucleotide position 389 to nucleotide position 2953.

6. The polynucleotide of claim 1 having the sequence of SEQ ID NO:1 from nucleotide position 392 to nucleotide position 2953.

7. The polynucleotide of claim 1 having the sequence of SEQ ID NO:1 from nucleotide position 419 to nucleotide position 2953.

8. The polynucleotide of claim 1 having the sequence of SEQ ID NO:1 from nucleotide position 491 to nucleotide position 2953.

9. The polynucleotide of claim 1 having the sequence of SEQ ID NO:1.

10. A host cell transformed with the polynucleotide of claim 1.

11. An expression vector comprising the polynucleotide of claim 1.

12. The expression vector of claim 9 further comprising a promoter-enhancer.

13. A host cell transformed with the expression vector of claim 9.

14. A process of preparing a polypeptide that regulates the circadian rhythm of a mammal comprising transforming a suitable host cell with the expression vector of claim 9 and maintaining the cell under circumstances and for a period of time sufficient for polypeptide formation.

15. The process of claim 14 wherein the polypeptide comprises the amino acid residue sequence of SEQ ID NO:2 from residue number 35 to residue number 855.

16. The process of claim 14 wherein the polypeptide comprises the amino acid residue sequence of SEQ ID NO:2 from residue number 11 to residue number 855.

17. The process of claim 14 wherein the polypeptide comprises the amino acid residue sequence of SEQ ID NO:2 from residue number 10 to residue number 855.

18. The process of claim 14 wherein the polypeptide comprises the amino acid residue sequence of SEQ ID NO:2 from residue number 2 to residue number 855.

19. The process of claim 14 wherein the polypeptide has the amino acid residue sequence of SEQ ID NO:2.

20. An isolated and purified polynucleotide comprising a sequence selected from the group consisting of:
   a) a contiguous polynucleotide encoding amino acid residues from 1 to 513 and from 565 to 855 of SEQ ID NO:2;
   b) a contiguous polynucleotide encoding amino acid residues from 1 to 483 and from 514 to 855 of SEQ ID NO:2; and
   c) a contiguous polynucleotide encoding amino acid residues from 1 to 483 and from 565 to 855 of SEQ ID NO:2.

21. The polynucleotide of claim 20, wherein said polynucleotide comprises a sequence selected from the group consisting of:

a) a contiguous polynucleotide consisting of from nucleotide positions 389 to 1927 and from 2081 to 2953 of SEQ ID NO:1;
b) a contiguous polynucleotide consisting of from nucleotide positions 389 to 1837 and from 1928 to 2953 of SEQ ID NO:1; and
c) a contiguous polynucleotide consisting of from nucleotide positions 389 to 1837 and from 2081 to 2953 of SEQ ID NO:1.

22. An expression vector comprising the polynucleotide of claim 21.

23. A host cell transformed with the expression vector of claim 22.

24. A process of making a polypeptide that affects the circadian rhythm of a mammal comprising transforming a suitable host cell with the expression vector of claim 22, growing the host cell under conditions wherein the polypeptide is expressed, and isolating the polypeptide therefrom.

25. An expression vector comprising the polynucleotide of claim 20.

26. A host cell transformed with the expression vector of claim 25.

27. A process of making a polypeptide that affects the circadian rhythm of a mammal comprising transforming a suitable host cell with the expression vector of claim 25, growing the host cell under conditions wherein the polypeptide is expressed, and isolating the polypeptide therefrom.

28. An isolated and purified oligonucleotide of at least 15 nucleotides, that is identical or complementary to a contiguous stretch of at least 15 nucleotides of SEQ ID NO:1.

29. The oligonucleotide of claim 28 wherein the contiguous stretch of at least 15 nucleotides of SEQ ID NO:1 is located between about nucleotide position 1 and about nucleotide position 2953 of SEQ ID NO:1.

30. The oligonucleotide of claim 28 having from about 20 to about 35 nucleotides.

31. The oligonucleotide of claim 28 that is an antisense molecule.

32. The oligonucleotide of claim 28 that is a DNA molecule.

33. The oligonucleotide of claim 28 that is an RNA molecule. number 855.

34. A pharmaceutical composition comprising the expression vector of claim 9 together with a physiologically acceptable diluent.

35. A pharmaceutical composition comprising the polynucleotide of claim 13 together with a physiologically acceptable diluent.

* * * * *

SEQUENCE LISTING ( 1 ) GENERAL INFORMATION:

( i i i ) NUMBER OF SEQUENCES: 53

( 2 ) INFORMATION FOR SEQ ID NO:1:

( i ) SEQUENCE CHARACTERISTICS:
        ( A ) LENGTH: 7498 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 389..2954

( x i ) SEQUENCE DESCRIPTION: SEQ ID NO:1:

```
GGGGAGGAGC  GCGGCGGTAG  CGGTGAATTT  TGAGGGGTGG  GTCGGGGGCG  CGCACTCGCC        60

GCCCCTGGTG  CTGCCGGCTC  CCGGAGCCGT  GGCGTGTCCC  TGCTGTCGCC  GCTCGGCTGT       120

CGCGAGCCGC  CGCGGGCAGA  GTCCCGGGCG  GGGGAGGGAG  GAAGCCGGAG  CCTCAGGCAC       180

GTGAAAGAAA  AGCACAAGAA  GAAACTTTTA  CAGGCGTTGT  TGATTGGACT  AGGGCAACGA       240

TTCCCAAAAT  CACCAGCAAG  AGTTCTGATG  GTCAGTCACA  CAGAAGACGG  CCTTGCGTCT       300

GTGGGTGTTG  GAGACTCCAT  TCTAAAGATA  TAAAAAGTGA  AAGAGGAGAA  GTACAAATGT       360

CTACCACAAG  ACGAAAACAT  AATGTGTT ATG GTG TTT ACC GTA AGC TGT AGT            412
                                 Met Val Phe Thr Val Ser Cys Ser
                                  1               5

AAA ATG AGC TCA ATT GTT GAC AGA GAT GAC AGT AGT ATT TTT GAT GGA             460
Lys Met Ser Ser Ile Val Asp Arg Asp Asp Ser Ser Ile Phe Asp Gly
     10              15                  20

TTG GTG GAA GAA GAT GAC AAG GAC AAA GCA AAA AGA GTA TCT AGA AAC             508
Leu Val Glu Glu Asp Asp Lys Asp Lys Ala Lys Arg Val Ser Arg Asn
 25              30                  35                      40

AAA TCA GAA AAG AAA CGT AGA GAT CAG TTC AAT GTC CTC ATT AAG GAG             556
Lys Ser Glu Lys Lys Arg Arg Asp Gln Phe Asn Val Leu Ile Lys Glu
                 45                  50                  55

CTG GGG TCT ATG CTT CCT GGT AAC GCG AGA AAG ATG GAC AAG TCT ACT             604
Leu Gly Ser Met Leu Pro Gly Asn Ala Arg Lys Met Asp Lys Ser Thr
             60                  65                  70

GTT CTA CAG AAG AGC ATT GAT TTT TTG CGC AAA CAT AAA GAG ACC ACT             652
Val Leu Gln Lys Ser Ile Asp Phe Leu Arg Lys His Lys Glu Thr Thr
         75                  80                  85

GCA CAG TCA GAT GCT AGT GAG ATT CGA CAG GAC TGG AAA CCC ACA TTC             700
Ala Gln Ser Asp Ala Ser Glu Ile Arg Gln Asp Trp Lys Pro Thr Phe
     90                  95                 100

CTT AGT AAT GAA GAG TTT ACA CAG TTA ATG TTA GAG GCT CTT GAT GGT             748
Leu Ser Asn Glu Glu Phe Thr Gln Leu Met Leu Glu Ala Leu Asp Gly
105                 110                 115                 120

TTT TTT TTA GCG ATC ATG ACA GAT GGA AGT ATA ATA TAT GTA TCT GAG             796
Phe Phe Leu Ala Ile Met Thr Asp Gly Ser Ile Ile Tyr Val Ser Glu
                125                 130                 135

AGT GTA ACT TCG TTA CTT GAA CAT TTA CCA TCT GAT CTT GTG GAT CAA             844
Ser Val Thr Ser Leu Leu Glu His Leu Pro Ser Asp Leu Val Asp Gln
            140                 145                 150

AGT ATA TTT AAT TTT ATC CCA GAG GGA GAA CAT TCA GAG GTT TAT AAG             892
Ser Ile Phe Asn Phe Ile Pro Glu Gly Glu His Ser Glu Val Tyr Lys
        155                 160                 165
```

```
ATA CTC TCT ACT CAT CTG CTG GAA AGT GAC TCA TTA ACC CCT GAG TAC    940
Ile Leu Ser Thr His Leu Leu Glu Ser Asp Ser Leu Thr Pro Glu Tyr
    170             175                 180

TTA AAA TCA AAA AAT CAG TTA GAA TTC TGT TGT CAC ATG CTT CGA GGA    988
Leu Lys Ser Lys Asn Gln Leu Glu Phe Cys Cys His Met Leu Arg Gly
185             190                 195                 200

ACA ATA GAC CCA AAG GAG CCA TCC ACC TAT GAA TAT GTG AGA TTT ATA   1036
Thr Ile Asp Pro Lys Glu Pro Ser Thr Tyr Glu Tyr Val Arg Phe Ile
                205                 210                 215

GGA AAT TTT AAA TCT TTA ACC AGT GTA TCA ACT TCA ACA CAC AAT GGT   1084
Gly Asn Phe Lys Ser Leu Thr Ser Val Ser Thr Ser Thr His Asn Gly
            220                 225                 230

TTT GAA GGA ACT ATA CAA CGC ACA CAT AGG CCT TCT TAT GAA GAT AGA   1132
Phe Glu Gly Thr Ile Gln Arg Thr His Arg Pro Ser Tyr Glu Asp Arg
        235                 240                 245

GTT TGT TTT GTA GCT ACT GTC AGA TTA GCT ACA CCT CAG TTC ATC AAG   1180
Val Cys Phe Val Ala Thr Val Arg Leu Ala Thr Pro Gln Phe Ile Lys
    250                 255                 260

GAA ATG TGT ACT GTT GAA GAA CCA AAT GAA GAG TTT ACA TCT AGA CAC   1228
Glu Met Cys Thr Val Glu Glu Pro Asn Glu Glu Phe Thr Ser Arg His
265             270                 275                 280

AGT TTA GAA TGG AAG TTT CTA TTT TTA GAT CAC AGG GCA CCA CCA ATA   1276
Ser Leu Glu Trp Lys Phe Leu Phe Leu Asp His Arg Ala Pro Pro Ile
                285                 290                 295

ATA GGC TAT TTG CCA TTT GAA GTC TTG GGA ACA TCA GGC TAT GAT TAC   1324
Ile Gly Tyr Leu Pro Phe Glu Val Leu Gly Thr Ser Gly Tyr Asp Tyr
            300                 305                 310

TAT CAT GTG GAT GAC CTA GAA AAT CTG GCA AAA TGT CAC GAG CAC TTA   1372
Tyr His Val Asp Asp Leu Glu Asn Leu Ala Lys Cys His Glu His Leu
        315                 320                 325

ATG CAA TAT GGA AAA GGC AAA TCG TGT TAC TAT AGA TTC CTG ACC AAA   1420
Met Gln Tyr Gly Lys Gly Lys Ser Cys Tyr Tyr Arg Phe Leu Thr Lys
    330                 335                 340

GGC CAG CAG TGG ATA TGG CTT CAG ACT CAT TAT TAT ATT ACT TAC CAT   1468
Gly Gln Gln Trp Ile Trp Leu Gln Thr His Tyr Tyr Ile Thr Tyr His
345             350                 355                 360

CAG TGG AAT TCA AGG CCA GAG TTC ATT GTT TGT ACT CAC ACT GTA GTA   1516
Gln Trp Asn Ser Arg Pro Glu Phe Ile Val Cys Thr His Thr Val Val
                365                 370                 375

AGT TAT GCA GAA GTT AGG GCT GAA AGA CGG CGA GAA CTT GGC ATT GAA   1564
Ser Tyr Ala Glu Val Arg Ala Glu Arg Arg Arg Glu Leu Gly Ile Glu
            380                 385                 390

GAG TCT CTT CCT GAG ACA GCT GCT GAC AAA AGC CAA GAT TCT GGG TCT   1612
Glu Ser Leu Pro Glu Thr Ala Ala Asp Lys Ser Gln Asp Ser Gly Ser
        395                 400                 405

GAC AAT CGT ATC AAC ACA GTG AGT CTC AAG GAA GCA CTG GAA AGG TTT   1660
Asp Asn Arg Ile Asn Thr Val Ser Leu Lys Glu Ala Leu Glu Arg Phe
    410                 415                 420

GAT CAC AGC CCA ACT CCT TCT GCC TCC TCT AGA AGC TCA CGA AAG TCA   1708
Asp His Ser Pro Thr Pro Ser Ala Ser Ser Arg Ser Ser Arg Lys Ser
425             430                 435                 440

TCT CAC ACC GCA GTC TCA GAC CCT TCC TCC ACA CCG ACA AAG ATC CCT   1756
Ser His Thr Ala Val Ser Asp Pro Ser Ser Thr Pro Thr Lys Ile Pro
                445                 450                 455

ACT GAT ACT AGC ACT CCT CCC AGA CAG CAT TTG CCA GCT CAT GAA AAG   1804
Thr Asp Thr Ser Thr Pro Pro Arg Gln His Leu Pro Ala His Glu Lys
            460                 465                 470

ATG ACA CAG CGG AGG TCG TCC TTC AGC AGT CAG TCC ATA AAC TCC CAG   1852
Met Thr Gln Arg Arg Ser Ser Phe Ser Ser Gln Ser Ile Asn Ser Gln
        475                 480                 485
```

| | | | | | | | | | | | | | | | | |
|---|---|---|---|---|---|---|---|---|---|---|---|---|---|---|---|---|
| TCA | GTT | GGT | CCA | TCA | TTA | ACA | CAG | CCA | GCG | ATG | TCT | CAA | GCT | GCA | AAT | 1900 |
| Ser | Val | Gly | Pro | Ser | Leu | Thr | Gln | Pro | Ala | Met | Ser | Gln | Ala | Ala | Asn | |
| | 490 | | | | 495 | | | | | 500 | | | | | | |
| TTA | CCA | ATT | CCA | CAA | GGC | ATG | TCA | CAG | TTT | CAG | TTT | TCA | GCT | CAG | TTA | 1948 |
| Leu | Pro | Ile | Pro | Gln | Gly | Met | Ser | Gln | Phe | Gln | Phe | Ser | Ala | Gln | Leu | |
| 505 | | | | | 510 | | | | | 515 | | | | | 520 | |
| GGA | GCC | ATG | CAG | CAT | CTA | AAA | GAC | CAG | CTA | GAG | CAG | CGG | ACA | CGG | ATG | 1996 |
| Gly | Ala | Met | Gln | His | Leu | Lys | Asp | Gln | Leu | Glu | Gln | Arg | Thr | Arg | Met | |
| | | | | 525 | | | | | 530 | | | | | 535 | | |
| ATA | GAG | GCA | AAT | ATT | CAT | CGG | CAG | CAA | GAA | GAA | CTA | AGG | AAA | ATT | CAA | 2044 |
| Ile | Glu | Ala | Asn | Ile | His | Arg | Gln | Gln | Glu | Glu | Leu | Arg | Lys | Ile | Gln | |
| | | | 540 | | | | | 545 | | | | | 550 | | | |
| GAG | CAA | CTT | CAG | ATG | GTC | CAT | GGT | CAA | GGG | CTA | CAG | ATG | TTT | TTG | CAG | 2092 |
| Glu | Gln | Leu | Gln | Met | Val | His | Gly | Gln | Gly | Leu | Gln | Met | Phe | Leu | Gln | |
| | | 555 | | | | | 560 | | | | | 565 | | | | |
| CAA | TCA | AAC | CCT | GGA | TTG | AAT | TTT | GGT | TCT | GTT | CAA | CTT | TCC | TCT | GGA | 2140 |
| Gln | Ser | Asn | Pro | Gly | Leu | Asn | Phe | Gly | Ser | Val | Gln | Leu | Ser | Ser | Gly | |
| | 570 | | | | | 575 | | | | | 580 | | | | | |
| AAT | TCT | AAT | ATC | CAG | CAG | CTC | ACA | CCT | GTA | AAT | ATG | CAA | GGC | CAG | GTT | 2188 |
| Asn | Ser | Asn | Ile | Gln | Gln | Leu | Thr | Pro | Val | Asn | Met | Gln | Gly | Gln | Val | |
| 585 | | | | | 590 | | | | | 595 | | | | | 600 | |
| GTC | CCT | GCT | AAC | CAG | GTT | CAG | AGT | GGA | CAT | ATC | AGC | ACA | GGC | CAG | CAC | 2236 |
| Val | Pro | Ala | Asn | Gln | Val | Gln | Ser | Gly | His | Ile | Ser | Thr | Gly | Gln | His | |
| | | | | 605 | | | | | 610 | | | | | 615 | | |
| ATG | ATA | CAG | CAA | CAG | ACT | TTA | CAA | AGT | ACA | TCA | ACT | CAG | CAG | AGT | CAA | 2284 |
| Met | Ile | Gln | Gln | Gln | Thr | Leu | Gln | Ser | Thr | Ser | Thr | Gln | Gln | Ser | Gln | |
| | | | 620 | | | | | 625 | | | | | 630 | | | |
| CAG | AGT | GTA | ATG | AGT | GGA | CAC | AGT | CAG | CAG | ACG | TCT | CTT | CCA | AGT | CAG | 2332 |
| Gln | Ser | Val | Met | Ser | Gly | His | Ser | Gln | Gln | Thr | Ser | Leu | Pro | Ser | Gln | |
| | | 635 | | | | | 640 | | | | | 645 | | | | |
| ACA | CCG | AGC | ACT | CTC | ACA | GCC | CCA | CTG | TAC | AAT | ACG | ATG | GTG | ATT | TCC | 2380 |
| Thr | Pro | Ser | Thr | Leu | Thr | Ala | Pro | Leu | Tyr | Asn | Thr | Met | Val | Ile | Ser | |
| | 650 | | | | | 655 | | | | | 660 | | | | | |
| CAG | CCT | GCA | GCT | GGG | AGC | ATG | GTC | CAG | ATT | CCA | TCC | AGT | ATG | CCA | CAG | 2428 |
| Gln | Pro | Ala | Ala | Gly | Ser | Met | Val | Gln | Ile | Pro | Ser | Ser | Met | Pro | Gln | |
| 665 | | | | | 670 | | | | | 675 | | | | | 680 | |
| AAC | AGT | ACC | CAG | AGT | GCT | ACA | GTC | ACT | ACG | TTC | ACT | CAG | GAC | AGA | CAG | 2476 |
| Asn | Ser | Thr | Gln | Ser | Ala | Thr | Val | Thr | Thr | Phe | Thr | Gln | Asp | Arg | Gln | |
| | | | | 685 | | | | | 690 | | | | | 695 | | |
| ATA | AGA | TTT | TCT | CAA | GGT | CAG | CAA | CTT | GTG | ACC | AAA | TTA | GTG | ACT | GCT | 2524 |
| Ile | Arg | Phe | Ser | Gln | Gly | Gln | Gln | Leu | Val | Thr | Lys | Leu | Val | Thr | Ala | |
| | | | 700 | | | | | 705 | | | | | 710 | | | |
| CCT | GTA | GCT | TGT | GGG | GCC | GTC | ATG | GTA | CCA | AGT | ACC | ATG | CTT | ATG | GGT | 2572 |
| Pro | Val | Ala | Cys | Gly | Ala | Val | Met | Val | Pro | Ser | Thr | Met | Leu | Met | Gly | |
| | | 715 | | | | | 720 | | | | | 725 | | | | |
| CAG | GTG | GTG | ACT | GCC | TAT | CCT | ACC | TTC | GCC | ACA | CAA | CAG | CAG | CAG | GCA | 2620 |
| Gln | Val | Val | Thr | Ala | Tyr | Pro | Thr | Phe | Ala | Thr | Gln | Gln | Gln | Gln | Ala | |
| | 730 | | | | | 735 | | | | | 740 | | | | | |
| CAG | ACA | TTA | TCG | GTA | ACA | CAA | CAG | CAG | CAG | CAG | CAG | CAG | CAG | CAG | CCA | 2668 |
| Gln | Thr | Leu | Ser | Val | Thr | Gln | Gln | Gln | Gln | Gln | Gln | Gln | Gln | Gln | Pro | |
| 745 | | | | | 750 | | | | | 755 | | | | | 760 | |
| CCA | CAG | CAA | CAG | CAA | CAA | CAA | CAG | CAG | AGT | TCC | CAG | GAA | CAG | CAG | CTT | 2716 |
| Pro | Gln | Gln | Gln | Gln | Gln | Gln | Gln | Gln | Ser | Ser | Gln | Glu | Gln | Gln | Leu | |
| | | | | 765 | | | | | 770 | | | | | 775 | | |
| CCT | TCA | GTT | CAG | CAG | CCA | GCT | CAG | GCC | CAG | CTG | GGC | CAG | CCA | CCA | CAG | 2764 |
| Pro | Ser | Val | Gln | Gln | Pro | Ala | Gln | Ala | Gln | Leu | Gly | Gln | Pro | Pro | Gln | |
| | | | 780 | | | | | 785 | | | | | 790 | | | |
| CAG | TTC | TTA | CAG | ACA | TCT | AGG | TTG | CTC | CAC | GGG | AAT | CCT | TCG | ACA | CAG | 2812 |
| Gln | Phe | Leu | Gln | Thr | Ser | Arg | Leu | Leu | His | Gly | Asn | Pro | Ser | Thr | Gln | |
| | | 795 | | | | | 800 | | | | | 805 | | | | |

| | | | | | | | | | | | | | | | | |
|---|---|---|---|---|---|---|---|---|---|---|---|---|---|---|---|---|
| CTC | ATC | CTC | TCT | GCT | GCC | TTT | CCA | CTA | CAA | CAG | AGC | ACT | TTC | CCT | CCT | 2860 |
| Leu | Ile | Leu | Ser | Ala | Ala | Phe | Pro | Leu | Gln | Gln | Ser | Thr | Phe | Pro | Pro | |
| | 810 | | | | 815 | | | | | | 820 | | | | | |
| TCG | CAC | CAC | CAG | CAA | CAC | CAG | CCT | CAG | CAG | CAA | CAG | CAG | CTT | CCT | CGG | 2908 |
| Ser | His | His | Gln | Gln | His | Gln | Pro | Gln | Gln | Gln | Gln | Gln | Leu | Pro | Arg | |
| 825 | | | | | 830 | | | | | 835 | | | | | 840 | |
| CAC | AGG | ACT | GAC | AGC | CTG | ACT | GAC | CCT | TCC | AAG | GTC | CAG | CCA | CAG | T | 2954 |
| His | Arg | Thr | Asp | Ser | Leu | Thr | Asp | Pro | Ser | Lys | Val | Gln | Pro | Gln | | |
| | | | | 845 | | | | | 850 | | | | | 855 | | |

```
AGCACACACA CTTCCTCTCT GACATGCGAG AGGAAGGGGA TGGCCAGAAA GAATCGCTCA  3014
GTTGGCATGC GGTCAGAAGT TGAACAGTTT CACGAGGGTG GTCTTGAGTG TTCAGTCCCT  3074
TGATGAGACG TAGGGAAGT  GCTGCCCAGT GCTTCAGATG TCCATTAAAT ACCAGCCAGT  3134
GGGAAATGGT CATAGGGACA CAGCCAATTC TGACAGTTTC TTTGCCCAGG TATTTTTTGA  3194
TAGAAAGAGT ATATTGCCAA ATGCTAACAA GCTCAGCTAT CAACCAGATC TTTACTGAAT  3254
CCGAAGAGCA CTAACAGTGT TGGTAGCTTT AGTGGGTCTG TGCCTGCATC AAATATTACA  3314
GAGGGCACAC CACTGCCAGG GGTTTGCTTA GAATGCCATG AAGATAGTCC AGTAGTTAAT  3374
AGTCCCCACC CCAAACTCCT CTCCCTGTTC AGACAATGAT GGAACCGTGA TGACTTTGAG  3434
AATGTTGTGC AGGTTTGAAT TCACTGTGTA CAGATGCTGT AGTGTCTCTG TGTCTGGATG  3494
GAGGAGAGAA AGCCACTTTG ATACAGAAAG CATTATCTGT CCCTCACAGG TATGAGTGCA  3554
TTTCATTAGG TTTGACACCA TGTACAAACT GATAACAACC TCTCTTTTTT CATTTTGTTT  3614
ACAACACAGT AGTGTTCTCG TTACTTTCC AGGGCACAAG TCTTTTGTC CGTGCTTTGG  3674
CTGTGATGTC ACAGTTTGTT CAGTGAGGTA ACAATGTGCT GCTGGGAATG GATTTTTTA   3734
AGGTTAAATT ATTGCTACAT TTCCACTTAC TCAGAAATAT CCCTTATTTC ATTATTTTC   3794
AATTATGTTT GAGAGAATTG CACTGCTTTA TTATTTAGA  TGGTTGGTTG AGAGTTTAAT  3854
CACATATTTT GATATATTTC ATAGTTGGAA TATTTATGTA AATGGTTTTC AACAAGCCTG  3914
AAAGTAATTT CAAGAATGTT TCAGTTGTAA GAGTAAAGTT TGCACACAAA ACATTTAGG   3974
CACTTTTTTA ACATTCTCAG AGGTGGGAAT TTTAACTTTT AGGATTGTT  GGAATCTTTT  4034
TATTATCTTT AAAAATTTCA ATGCTTCTTT TAGTCAGAAA TGATTCAGGG TTATTTGAGG  4094
GGAAAAAACC CATAGTGCCT TGATTTTAAT TCAGGTGATA ACTCACCATC TTGAATTCAT  4154
TGTCTGGTTT CAGTAGCAGT TTTGAAACCT TAGTACATTT TTAGCAGCAG TGTCATTCTC  4214
AAGTCCCCAT GAGGACTGCT GCGTCTCTTG GGCTGCCTGA CAGCGTCACA GCTGGGAATG  4274
GGATCCCAAA ATCGTTTCCT GTTTGCATCT TCCTCTAAAG CTAAGTAACT CTTTTAGGAA  4334
TTACCAGTAA ATACTTGCTC AGAGACAAGG GACAAGTTGT CTTTAATTTT CATTGCAGCA  4394
CTAGAATAAT GTAACTCACA TGCTTTTTAA ACATTAAGAT TTCATTTGGC AATATCATTC  4454
TCTACAGGTA ATAAACTCCA ACAAAGCTAC ATACATTTTA AAAGGCATTT TTTTAGATTT  4514
TATGGTACTA ATAATGAGTT TTTCAATTAA AGAACAAAAG ATCAGTAGGA TATAGAATAT  4574
CAAGTATTAC TGAGAAAAGG GAGGATAAGT GTGGCACATT AGAATTGACC TTAAAGGAA   4634
AGTATGTGAT GGTGAGGTGC TAAACTGGTT TCAGCAGTGC AGATAACCTA AGGCAGAGTT  4694
GCTAGATCAG GGCTTGGGGA ACTCGGAGTC AGCTATCTGT CTCTAGCTTT GCTCTCATCA  4754
TCAGTAAGTG TGTCTTTGTT TTCCTGTTTA CCTGACTGCA ATTAAGTTAG CAAGTTAGTG  4814
ATAAAAAGAA AACAACCAAA GAAAATTGGT ACCTACTCTT CTGCGTAAGA AGTGTGTCTA  4874
GATACCAGTC AGTAACTCAC ATATCACAGA AGTTCTTCTA GCTGACATTC ATACGAATAC  4934
CAGAAATAGT TGTGAGAATA CACATTTATG CAAGTTTGTG CACACGTGAC GAAATCAATG  4994
```

-continued

| | | | | | |
|---|---|---|---|---|---|
| TAAGTCGAGC | ACCCACATTG | CTTTTCTCCC | TTCCACATTG | CCTTCTTCTC | TTTGGCCATT | 5054 |
| CCATGTCCTC | GGAGTCGGAG | CTGTGCCTCG | TTTATCTTTT | TGCATCACAT | AGCGATAAGA | 5114 |
| ATTTAGCTAC | AGGAGATACA | ACATGCTAGT | TATGTAATGC | CTGCTGTTCT | TCACAGTTCA | 5174 |
| TCTCCCTGCT | TAAAAGTAGC | AGTTGATAAG | AAACTCTAGC | TGCTAAGGCT | GCTGTCCACA | 5234 |
| CGGAGATGCA | TGCTGGGCAA | CAGTTGTCAG | CACTAGCTGC | CTCTTAGCTC | CTTAATTCTT | 5294 |
| GGTTCCTTTG | GATGGCAAAC | TGTCTTTGTC | TGCTCCCCAC | ACGACTCCAG | TATTCTGAAG | 5354 |
| AAAGTTCATC | TTTTGCCTGT | TCATTCTGT | AGCCAAAGCT | GACTGAAACC | CCAAATCTAA | 5414 |
| ATCATGAAAA | GATACCAAAA | AGAAACACTT | CTCAGCTTCT | TAGAAACCTT | AACTTCTCTT | 5474 |
| GCTGTATTTC | ATGGATTTGA | TTTTCTTTGA | AATTTTTGAT | TCTGGGCAGC | GCCTTTTAAT | 5534 |
| TAAGAAATTG | TTAGGATGAA | GGTCAAACAG | GTTCTCATTG | CCCTGCAGGT | ACCTTGCTCT | 5594 |
| GGACTGCTTC | TGTATGGGGT | GACTTGGGGT | TGCTGAACAC | ACAGGATTAG | AACAGTAAAC | 5654 |
| ACAAAGCTGC | CCTTGAGGCT | GGCGTTAAAC | CAGAGCCTCA | ATATTGAAAA | TATCAAGTCC | 5714 |
| TCTTTCCTTC | CTTAGAGACG | AGACTGTGAG | AGGAAAGCAA | CTGTGGTAGG | TGGGCTTGCT | 5774 |
| TGCACATGAG | CACCAAGACC | ATTCCCCAAG | CTCTATCCTC | AGGGTAGCAT | TTAGAGTGCT | 5834 |
| GTGTTCTGCT | GTCACATAGA | CATGGCTTAG | GGATGTAGCA | CTAATAAAAG | AATGCCCGTG | 5894 |
| CTTTTGAATA | GTTGTGATAG | CAAACTCTAG | GCTAACTAGC | AAGTGTTTGA | ATTCTGTGTG | 5954 |
| CTGTATAGTA | GTTGGTCATT | GCCTTAAAGC | AGTCTCTTGG | AAGTTGGGAG | CACTGAAGCA | 6014 |
| GTCCAACCAT | ATATGGGCAT | CACGTTGAGG | GAGATGAGCC | TTGTTCAAGC | CTTAGAAAGG | 6074 |
| ACCCTTAGTC | TACACAGGTA | GATTCTTTTC | ACTTGGATAT | TACTGTGTTT | AAAATGTTTC | 6134 |
| CACTATGTTG | AGGCAGTTTT | TTAAAGTGGA | ACACAGATAG | GATTTTAGT | ATTTCTTTTT | 6194 |
| TTGTTTCTTT | GGTGATTAAA | GGTTTGTTGG | TAGACATTTG | TGTAAAAGTT | GTTCAAGCCT | 6254 |
| ATCATCTTTC | CAGTACTTGT | GGTCCTGTTC | TTAGTACCAG | AGTCCACAAT | GGAAAGTGTA | 6314 |
| AACACTGGAT | ATTAATATTG | CTGAGGGTGC | ATAGCCAGGT | GTGAGCTGAC | TGGAACTTCT | 6374 |
| CAGTGGTGAA | GAAACAGCAC | AACGGCACTT | GCCATTTCA | TAGTGATTGC | ATAAAGAGAC | 6434 |
| CTTCTAAGTT | TGTCTGGATT | GAGTGAACAC | TCTTCTAAGA | GGAGCTTCTC | AAGTAAATGC | 6494 |
| AAAGGAAAAG | AGTTGACTAT | TTTTATAGCA | TATTTAATAT | ATTTGTATAT | AACTATGAGT | 6554 |
| GTAGTAGGAA | CCCTCCACAT | GCCTCCCACT | TTTCTAATTC | CCTCCCCTTC | TGCCGTAGCC | 6614 |
| CTAGTCCAGC | CTCATCCGCA | TGGGTAATGT | GCCTACTGTC | AGCCTACCTA | CCAAAAGATA | 6674 |
| GTGCTGCTGC | TTTCTGAGAC | AGGTGAGATC | AGACTCTCAT | GCCTGGGGAT | CCTTATGGGA | 6734 |
| GGAATAGCAC | ACACTTAGAA | CAACATACCA | CAGTTTAAGA | GCATCATTTT | GAAAGGTAAT | 6794 |
| AAGCACTTTA | TTGCAATTAT | TCATTTAGAT | AAAGTTTGTA | TCTTAGGCAT | TAACCGTTTT | 6854 |
| TAAAGGATCC | CTAATCATCA | CTTAGGTGAA | ATGATAAACG | ACACATTTCT | GAGAAATGTT | 6914 |
| CAGGTCCAGT | GAACCGTAGC | AGGTTTATGG | GAATGATTTC | AAGGTAGCCA | AATAAACTCT | 6974 |
| GACTTTTGTT | TTGAATGTGG | TGGAGTCAGG | AGATTGTAGA | TGTGTAGTTT | GATTTAAACA | 7034 |
| CTATTGTAAA | CCTATCTTGC | CTATTGTGTG | GACACCAAAA | GAGACCAATG | AGCCTGTTTA | 7094 |
| TTTTCAGAGG | TCTAGGAATA | TGCATCTGTC | TGAGTAGATA | TACAGAACTA | ATCTATAAAC | 7154 |
| GGTTGGTAGT | AATATTTTAG | GATACAGTAA | CTTAAAGAAT | TATTGAGTGT | TTTAAATGTG | 7214 |
| CCCTGAAATG | TTGGCATGTC | ATTTCAGCGT | TCCCATTTGA | GTTGCTCTTG | TAATATTTTT | 7274 |
| GCACAAAAAG | GACTGAGAAA | AGACTGCTTT | GGTTGAAGAA | AACTATAATT | TGGTCTTATT | 7334 |
| TTAATGTCTC | CTGTGGAAAC | ACTGGAGGTA | AATTTGTTGG | CATAGTTACT | AATTCAGGAT | 7394 |

```
ATTTAAAACA GTGTTGAACA GCTCATCAGA AATTAAGCAA ACTTATATAT TTAAAAATTA      7454

AAAATCTTTT TTTCCATGTG ACTGAAAAAA AAAAAAAAAA AAAA                       7498
```

( 2 ) INFORMATION FOR SEQ ID NO:2:

( i ) SEQUENCE CHARACTERISTICS:
        ( A ) LENGTH: 855 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Val  Phe  Thr  Val  Ser  Cys  Ser  Lys  Met  Ser  Ser  Ile  Val  Asp  Arg
 1              5                   10                  15

Asp  Asp  Ser  Ser  Ile  Phe  Asp  Gly  Leu  Val  Glu  Glu  Asp  Lys  Asp
              20                  25                  30

Lys  Ala  Lys  Arg  Val  Ser  Arg  Asn  Lys  Ser  Glu  Lys  Lys  Arg  Arg  Asp
              35                  40                  45

Gln  Phe  Asn  Val  Leu  Ile  Lys  Glu  Leu  Gly  Ser  Met  Leu  Pro  Gly  Asn
      50                  55                  60

Ala  Arg  Lys  Met  Asp  Lys  Ser  Thr  Val  Leu  Gln  Lys  Ser  Ile  Asp  Phe
 65                  70                  75                  80

Leu  Arg  Lys  His  Lys  Glu  Thr  Thr  Ala  Gln  Ser  Asp  Ala  Ser  Glu  Ile
                  85                  90                  95

Arg  Gln  Asp  Trp  Lys  Pro  Thr  Phe  Leu  Ser  Asn  Glu  Glu  Phe  Thr  Gln
                 100                 105                 110

Leu  Met  Leu  Glu  Ala  Leu  Asp  Gly  Phe  Phe  Leu  Ala  Ile  Met  Thr  Asp
                 115                 120                 125

Gly  Ser  Ile  Ile  Tyr  Val  Ser  Glu  Ser  Val  Thr  Ser  Leu  Leu  Glu  His
     130                 135                 140

Leu  Pro  Ser  Asp  Leu  Val  Asp  Gln  Ser  Ile  Phe  Asn  Phe  Ile  Pro  Glu
145                      150                 155                 160

Gly  Glu  His  Ser  Glu  Val  Tyr  Lys  Ile  Leu  Ser  Thr  His  Leu  Leu  Glu
                 165                 170                 175

Ser  Asp  Ser  Leu  Thr  Pro  Glu  Tyr  Leu  Lys  Ser  Lys  Asn  Gln  Leu  Glu
                 180                 185                 190

Phe  Cys  Cys  His  Met  Leu  Arg  Gly  Thr  Ile  Asp  Pro  Lys  Glu  Pro  Ser
          195                 200                 205

Thr  Tyr  Glu  Tyr  Val  Arg  Phe  Ile  Gly  Asn  Phe  Lys  Ser  Leu  Thr  Ser
          210                 215                 220

Val  Ser  Thr  Ser  Thr  His  Asn  Gly  Phe  Glu  Gly  Thr  Ile  Gln  Arg  Thr
225                      230                 235                 240

His  Arg  Pro  Ser  Tyr  Glu  Asp  Arg  Val  Cys  Phe  Val  Ala  Thr  Val  Arg
                 245                 250                 255

Leu  Ala  Thr  Pro  Gln  Phe  Ile  Lys  Glu  Met  Cys  Thr  Val  Glu  Glu  Pro
                 260                 265                 270

Asn  Glu  Glu  Phe  Thr  Ser  Arg  His  Ser  Leu  Glu  Trp  Lys  Phe  Leu  Phe
                 275                 280                 285

Leu  Asp  His  Arg  Ala  Pro  Pro  Ile  Ile  Gly  Tyr  Leu  Pro  Phe  Glu  Val
     290                 295                 300

Leu  Gly  Thr  Ser  Gly  Tyr  Asp  Tyr  Tyr  His  Val  Asp  Asp  Leu  Glu  Asn
305                      310                 315                 320

Leu  Ala  Lys  Cys  His  Glu  His  Leu  Met  Gln  Tyr  Gly  Lys  Gly  Lys  Ser
                 325                 330                 335

Cys  Tyr  Tyr  Arg  Phe  Leu  Thr  Lys  Gly  Gln  Gln  Trp  Ile  Trp  Leu  Gln
```

-continued

```
                        340                      345                      350
Thr  His  Tyr  Tyr  Ile  Thr  Tyr  His  Gln  Trp  Asn  Ser  Arg  Pro  Glu  Phe
               355                      360                      365
Ile  Val  Cys  Thr  His  Thr  Val  Val  Ser  Tyr  Ala  Glu  Val  Arg  Ala  Glu
               370                      375                      380
Arg  Arg  Arg  Glu  Leu  Gly  Ile  Glu  Glu  Ser  Leu  Pro  Glu  Thr  Ala  Ala
385                      390                      395                      400
Asp  Lys  Ser  Gln  Asp  Ser  Gly  Ser  Asp  Asn  Arg  Ile  Asn  Thr  Val  Ser
               405                      410                      415
Leu  Lys  Glu  Ala  Leu  Glu  Arg  Phe  Asp  His  Ser  Pro  Thr  Pro  Ser  Ala
               420                      425                      430
Ser  Ser  Arg  Ser  Ser  Arg  Lys  Ser  Ser  His  Thr  Ala  Val  Ser  Asp  Pro
               435                      440                      445
Ser  Ser  Thr  Pro  Thr  Lys  Ile  Pro  Thr  Asp  Thr  Ser  Thr  Pro  Pro  Arg
450                      455                      460
Gln  His  Leu  Pro  Ala  His  Glu  Lys  Met  Thr  Gln  Arg  Arg  Ser  Ser  Phe
465                      470                      475                      480
Ser  Ser  Gln  Ser  Ile  Asn  Ser  Gln  Ser  Val  Gly  Pro  Ser  Leu  Thr  Gln
               485                      490                      495
Pro  Ala  Met  Ser  Gln  Ala  Ala  Asn  Leu  Pro  Ile  Pro  Gln  Gly  Met  Ser
               500                      505                      510
Gln  Phe  Gln  Phe  Ser  Ala  Gln  Leu  Gly  Ala  Met  Gln  His  Leu  Lys  Asp
               515                      520                      525
Gln  Leu  Glu  Gln  Arg  Thr  Arg  Met  Ile  Glu  Ala  Asn  Ile  His  Arg  Gln
               530                      535                      540
Gln  Glu  Glu  Leu  Arg  Lys  Ile  Gln  Glu  Gln  Leu  Gln  Met  Val  His  Gly
545                      550                      555                      560
Gln  Gly  Leu  Gln  Met  Phe  Leu  Gln  Gln  Ser  Asn  Pro  Gly  Leu  Asn  Phe
               565                      570                      575
Gly  Ser  Val  Gln  Leu  Ser  Ser  Gly  Asn  Ser  Asn  Ile  Gln  Gln  Leu  Thr
               580                      585                      590
Pro  Val  Asn  Met  Gln  Gly  Gln  Val  Val  Pro  Ala  Asn  Gln  Val  Gln  Ser
               595                      600                      605
Gly  His  Ile  Ser  Thr  Gly  Gln  His  Met  Ile  Gln  Gln  Gln  Thr  Leu  Gln
               610                      615                      620
Ser  Thr  Ser  Thr  Gln  Gln  Ser  Gln  Gln  Ser  Val  Met  Ser  Gly  His  Ser
625                      630                      635                      640
Gln  Gln  Thr  Ser  Leu  Pro  Ser  Gln  Thr  Pro  Ser  Thr  Leu  Thr  Ala  Pro
               645                      650                      655
Leu  Tyr  Asn  Thr  Met  Val  Ile  Ser  Gln  Pro  Ala  Ala  Gly  Ser  Met  Val
               660                      665                      670
Gln  Ile  Pro  Ser  Ser  Met  Pro  Gln  Asn  Ser  Thr  Gln  Ser  Ala  Thr  Val
               675                      680                      685
Thr  Thr  Phe  Thr  Gln  Asp  Arg  Gln  Ile  Arg  Phe  Ser  Gln  Gly  Gln  Gln
690                      695                      700
Leu  Val  Thr  Lys  Leu  Val  Thr  Ala  Pro  Val  Ala  Cys  Gly  Ala  Val  Met
705                      710                      715                      720
Val  Pro  Ser  Thr  Met  Leu  Met  Gly  Gln  Val  Val  Thr  Ala  Tyr  Pro  Thr
               725                      730                      735
Phe  Ala  Thr  Gln  Gln  Gln  Gln  Ala  Gln  Thr  Leu  Ser  Val  Thr  Gln  Gln
               740                      745                      750
Gln  Gln  Gln  Gln  Gln  Gln  Gln  Pro  Pro  Gln  Gln  Gln  Gln  Gln  Gln  Gln
               755                      760                      765
```

| Gln | Ser | Ser | Gln | Glu | Gln | Gln | Leu | Pro | Ser | Val | Gln | Gln | Pro | Ala | Gln |
|-----|-----|-----|-----|-----|-----|-----|-----|-----|-----|-----|-----|-----|-----|-----|-----|
|     | 770 |     |     |     | 775 |     |     |     |     | 780 |     |     |     |     |     |
| Ala | Gln | Leu | Gly | Gln | Pro | Pro | Gln | Gln | Phe | Leu | Gln | Thr | Ser | Arg | Leu |
| 785 |     |     |     |     | 790 |     |     |     |     | 795 |     |     |     |     | 800 |
| Leu | His | Gly | Asn | Pro | Ser | Thr | Gln | Leu | Ile | Leu | Ser | Ala | Ala | Phe | Pro |
|     |     |     |     | 805 |     |     |     |     | 810 |     |     |     |     | 815 |     |
| Leu | Gln | Gln | Ser | Thr | Phe | Pro | Pro | Ser | His | His | Gln | Gln | His | Gln | Pro |
|     |     |     | 820 |     |     |     |     | 825 |     |     |     |     | 830 |     |     |
| Gln | Gln | Gln | Gln | Gln | Leu | Pro | Arg | His | Arg | Thr | Asp | Ser | Leu | Thr | Asp |
|     |     | 835 |     |     |     |     | 840 |     |     |     |     | 845 |     |     |     |
| Pro | Ser | Lys | Val | Gln | Pro | Gln |
|-----|-----|-----|-----|-----|-----|-----|
|     | 850 |     |     |     |     | 855 |

( 2 ) INFORMATION FOR SEQ ID NO:3:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GCTGGAGAGA GGAAACCCCG GACGGCGAGA GCGCGAAGGA AATCTGGCCG CCGCCGCGCA    60
CGCGCTCCCG                                                           70
```

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
GCGCTCCCGG TGAGTGCG                                                  18
```

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
TCAGGCACGG TGAGGACG                                                  18
```

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
ACCAGCAAGG TAATTTCC                                                  18
```

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GTGAAAGAGG TAAAGGCG                                             18

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TGTTGACAGG TATGTTTT                                             18

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

AGCAAAAAGG TAGTTAGC                                             18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AACATAAAGG TAAAGTGC                                             18

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

ATGTTAGAGG TATGTTCA                                             18

( 2 ) INFORMATION FOR SEQ ID NO:12:

( i ) SEQUENCE CHARACTERISTICS:
        ( A ) LENGTH: 18 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

CATTTACCAG TAAGTATG 18

(2) INFORMATION FOR SEQ ID NO:13:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

ACTTAAAATG TAAGTAGG 18

(2) INFORMATION FOR SEQ ID NO:14:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

TAACCAGTGG TAAGTTAA 18

(2) INFORMATION FOR SEQ ID NO:15:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

TTCATCAAGG TATGCTTC 18

(2) INFORMATION FOR SEQ ID NO:16:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

AGATCACAGG TAACATTA 18

(2) INFORMATION FOR SEQ ID NO:17:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:17:

ACGAGCACTG TAAGTAGC 18

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

TGTAGTAAGG TAATAACT 18

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GCTGACAAAG TATGTTTC 18

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

ACCCTTCCTG TGAGTGCC 18

( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

AGCAGTCAGG TACGCCTT 18

( 2 ) INFORMATION FOR SEQ ID NO:22:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

ATGTCACAGG TATTTTTG 18

( 2 ) INFORMATION FOR SEQ ID NO:23:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

GGGCTACAGG TAACTTAT        18

( 2 ) INFORMATION FOR SEQ ID NO:24:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

TCAACTCAGG TAATTGAC        18

( 2 ) INFORMATION FOR SEQ ID NO:25:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

ACAGATAAGG TAGTTGTC        18

( 2 ) INFORMATION FOR SEQ ID NO:26:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TTCTTACAGG TAACCCCC        18

( 2 ) INFORMATION FOR SEQ ID NO:27:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

TCTGGTGTTT TCTATTGCAG TGAAAGAAA        29

( 2 ) INFORMATION FOR SEQ ID NO:28:

( i ) SEQUENCE CHARACTERISTICS:
        ( A ) LENGTH: 29 base pairs (B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:28:

CTTTTGTTTT TTTAAAACAG AGTTCTGAT 29

(2) INFORMATION FOR SEQ ID NO:29:

(i) SEQUENCE CHARACTERISTICS:
(A) LENGTH: 29 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:29:

ATGTTTTCTT TTCTCACAAG GAGAAGTAC 29

(2) INFORMATION FOR SEQ ID NO:30:

(i) SEQUENCE CHARACTERISTICS:
(A) LENGTH: 29 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:30:

CTCTGTCTTT TCTCTTGTAG AGATGACAG 29

(2) INFORMATION FOR SEQ ID NO:31:

(i) SEQUENCE CHARACTERISTICS:
(A) LENGTH: 29 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:31:

TAATTTCTTT TTCTTCATAG AGTATCTAG 29

(2) INFORMATION FOR SEQ ID NO:32:

(i) SEQUENCE CHARACTERISTICS:
(A) LENGTH: 29 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:32:

ACGTGTCAAT CTGTTTACAG AGACCACTG 29

(2) INFORMATION FOR SEQ ID NO:33:

(i) SEQUENCE CHARACTERISTICS:
(A) LENGTH: 29 base pairs
(B) TYPE: nucleic acid
(C) STRANDEDNESS: single
(D) TOPOLOGY: linear (i i) MOLECULE TYPE: DNA (genomic)

( x i ) SEQUENCE DESCRIPTION: SEQ ID NO:33:

ACCATTATGT TTAATTTCAG GCTCTTGAT 29

( 2 ) INFORMATION FOR SEQ ID NO:34:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

TTTTTTTTT TATTTTCAG TCTGATCTT 29

( 2 ) INFORMATION FOR SEQ ID NO:35:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

CTTTTTATCA CTTATTCCAG CAAAAAATC 29

( 2 ) INFORMATION FOR SEQ ID NO:36:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

ATGTCTCCTT GCTGTTTAG TATCAACTT 29

( 2 ) INFORMATION FOR SEQ ID NO:37:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

ACTTGTTAAT TTGTTTGTAG GAAATGTGT 29

( 2 ) INFORMATION FOR SEQ ID NO:38:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

ATTATTACTG TATAATTTAG GGCACCACC 29

( 2 ) INFORMATION FOR SEQ ID NO:39:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

TTTTATTTTT TTATTTTAG TAATGCAAT     29

( 2 ) INFORMATION FOR SEQ ID NO:40:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

TTGGTTCTTT CCATTTGTAG TTATTGCAG     29

( 2 ) INFORMATION FOR SEQ ID NO:41:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

TGTTCCTCTT ATCTCCTTAG AGCCAAGAT     29

( 2 ) INFORMATION FOR SEQ ID NO:42:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

TCTCTGTTGA CTGTCTTTAG CCACACCGA     29

( 2 ) INFORMATION FOR SEQ ID NO:43:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

ATCTTTTATT TTGCTTCTAG TCCATAAAC     29

( 2 ) INFORMATION FOR SEQ ID NO:44:

( i ) SEQUENCE CHARACTERISTICS:
        ( A ) LENGTH: 29 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:44:

CTTTCCATGT GCTGCTTCAG TTTCAGTTT 29

( 2 ) INFORMATION FOR SEQ ID NO:45:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:45:

TGTGATCTTT GTTTTCAAAG ATGTTTTTG 29

( 2 ) INFORMATION FOR SEQ ID NO:46:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:46:

TTCCATACGA TCTTTTCTAG CAGAGTCAA 29

( 2 ) INFORMATION FOR SEQ ID NO:47:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:47:

TATTTTGTTT TCTCTCACAG ATTTTCTCA 29

( 2 ) INFORMATION FOR SEQ ID NO:48:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:48:

ATCATCCTTT TTGTTTTTAG ACATCTAGG 29

( 2 ) INFORMATION FOR SEQ ID NO:49:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

(xi) SEQUENCE DESCRIPTION: SEQ ID NO:49:

GGGCTACAGG TAACTTAT    18

(2) INFORMATION FOR SEQ ID NO:50:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

GGGCTACAGG TTACTTAT    18

(2) INFORMATION FOR SEQ ID NO:51:

(i) SEQUENCE CHARACTERISTICS:
        (A) LENGTH: 747 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:51:

```
Met Asp Glu Asp Glu Lys Asp Arg Ala Lys Arg Ala Ser Arg Asn Lys
  1               5                  10                  15
Ser Glu Lys Lys Arg Arg Asp Gln Phe Asn Val Leu Ile Lys Glu Leu
             20                  25                  30
Ser Ser Met Leu Pro Gly Asn Ile Arg Lys Met Asp Lys Ile Thr Val
         35                  40                  45
Leu Glu Lys Val Ile Gly Phe Leu Gln Lys His Asn Glu Val Ser Ala
     50                  55                  60
Gln Thr Glu Ile Cys Asp Ile Gln Gln Asp Trp Lys Pro Ser Phe Leu
 65                  70                  75                  80
Ser Asn Glu Glu Phe Thr Gln Leu Met Glu Ala Leu Asp Gly Phe
                 85                  90                  95
Ile Ala Val Thr Thr Asp Gly Ser Ile Ile Tyr Val Ser Asp Ser Ile
             100                 105                 110
Thr Pro Leu Leu Gly His Leu Pro Ser Asp Val Met Asp Gln Asn Leu
         115                 120                 125
Leu Asn Phe Leu Pro Glu Gln Glu His Ser Glu Val Tyr Lys Ile Leu
     130                 135                 140
Ser Ser His Met Leu Val Thr Asp Ser Pro Ser Pro Glu Tyr Leu Lys
145                 150                 155                 160
Ser Asp Asn Asp Leu Glu Phe Tyr Cys His Leu Leu Arg Gly Ser Leu
                165                 170                 175
Asn Pro Lys Glu Phe Pro Thr Tyr Glu Tyr Ile Lys Phe Val Gly Asn
            180                 185                 190
Phe Arg Ser Tyr Asn Asn Val Pro Ser Pro Ser Cys Asn Gly Phe Asp
        195                 200                 205
Asn Thr Leu Ser Arg Pro Cys Arg Val Pro Leu Gly Lys Val Cys Phe
    210                 215                 220
Ile Ala Thr Val Arg Leu Ala Thr Pro Gln Phe Leu Lys Glu Met Cys
225                 230                 235                 240
Val Asp Glu Pro Leu Glu Glu Phe Thr Ser Arg His Ser Leu Glu Trp
                245                 250                 255
```

```
Lys  Phe  Leu  Phe  Leu  Asp  His  Arg  Ala  Pro  Pro  Ile  Ile  Gly  Tyr  Leu
               260                 265                           270

Pro  Phe  Glu  Val  Leu  Gly  Thr  Ser  Gly  Tyr  Asp  Tyr  Tyr  His  Ile  Asp
          275                 280                      285

Asp  Leu  Glu  Leu  Leu  Ala  Arg  Cys  His  Gln  His  Leu  Met  Gln  Phe  Gly
     290                      295                 300

Lys  Gly  Lys  Ser  Cys  Cys  Tyr  Arg  Phe  Leu  Thr  Lys  Gly  Gln  Gln  Trp
305                      310                      315                      320

Ile  Trp  Leu  Gln  Thr  His  Tyr  Tyr  Ile  Thr  Tyr  His  Gln  Trp  Asn  Ser
                    325                      330                     335

Lys  Pro  Glu  Phe  Ile  Val  Cys  Thr  His  Ser  Val  Val  Ser  Tyr  Ala  Asp
               340                 345                          350

Val  Arg  Val  Glu  Arg  Arg  Gln  Glu  Leu  Ala  Leu  Glu  Asp  Pro  Pro  Glu
          355                 360                      365

Ala  His  Ser  Ala  Lys  Lys  Asp  Ser  Ser  Leu  Glu  Pro  Arg  Gln  Phe  Asn
     370                 375                      380

Ala  Leu  Asp  Gly  Ala  Ser  Gly  Leu  Ser  Pro  Ser  Pro  Ser  Ala  Ser  Ser
385                      390                      395                      400

Arg  Ser  Ser  His  Lys  Ser  Ser  His  Thr  Ala  Met  Ser  Glu  Pro  Ile  Ser
               405                 410                          415

Thr  Pro  Thr  Lys  Leu  Met  Ala  Glu  Ser  Thr  Ala  Leu  Pro  Arg  Ala  Thr
               420                 425                           430

Leu  Pro  Gln  Glu  Leu  Pro  Val  Gly  Leu  Ser  Gln  Ala  Ala  Thr  Met  Pro
          435                 440                      445

Leu  Ser  Ser  Ser  Cys  Asp  Leu  Thr  Gln  Gln  Leu  Leu  Gln  Pro  Gln  Thr
          450                 455                      460

Leu  Gln  Ser  Pro  Ala  Pro  Gln  Phe  Ser  Ala  Gln  Phe  Ser  Met  Phe  Gln
465                      470                      475                      480

Thr  Ile  Lys  Asp  Gln  Leu  Glu  Gln  Arg  Thr  Arg  Ile  Leu  Gln  Ala  Asn
               485                 490                          495

Ile  Arg  Trp  Gln  Gln  Glu  Glu  Leu  His  Lys  Ile  Gln  Glu  Gln  Leu  Cys
               500                 505                           510

Leu  Val  Gln  Asp  Ser  Asn  Val  Gln  Met  Phe  Leu  Gln  Gln  Pro  Ala  Val
          515                 520                      525

Ser  Leu  Ser  Phe  Ser  Ser  Ile  Gln  Arg  Pro  Ala  Gln  Gln  Leu  Gln
     530                 535                      540

Gln  Arg  Ala  Ala  Gln  Pro  Gln  Leu  Val  Gln  Leu  Gln  Gly  Gln  Ile  Ser
545                      550                      555                      560

Thr  Gln  Val  Thr  Gln  His  Leu  Leu  Arg  Glu  Ser  Ser  Val  Ile  Ser  Gln
                    565                 570                           575

Gly  Pro  Lys  Pro  Met  Arg  Ser  Ser  Gln  Leu  Ser  Gly  Arg  Ser  Ser  Ser
               580                      585                     590

Leu  Ser  Pro  Phe  Ser  Ser  Thr  Leu  Pro  Pro  Leu  Leu  Thr  Thr  Pro  Ala
          595                      600                     605

Ser  Thr  Pro  Gln  Asp  Ser  Gln  Cys  Gln  Pro  Ser  Pro  Asp  Phe  His  Asp
     610                 615                      620

Arg  Gln  Leu  Arg  Leu  Leu  Leu  Ser  Gln  Pro  Ile  Gln  Pro  Met  Met  Pro
625                           630                 635                      640

Gly  Ser  Cys  Asp  Ala  Arg  Gln  Pro  Ser  Glu  Val  Ser  Arg  Thr  Gly  Arg
               645                      650                           655

Gln  Val  Lys  Tyr  Ala  Gln  Ser  Gln  Phe  Pro  Asp  His  Pro  Asn  Ser  Ser
               660                 665                           670

Pro  Val  Leu  Leu  Met  Gly  Gln  Ala  Val  Leu  His  Pro  Ser  Phe  Pro  Ala
```

|     |     |     |     |     | 675 |     |     |     | 680 |     |     |     |     | 685 |     |
| --- | --- | --- | --- | --- | --- | --- | --- | --- | --- | --- | --- | --- | --- | --- | --- |
| Ser | Pro | Ser | Pro | Leu | Gln | Pro | Ala | Gln | Ala | Gln | Gln | Pro | Pro | Pro |
|     | 690 |     |     |     |     | 695 |     |     |     |     | 700 |     |     |     |
| Gln | Ala | Pro | Thr | Ser | Leu | His | Ser | Glu | Gln | Asp | Ser | Leu | Leu | Leu | Ser |
| 705 |     |     |     |     | 710 |     |     |     |     | 715 |     |     |     |     | 720 |
| Thr | Phe | Ser | Gln | Gln | Pro | Gly | Thr | Leu | Gly | Tyr | Gln | Gln | Pro | Gln | Pro |
|     |     |     |     | 725 |     |     |     |     | 730 |     |     |     |     | 735 |     |
| Arg | Pro | Arg | Arg | Val | Ser | Leu | Ser | Glu | Ser | Pro |
|     |     |     |     | 740 |     |     |     |     | 745 |     |

( 2 ) INFORMATION FOR SEQ ID NO:52:

( i ) SEQUENCE CHARACTERISTICS:
        ( A ) LENGTH: 824 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:52:

| Met | Asp | Glu | Asp | Glu | Lys | Asp | Arg | Ala | Lys | Arg | Ala | Ser | Arg | Asn | Lys |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ser | Glu | Lys | Lys | Arg | Arg | Asp | Gln | Phe | Asn | Val | Leu | Ile | Lys | Glu | Leu |
|     |     |     | 20  |     |     |     |     | 25  |     |     |     |     | 30  |     |     |
| Ser | Ser | Met | Leu | Pro | Gly | Asn | Ile | Arg | Lys | Met | Asp | Lys | Ile | Thr | Val |
|     |     | 35  |     |     |     |     | 40  |     |     |     |     | 45  |     |     |     |
| Leu | Glu | Lys | Val | Ile | Gly | Phe | Leu | Gln | Lys | His | Asn | Glu | Val | Ser | Ala |
|     | 50  |     |     |     |     | 55  |     |     |     |     | 60  |     |     |     |     |
| Gln | Thr | Glu | Ile | Cys | Asp | Ile | Gln | Gln | Asp | Trp | Lys | Pro | Ser | Phe | Leu |
| 65  |     |     |     |     | 70  |     |     |     |     | 75  |     |     |     |     | 80  |
| Ser | Asn | Glu | Glu | Phe | Thr | Gln | Leu | Met | Leu | Glu | Ala | Leu | Asp | Gly | Phe |
|     |     |     |     | 85  |     |     |     |     | 90  |     |     |     |     | 95  |     |
| Ile | Ile | Ala | Val | Thr | Thr | Asp | Gly | Ser | Ile | Ile | Tyr | Val | Ser | Asp | Ser |
|     |     |     |     | 100 |     |     |     |     | 105 |     |     |     |     | 110 |     |
| Thr | Thr | Pro | Leu | Leu | Gly | His | Leu | Pro | Ser | Asp | Val | Met | Asp | Gln | Asn |
|     |     | 115 |     |     |     |     | 120 |     |     |     |     | 125 |     |     |     |
| Leu | Leu | Asn | Phe | Leu | Pro | Glu | Gln | Glu | His | Ser | Glu | Val | Tyr | Lys | Ile |
|     | 130 |     |     |     |     | 135 |     |     |     |     | 140 |     |     |     |     |
| Leu | Ser | Ser | His | Met | Leu | Val | Thr | Asp | Ser | Pro | Ser | Pro | Glu | Tyr | Leu |
| 145 |     |     |     |     | 150 |     |     |     |     | 155 |     |     |     |     | 160 |
| Lys | Ser | Asp | Ser | Asp | Leu | Glu | Phe | Tyr | Cys | His | Leu | Leu | Arg | Gly | Ser |
|     |     |     |     | 165 |     |     |     |     | 170 |     |     |     |     | 175 |     |
| Leu | Asn | Pro | Lys | Glu | Phe | Pro | Thr | Tyr | Glu | Tyr | Ile | Lys | Phe | Val | Gly |
|     |     |     | 180 |     |     |     |     | 185 |     |     |     |     | 190 |     |     |
| Asn | Phe | Arg | Ser | Tyr | Asn | Asn | Val | Pro | Ser | Pro | Ser | Cys | Asn | Gly | Phe |
|     |     | 195 |     |     |     |     | 200 |     |     |     |     | 205 |     |     |     |
| Asp | Asn | Thr | Leu | Ser | Arg | Pro | Cys | Arg | Val | Pro | Leu | Gly | Lys | Glu | Val |
|     | 210 |     |     |     |     | 215 |     |     |     |     | 220 |     |     |     |     |
| Cys | Phe | Ile | Ala | Thr | Val | Arg | Leu | Ala | Thr | Pro | Gln | Phe | Leu | Lys | Glu |
| 225 |     |     |     |     | 230 |     |     |     |     | 235 |     |     |     |     | 240 |
| Met | Cys | Ile | Val | Asp | Glu | Pro | Leu | Glu | Glu | Phe | Thr | Ser | Arg | His | Ser |
|     |     |     |     | 245 |     |     |     |     | 250 |     |     |     |     | 255 |     |
| Leu | Glu | Trp | Lys | Phe | Leu | Phe | Leu | Asp | His | Arg | Ala | Pro | Pro | Ile | Ile |
|     |     |     | 260 |     |     |     |     | 265 |     |     |     |     | 270 |     |     |
| Gly | Tyr | Leu | Pro | Phe | Glu | Val | Leu | Gly | Thr | Ser | Gly | Tyr | Asp | Tyr | Tyr |
|     |     | 275 |     |     |     |     | 280 |     |     |     |     | 285 |     |     |     |

```
His  Ile  Asp  Asp  Leu  Glu  Leu  Leu  Ala  Arg  Cys  His  Gln  His  Leu  Met
     290                 295                      300

Gln  Phe  Gly  Ile  Gly  Lys  Ser  Cys  Cys  Tyr  Arg  Phe  Leu  Thr  Lys  Gly
305                      310                      315                      320

Gln  Gln  Trp  Ile  Trp  Leu  Gln  Thr  His  Tyr  Ile  Thr  Tyr  His  Gln
                         325                 330                      335

Trp  Asn  Ser  Lys  Pro  Glu  Phe  Ile  Val  Cys  Thr  His  Ser  Val  Val  Ser
               340                      345                      350

Tyr  Ala  Asp  Val  Arg  Val  Glu  Arg  Arg  Gln  Glu  Leu  Ala  Leu  Glu  Asp
          355                      360                      365

Pro  Pro  Ser  Glu  Ala  Leu  His  Ser  Ser  Ala  Leu  Lys  Asp  Lys  Gly  Ser
370                           375                      380

Ser  Leu  Glu  Pro  Arg  Gln  His  Phe  Asn  Ala  Leu  Asp  Val  Gly  Ala  Ser
385                      390                      395                      400

Gly  Leu  Asn  Thr  Ser  His  Ser  Pro  Ser  Ala  Ser  Ser  Arg  Ser  Ser  His
                    405                      410                      415

Lys  Ser  Ser  His  Thr  Ala  Met  Ser  Glu  Pro  Ile  Ser  Thr  Pro  Thr  Lys
               420                      425                      430

Leu  Met  Ala  Glu  Ala  Ser  Thr  Pro  Ala  Leu  Pro  Arg  Ser  Ala  Thr  Leu
          435                      440                      445

Pro  Gln  Glu  Leu  Pro  Val  Pro  Gly  Leu  Ser  Gln  Ala  Thr  Met  Pro
     450                      455                      460

Ala  Pro  Leu  Pro  Ser  Pro  Leu  Ser  Cys  Asp  Leu  Thr  Gln  Gln  Leu  Leu
465                      470                      475                      480

Pro  Gln  Thr  Val  Leu  Gln  Ser  Thr  Pro  Ala  Pro  Met  Ala  Gln  Phe  Ser
                    485                      490                      495

Ala  Gln  Phe  Ser  Met  Phe  Gln  Thr  Ile  Lys  Asp  Gln  Leu  Glu  Gln  Arg
               500                      505                      510

Thr  Arg  Ile  Leu  Gln  Ala  Asn  Ile  Arg  Trp  Gln  Gln  Glu  Glu  Leu  His
               515                      520                      525

Lys  Ile  Gln  Glu  Gln  Leu  Cys  Leu  Val  Gln  Asp  Ser  Asn  Val  Gln  Met
     530                      535                      540

Phe  Leu  Gln  Gln  Pro  Ala  Val  Ser  Leu  Ser  Phe  Ser  Ser  Ile  Gln  Arg
545                      550                      555                      560

Pro  Glu  Ala  Gln  Gln  Gln  Leu  Gln  Gln  Arg  Ser  Ala  Ala  Val  Thr  Gln
                    565                      570                      575

Pro  Gln  Leu  Gly  Ala  Gly  Pro  Gln  Leu  Pro  Gly  Gln  Ile  Ser  Ser  Ala
               580                      585                      590

Gln  Val  Thr  Ser  Gln  His  Leu  Leu  Arg  Glu  Ser  Ser  Val  Ile  Ser  Thr
          595                      600                      605

Gln  Gly  Pro  Lys  Pro  Met  Arg  Ser  Ser  Gln  Leu  Met  Gln  Ser  Ser  Gly
610                      615                      620

Arg  Ser  Gly  Ser  Ser  Leu  Val  Ser  Pro  Phe  Ser  Ala  Thr  Ala  Ala
625                      630                      635                      640

Leu  Pro  Pro  Ser  Leu  Asn  Leu  Thr  Thr  Pro  Ala  Ser  Thr  Ser  Gln  Asp
                    645                      650                      655

Ala  Ser  Gln  Cys  Gln  Pro  Ser  Pro  Asp  Phe  Ser  His  Asp  Arg  Gln  Leu
               660                      665                      670

Arg  Leu  Leu  Leu  Ser  Gln  Pro  Ile  Gln  Pro  Met  Met  Pro  Gly  Ser  Cys
          675                      680                      685

Asp  Ala  Arg  Gln  Pro  Ser  Glu  Val  Ser  Arg  Thr  Gly  Arg  Gln  Val  Lys
690                      695                      700

Tyr  Ala  Gln  Ser  Gln  Thr  Val  Phe  Gln  Asn  Pro  Asp  Ala  His  Pro  Ala
```

|     |     |     |     |     |     |     |     |     |     |     |     |     |     |     |     |
|---|---|---|---|---|---|---|---|---|---|---|---|---|---|---|---|
| 705 |  |  |  |  | 710 |  |  |  |  | 715 |  |  |  |  | 720 |

Asn Ser Ser Ser Ala Pro Met Pro Val Leu Met Gly Gln Ala Val
                    725             730             735

Leu His Pro Ser Phe Pro Ala Ser Gln Pro Ser Pro Leu Gln Pro Ala
                740             745             750

Gln Ala Arg Gln Gln Pro Pro Gln His Tyr Leu Gln Val Gln Ala Pro
            755             760             765

Thr Ser Leu His Ser Glu Gln Gln Asp Ser Leu Leu Leu Ser Thr Tyr
770                 775             780

Ser Gln Gln Pro Gly Thr Leu Gly Tyr Pro Gln Pro Pro Pro Ala Gln
785                 790             795                     800

Pro Gln Pro Leu Arg Pro Pro Arg Arg Val Ser Ser Leu Ser Glu Ser
                805             810             815

Ser Gly Leu Gln Gln Pro Pro Arg
            820

( 2 ) INFORMATION FOR SEQ ID NO:53:

( i ) SEQUENCE CHARACTERISTICS:
        ( A ) LENGTH: 816 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:53:

Met Asp Glu Asp Glu Lys Asp Arg Ala Lys Arg Ala Ser Arg Asn Lys
1               5                   10                  15

Ser Glu Lys Lys Arg Arg Asp Gln Phe Asn Val Leu Ile Lys Glu Leu
                20              25                  30

Ser Ser Met Leu Pro Gly Asn Ile Arg Lys Met Asp Lys Ile Thr Val
        35              40                  45

Leu Glu Lys Val Ile Gly Phe Leu Gln Lys His Asn Glu Val Ser Ala
    50                  55                  60

Gln Thr Glu Ile Cys Asp Ile Gln Gln Asp Trp Lys Pro Ser Phe Leu
65              70                  75                      80

Ser Asn Glu Glu Phe Thr Gln Leu Met Leu Glu Ala Leu Asp Gly Phe
                85                  90                  95

Val Ile Val Val Thr Thr Asp Gly Ser Ile Ile Tyr Val Ser Asp Ser
            100                 105                 110

Thr Thr Pro Leu Leu Gly His Leu Pro Ala Asp Val Met Asp Gln Asn
        115                 120                 125

Leu Leu Asn Phe Leu Pro Glu Gln Glu His Ser Glu Val Tyr Lys Ile
    130                 135                 140

Leu Ser Ser His Met Leu Val Thr Asp Ser Pro Ser Pro Glu Phe Leu
145                 150                 155                 160

Lys Ser Asp Asn Asp Leu Glu Phe Tyr Cys His Leu Leu Arg Gly Ser
                165                 170                 175

Leu Asn Pro Lys Glu Phe Pro Thr Tyr Glu Tyr Ile Lys Phe Val Gly
                180                 185                 190

Asn Phe Arg Ser Tyr Asn Asn Val Pro Ser Pro Ser Cys Asn Gly Phe
            195                 200                 205

Asp Asn Thr Leu Ser Arg Pro Cys His Val Pro Leu Gly Lys Asp Val
            210                 215                 220

Cys Phe Ile Ala Thr Val Arg Leu Ala Thr Pro Gln Phe Leu Lys Glu
225                 230                 235                 240

-continued

| | | | | | | | | | | | | | | |
|---|---|---|---|---|---|---|---|---|---|---|---|---|---|---|
| Met | Cys | Val | Ala | Asp | Glu | Pro | Leu | Glu | Phe | Thr | Ser | Arg | His | Ser |
| | | | | 245 | | | | 250 | | | | | 255 | |
| Leu | Glu | Trp | Lys | Phe | Leu | Phe | Leu | Asp | His | Arg | Ala | Pro | Ile | Ile |
| | | | 260 | | | | 265 | | | | | 270 | | |
| Gly | Tyr | Leu | Pro | Phe | Glu | Val | Leu | Gly | Thr | Ser | Gly | Tyr | Asn | Tyr | Tyr |
| | | | 275 | | | | 280 | | | | | 285 | | |
| His | Ile | Asp | Asp | Leu | Glu | Leu | Ala | Arg | Cys | His | Gln | His | Leu | Met |
| | 290 | | | | | 295 | | | | 300 | | | | |
| Gln | Phe | Gly | Lys | Gly | Lys | Ser | Cys | Cys | Tyr | Arg | Phe | Leu | Thr | Lys | Gly |
| 305 | | | | | 310 | | | | 315 | | | | | 320 |
| Gln | Gln | Trp | Ile | Trp | Leu | Gln | Thr | His | Tyr | Ile | Thr | Tyr | His | Gln |
| | | | | 325 | | | | 330 | | | | | 335 | |
| Trp | Asn | Ser | Lys | Pro | Glu | Phe | Ile | Val | Cys | Thr | His | Ser | Val | Val | Ser |
| | | | 340 | | | | 345 | | | | | 350 | | |
| Tyr | Ala | Asp | Val | Arg | Val | Glu | Arg | Arg | Gln | Glu | Leu | Ala | Leu | Glu | Asp |
| | | 355 | | | | 360 | | | | | 365 | | | |
| Pro | Pro | Thr | Glu | Ala | Met | His | Pro | Ser | Ala | Val | Lys | Glu | Lys | Asp | Ser |
| | 370 | | | | | 375 | | | | | 380 | | | |
| Ser | Leu | Glu | Pro | Pro | Gln | Pro | Phe | Asn | Ala | Leu | Asp | Met | Gly | Ala | Ser |
| 385 | | | | | 390 | | | | 395 | | | | | 400 |
| Gly | Leu | Pro | Ser | Ser | Pro | Ser | Pro | Ser | Ala | Ser | Ser | Arg | Ser | Ser | His |
| | | | | 405 | | | | 410 | | | | | 415 | |
| Lys | Ser | Ser | His | Thr | Ala | Met | Ser | Glu | Pro | Ile | Ser | Thr | Pro | Thr | Lys |
| | | | 420 | | | | 425 | | | | | 430 | | |
| Leu | Met | Ala | Glu | Asn | Ser | Thr | Thr | Ala | Leu | Pro | Arg | Pro | Ala | Thr | Leu |
| | | 435 | | | | 440 | | | | | 445 | | | |
| Pro | Gln | Glu | Leu | Pro | Val | Gln | Gly | Leu | Ser | Gln | Ala | Ala | Thr | Met | Pro |
| | 450 | | | | | 455 | | | | | 460 | | | |
| Thr | Ala | Leu | His | Ser | Ser | Ala | Ser | Cys | Asp | Leu | Thr | Lys | Gln | Leu | Leu |
| 465 | | | | | 470 | | | | 475 | | | | | 480 |
| Leu | Gln | Ser | Leu | Pro | Gln | Thr | Gly | Leu | Gln | Ser | Pro | Pro | Ala | Pro | Val |
| | | | | 485 | | | | 490 | | | | | 495 | |
| Thr | Gln | Phe | Ser | Ala | Gln | Phe | Ser | Met | Phe | Gln | Thr | Ile | Lys | Asp | Gln |
| | | | 500 | | | | 505 | | | | | 510 | | |
| Leu | Glu | Gln | Arg | Thr | Arg | Ile | Leu | Gln | Ala | Asn | Ile | Arg | Trp | Gln | Gln |
| | | 515 | | | | 520 | | | | | 525 | | | |
| Glu | Glu | Leu | His | Lys | Ile | Gln | Glu | Gln | Leu | Cys | Leu | Val | Gln | Asp | Ser |
| | 530 | | | | | 535 | | | | | 540 | | | |
| Asn | Val | Gln | Met | Phe | Leu | Gln | Gln | Pro | Ala | Val | Ser | Leu | Ser | Phe | Ser |
| 545 | | | | | 550 | | | | 555 | | | | | 560 |
| Ser | Ile | Gln | Arg | Pro | Ala | Ala | Gln | Gln | Gln | Leu | Gln | Gln | Arg | Pro | Ala |
| | | | | 565 | | | | 570 | | | | | 575 | |
| Ala | Pro | Ser | Gln | Pro | Gln | Leu | Val | Val | Asn | Thr | Pro | Leu | Gln | Gly | Gln |
| | | | 580 | | | | 585 | | | | | 590 | | |
| Ile | Thr | Ser | Thr | Gln | Val | Thr | Asn | Gln | His | Leu | Leu | Arg | Glu | Ser | Asn |
| | | 595 | | | | 600 | | | | | 605 | | | |
| Val | Ile | Ser | Ala | Gln | Gly | Pro | Lys | Pro | Met | Arg | Ser | Ser | Gln | Leu | Leu |
| | 610 | | | | | 615 | | | | | 620 | | | |
| Pro | Ala | Ser | Gly | Arg | Ser | Leu | Ser | Ser | Leu | Pro | Ser | Gln | Phe | Ser | Ser |
| 625 | | | | | 630 | | | | 635 | | | | | 640 |
| Thr | Ala | Ser | Val | Leu | Pro | Pro | Gly | Leu | Ser | Leu | Thr | Thr | Ile | Ala | Pro |
| | | | | 645 | | | | 650 | | | | | 655 | |
| Thr | Pro | Gln | Asp | Asp | Ser | Gln | Cys | Gln | Pro | Ser | Pro | Asp | Phe | Gly | His |

-continued

| | | | | | | | 660 | | | | | 665 | | | | | 670 | | |
|---|---|---|---|---|---|---|---|---|---|---|---|---|---|---|---|---|---|---|---|
| Asp | Arg | Gln | Leu | Arg | Leu | Leu | Leu | Ser | Gln | Pro | Ile | Gln | Pro | Met | Met |
| | | 675 | | | | | 680 | | | | | 685 | | | |
| Pro | Gly | Ser | Cys | Asp | Ala | Arg | Gln | Pro | Ser | Glu | Val | Ser | Arg | Thr | Gly |
| | 690 | | | | | 695 | | | | | 700 | | | | |
| Arg | Gln | Val | Lys | Tyr | Ala | Gln | Ser | Gln | Val | Met | Phe | Pro | Ser | Pro | Asp |
| 705 | | | | | 710 | | | | | 715 | | | | | 720 |
| Ser | His | Pro | Thr | Asn | Ser | Ser | Ala | Ser | Thr | Pro | Val | Leu | Leu | Met | Gly |
| | | | | 725 | | | | | 730 | | | | | | 735 |
| Gln | Ala | Val | Leu | His | Pro | Ser | Phe | Pro | Ala | Ser | Arg | Pro | Ser | Pro | Leu |
| | | | 740 | | | | | 745 | | | | | 750 | | |
| Gln | Pro | Ala | Gln | Ala | Gln | Gln | Gln | Pro | Pro | Pro | Tyr | Leu | Gln | Ala | Pro |
| | | 755 | | | | | 760 | | | | | 765 | | | |
| Thr | Ser | Leu | His | Ser | Glu | Gln | Pro | Asp | Ser | Leu | Leu | Leu | Ser | Thr | Phe |
| | 770 | | | | | 775 | | | | | 780 | | | | |
| Ser | Gln | Gln | Pro | Gly | Thr | Leu | Gly | Tyr | Ala | Ala | Thr | Gln | Ser | Thr | Pro |
| 785 | | | | | 790 | | | | | 795 | | | | | 800 |
| Pro | Gln | Pro | Pro | Arg | Pro | Ser | Arg | Arg | Val | Ser | Arg | Leu | Ser | Glu | Ser |
| | | | | 805 | | | | | 810 | | | | | 815 | |